United States Patent
Yoon et al.

(10) Patent No.: US 7,820,306 B2
(45) Date of Patent: *Oct. 26, 2010

(54) COMPOUND AND ORGANIC LIGHT EMITTING DEVICE USING THE SAME

(75) Inventors: Seok Hee Yoon, Daejeon (KR); Jae Min Moon, Daejeon (KR); In Ho Hwang, Daejeon (KR); Min Jeong Lee, Seoul (KR); Wook Dong Cho, Daejeon (KR); Ji Eun Kim, Daejeon (KR); Byung Sun Jeon, Seoul (KR)

(73) Assignee: LG Chem, Ltd., Seoul (KR)

( * ) Notice: Subject to any disclaimer, the term of this patent is extended or adjusted under 35 U.S.C. 154(b) by 821 days.

This patent is subject to a terminal disclaimer.

(21) Appl. No.: 11/660,858

(22) PCT Filed: Sep. 23, 2005

(86) PCT No.: PCT/KR2005/003169

§ 371 (c)(1),
(2), (4) Date: Feb. 22, 2007

(87) PCT Pub. No.: WO2006/080637

PCT Pub. Date: Aug. 3, 2006

(65) Prior Publication Data

US 2007/0292715 A1      Dec. 20, 2007

(30) Foreign Application Priority Data

Sep. 24, 2004   (KR) .................... 10-2004-0077214

(51) Int. Cl.
*H01L 51/54* (2006.01)
(52) U.S. Cl. .................. 428/690; 428/917; 313/504; 313/506; 252/301.16; 257/40; 257/E51.032; 556/408; 546/15; 546/16; 546/18
(58) Field of Classification Search ................ 556/408
See application file for complete search history.

(56) References Cited

U.S. PATENT DOCUMENTS

| 6,329,082 | B1 * | 12/2001 | Kreuder et al. ............. 428/690 |
| 6,613,454 | B2 | 9/2003 | Ara et al. |
| 2003/0168970 | A1 * | 9/2003 | Tominaga et al. ........... 313/504 |
| 2004/0219386 | A1 | 11/2004 | Thoms |

FOREIGN PATENT DOCUMENTS

| JP | 2008-510801 | 4/2008 |
| JP | 2008-511156 | 4/2008 |
| JP | 2008-511161 | 4/2008 |
| JP | 2008-511162 | 4/2008 |
| WO | WO 93/09074 | 5/1993 |
| WO | WO 2004/020371 A1 | 3/2004 |
| WO | WO 2006/003564 | 3/2006 |
| WO | WO 2006/080637 | 8/2006 |
| WO | WO 2006/080638 | 8/2006 |
| WO | WO 2006/080645 | 8/2006 |
| WO | WO 2006/080646 | 8/2006 |

OTHER PUBLICATIONS

Tritschler, Wolfgang et al., "Synthese und Konformation von Spiroacridanen", Chem. Ber. 117, 2703-2713 (1984).

* cited by examiner

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is an organic light emitting device. The organic light emitting device comprises a first electrode, organic material layer(s) comprising a light emitting layer, and a second electrode. The first electrode, the organic material layer(s), and the second electrode form layered structure and at least one layer of the organic material layer(s) include the compound of Formula 1 or the compound of Formula 1 into which a thermosetting or photo-crosslinkable functional group is introduced.

7 Claims, 1 Drawing Sheet

[Fig. 1]
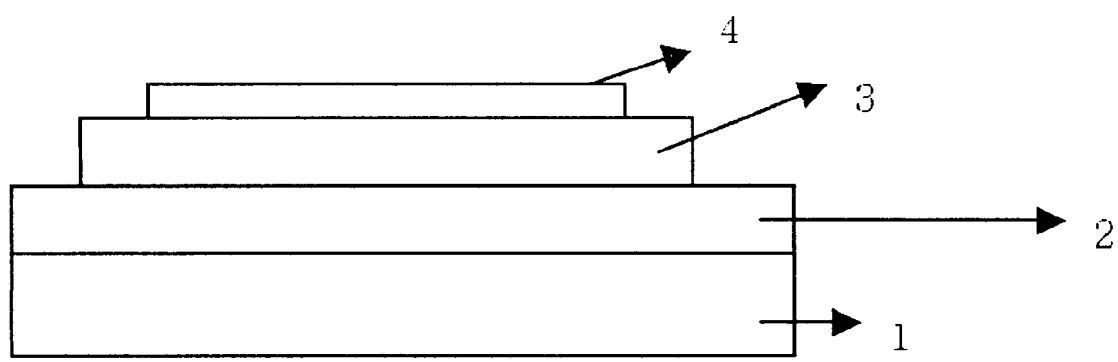
[Fig. 2]
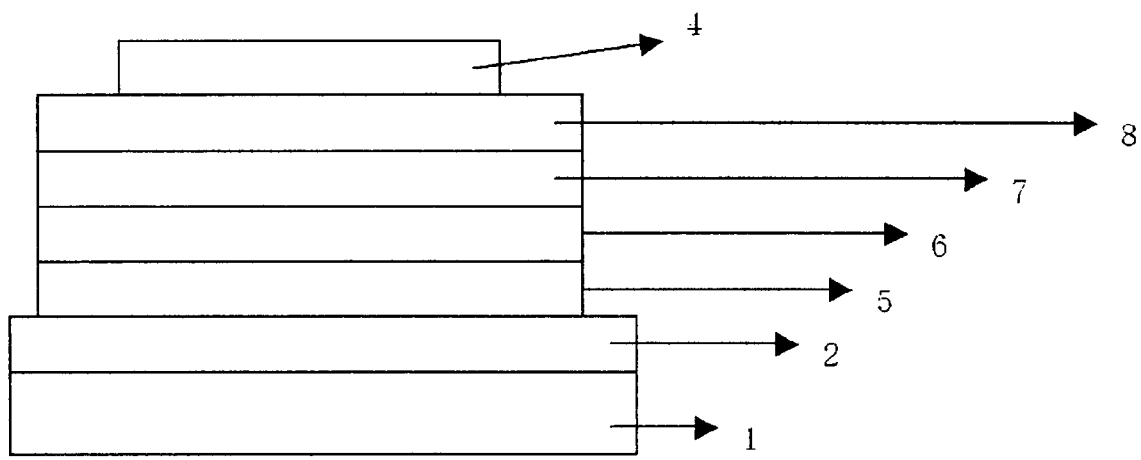

COMPOUND AND ORGANIC LIGHT EMITTING DEVICE USING THE SAME

This application claims priority to International application No. PCT/KR2005/003169 filed on Sep. 23, 2005, and Korean Application No. 10-2004-0077214 filed on Sep. 24, 2004, both of which are incorporated by reference, as if fully set forth herein.

TECHNICAL FIELD

The present invention relates to an organic light emitting device which comprises a fluorene derivative capable of significantly improving a lifespan, efficiency, and electrochemical and thermal stabilities thereof.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO and LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic light emitting device including an organic material having the above-mentioned requirements in the art.

DISCLOSURE OF INVENTION

Technical Problem

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Technical Solution

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

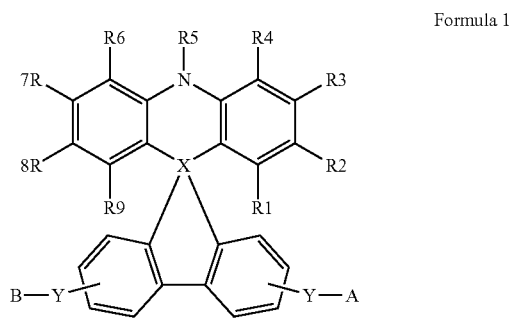

Formula 1

In Formula 1, X is C or Si, A is —NZ1Z2, B is —NZ3Z4,

Y is a bond or bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of the nitro, nitrile, halogen, alkyl, alkoxy, and amino groups.

Z1 to Z4 each are independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbons, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons.

R1 to R4, and R6 to R9 each are independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, and an ester group, and may form aliphatic or hetero condensation rings along with adjacent groups.

R5 is selected from the group consisting of hydrogen, a substituted or unsubstituted alkyl group, a substituted or unsubstituted cycloalkyl group, a substituted or unsubstituted alkenyl group, a substituted or unsubstituted aryl group, and a substituted or unsubstituted heterocyclic group.

In connection with this, when R5 is the aryl group or the heterocyclic group, carbon at an ortho-position of the aryl or the heterocyclic group and R4 or R6 may form a condensation ring along with a group selected from the group consisting of O, S, NR, PR, C=O, CRR', and SiRR'. R and R' are each independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group, and they may form a condensation ring to form a spiro compound.

A detailed description will be given of the substituent groups of Formula 1.

In Z1 to Z4 as the substituent groups of Formula 1, the aromatic hydrocarbons are exemplified by monocyclic aromatic rings, such as phenyl, biphenyl, and terphenyl, and multicyclic aromatic rings, such as naphthyl, anthracenyl, pyrenyl, and perylenyl. The heterocyclic group is exemplified by thiophene, furan, pyrrole, imidazole, thiazole, oxazole, oxadiazole, thiadiazole, triazole, pyridyl, pyridazyl, pyrazine, quinoline, and isoquinoline.

Examples of aliphatic hydrocarbons having a carbon number of 1-20 include straight chain aliphatic hydrocarbons, branched chain aliphatic hydrocarbons, saturated aliphatic hydrocarbons, and unsaturated aliphatic hydrocarbons. They are exemplified by an alkyl group, such as a methyl group, an ethyl group, an n-propyl group, an isopropyl group, an n-butyl group, a sec-butyl group, an iso-butyl group, a ter-butyl group, a pentyl group, and a hexyl group; an alkenyl group having a double bond, such as styryl; and an alkynyl group having a triple bond, such as an acetylene group.

The carbon number of the alkyl, alkoxy, and alkenyl groups of R1 to R9 of Formula 1 is not limited, but is preferably 1-20.

The length of the alkyl group contained in the compound does not affect the conjugate length of the compound, but may affect the method of applying the compound to the organic light emitting device, for example, a vacuum deposition method or a solution coating method.

Illustrative, but non-limiting, examples of the aryl group of R1 to R9 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R9 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R9 of Formula 1 include a thiophenyl group, a furan group, a pyrrole group, an imidazolyl group, a thiazolyl group, an oxazolyl group, an oxadiazolyl group, a thiazolyl group, a pyridyl group, a pyradazine group, a quinolinyl group, an isoquinoline group, and an acridyl group.

In addition, illustrative, but non-limiting, examples of the alkenyl, aryl, arylamine, and heterocyclic groups of R1 to R9 of Formula 1 include compounds shown in the following Formulae.

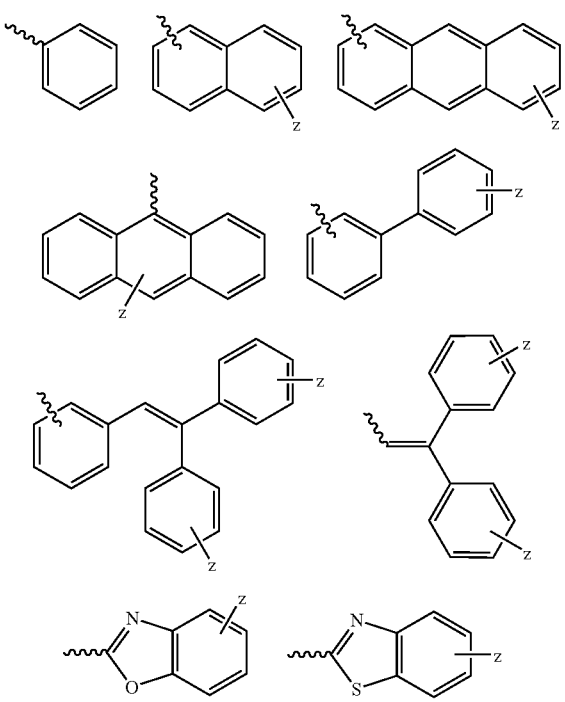

-continued

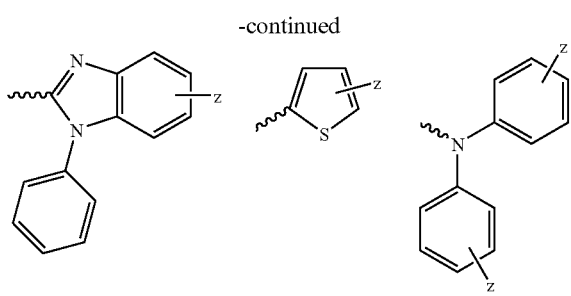

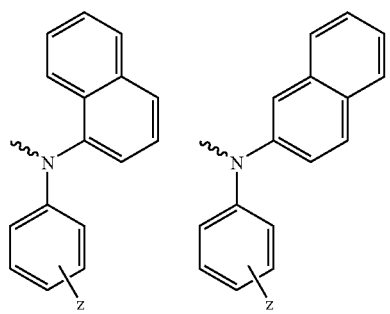

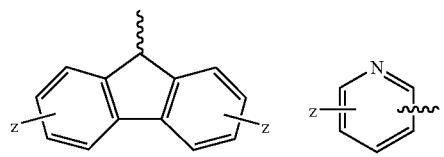

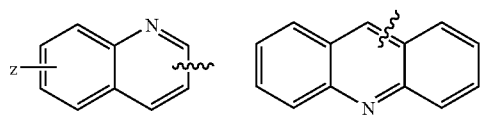

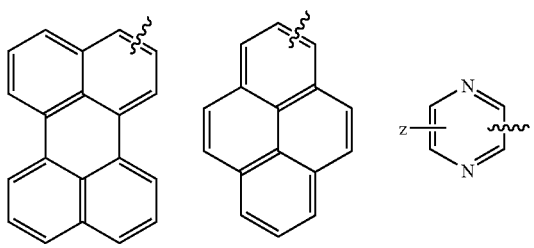

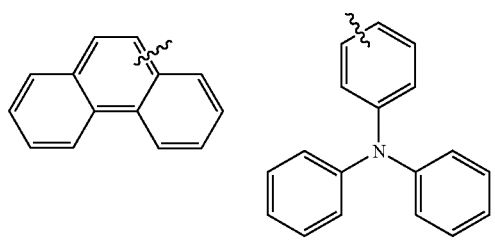

In the above Formulae, Z is a group selected from the group consisting of hydrogen, aliphatic hydrocarbons having 1-20 carbons, an alkoxy group, an arylamine group, an aryl group, a heterocyclic group, a nitrile group, and an acetylene group. Examples of the arylamine, aryl, and heterocyclic groups of Z are as shown in the above-mentioned substituent groups of R1 to R9.

According to a preferred embodiment of the present invention, R5 of Formula 1 is an aryl or an heterocyclic group.

According to another preferred embodiment of the present invention, R5 of Formula 1 is an aryl or an heterocyclic group, and carbon at an ortho-position of the aryl or the heterocyclic group and R4 or R6 form a condensation ring along with a group selected from the group consisting of O, S, NR, PR, C=O, CRR', and SiRR' (R and R' are as defined in Formula 1).

According to still another preferred embodiment of the present invention, R5 of Formula 1 is an aryl or an heterocyclic group, and a carbon at the ortho-position of the aryl or the heterocyclic group and R4, and a carbon at the ortho-position of the aryl or the heterocyclic group and R6 form the condensation ring along with a group selected from the group consisting of O, S, NR, PR, C=O, CRR', and SiRR' (R and R' are as defined in Formula 1).

According to the preferred embodiment of the present invention, illustrative, but non-limiting, examples of the compound of Formula 1 include compounds of the following Formulae 2 to 119.

[Formula 2 to 119]

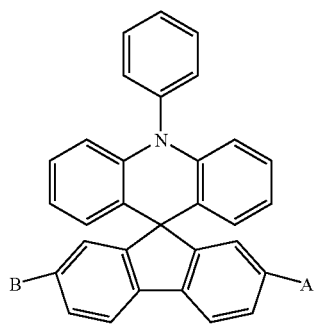

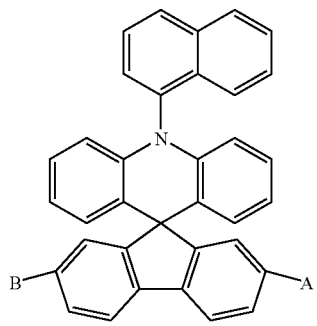

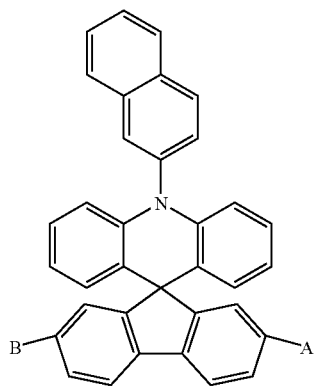

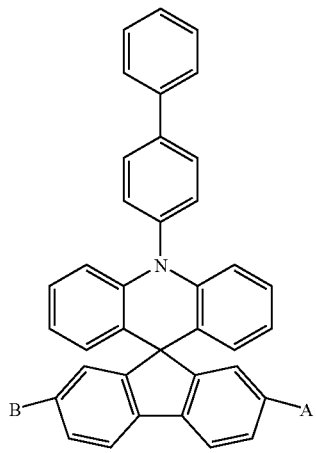
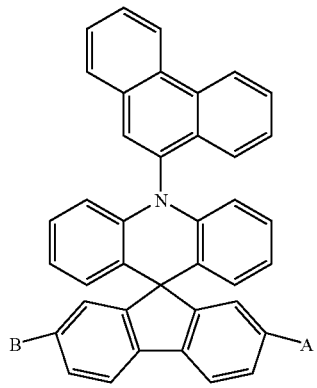

-continued
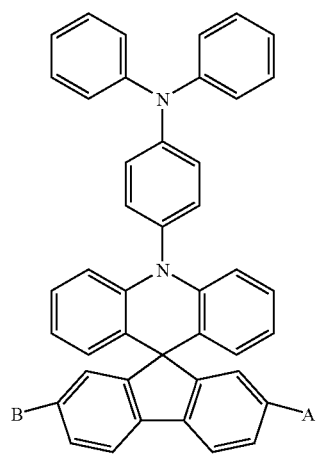
8
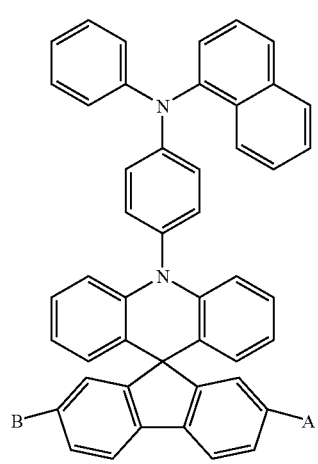
9
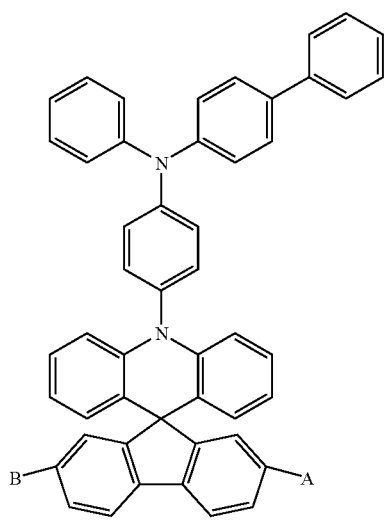
10
-continued
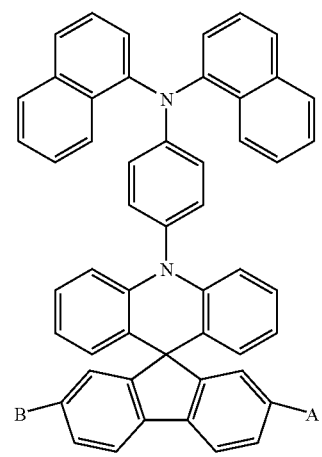
11
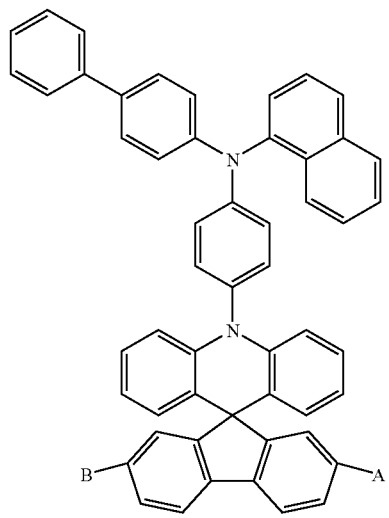
12
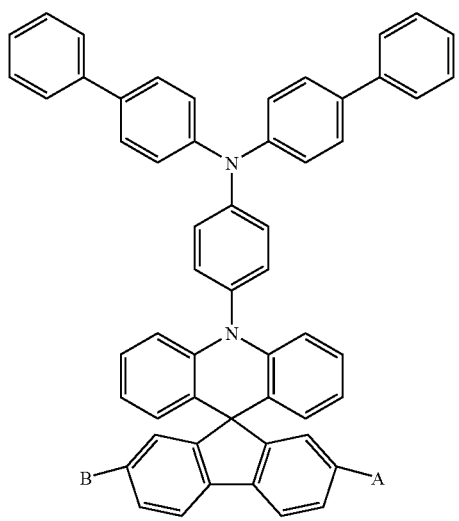
13

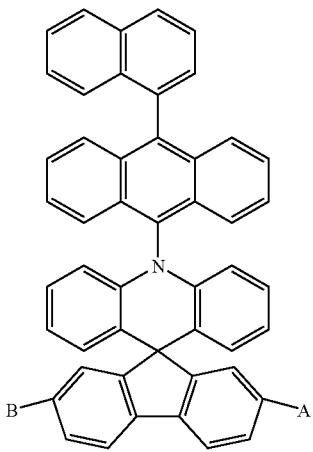
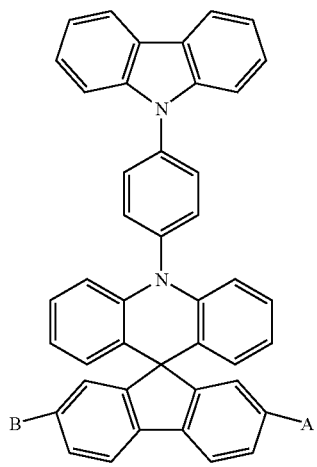
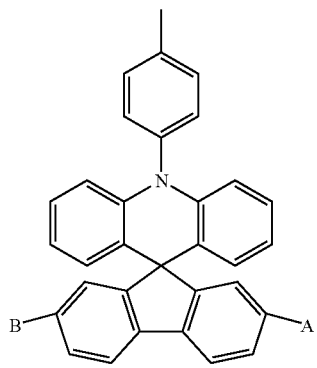
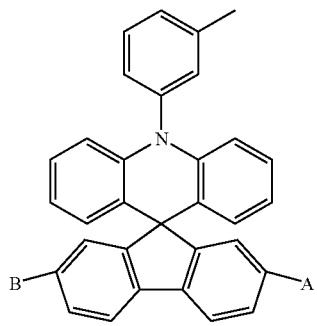
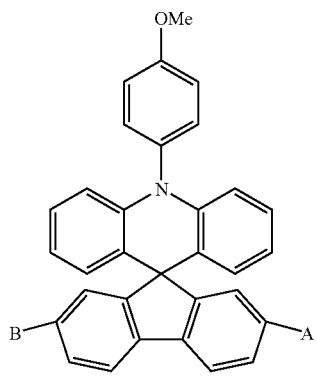

-continued
21
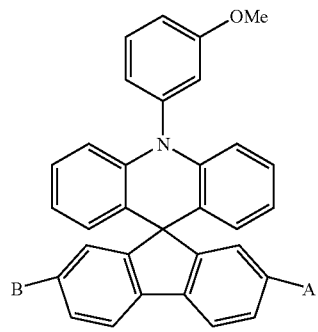
22
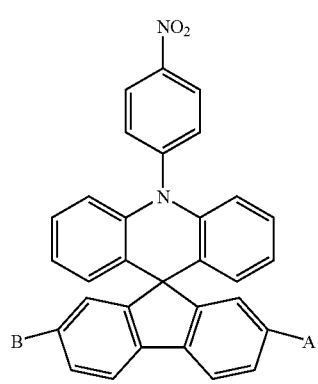
23
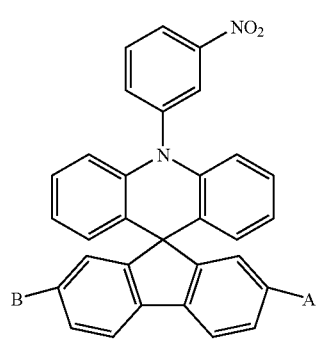
24
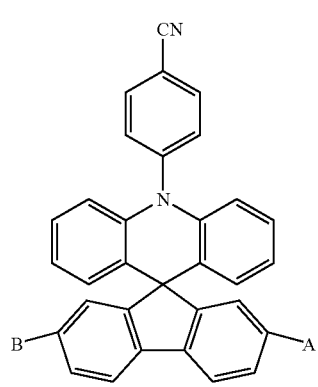
-continued
25
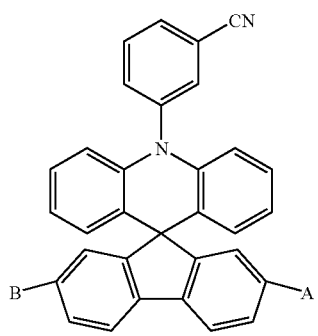
26
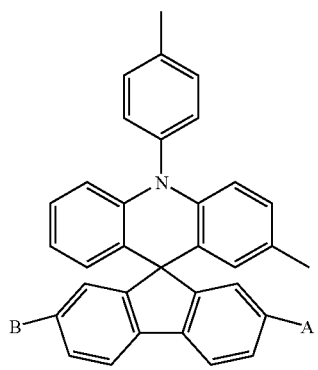
27
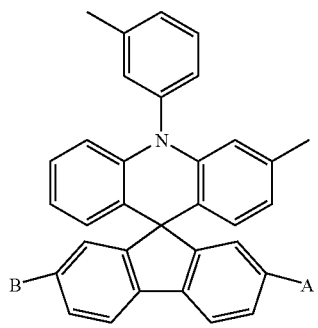
28
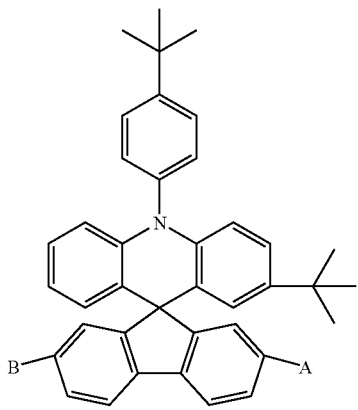

-continued
29
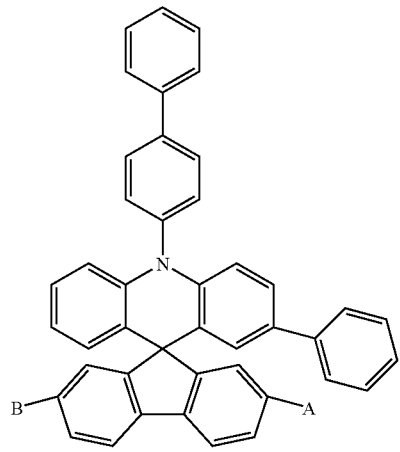
30
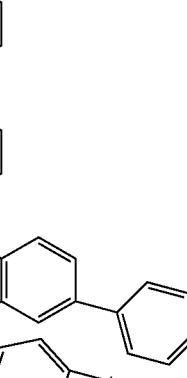
31
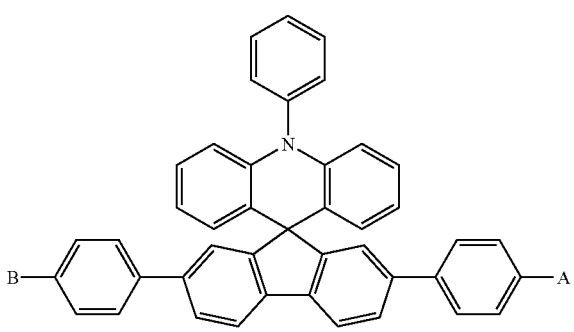
32
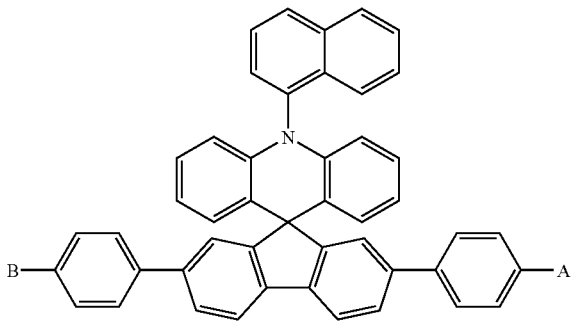
-continued
33
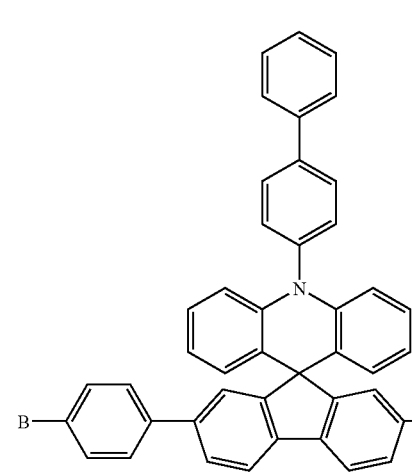
34
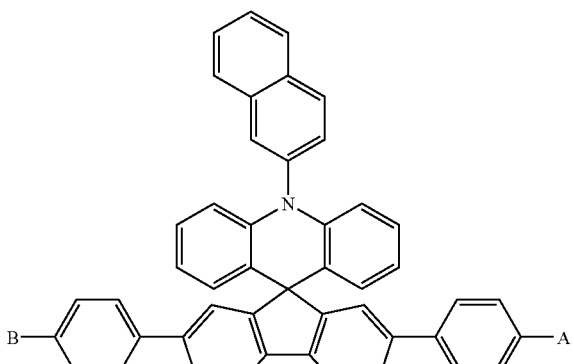
35
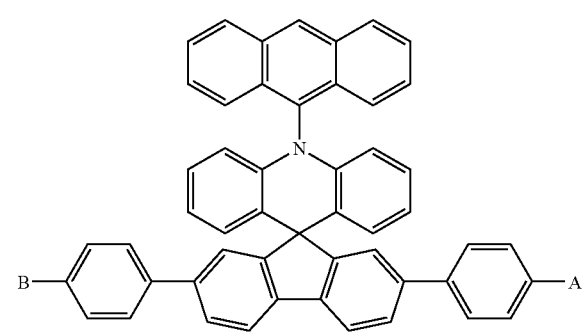

-continued

36

37

38

39

40

41

-continued
42
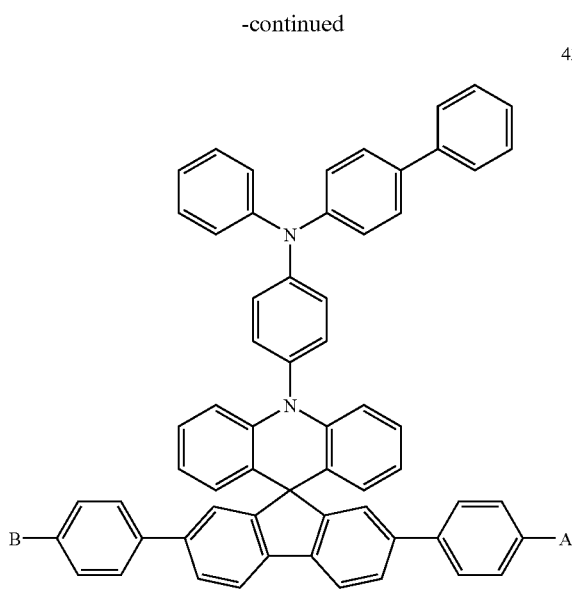
43
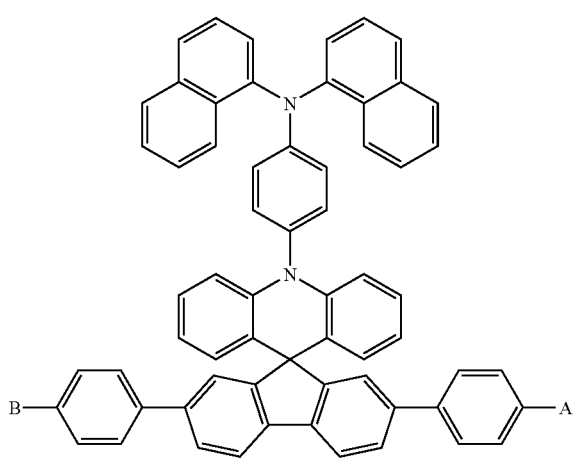
44
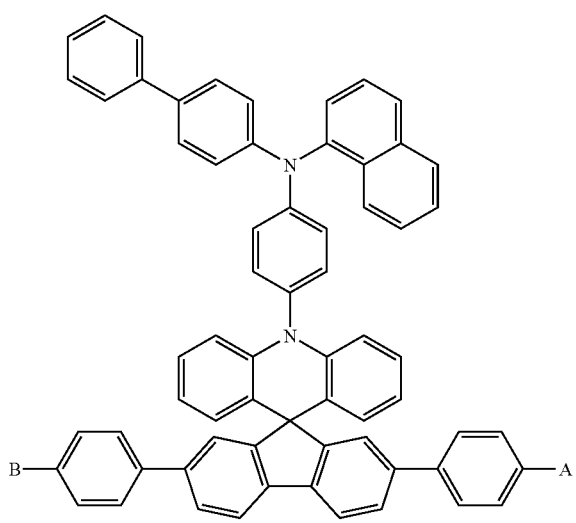
-continued
45
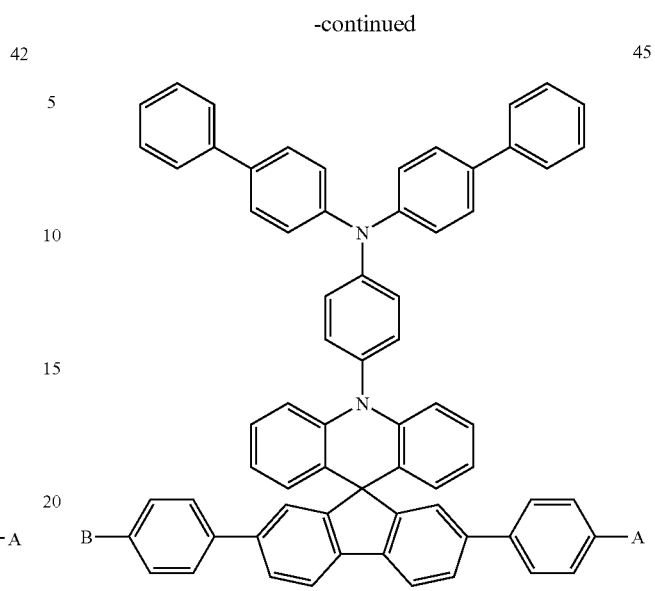
46
47

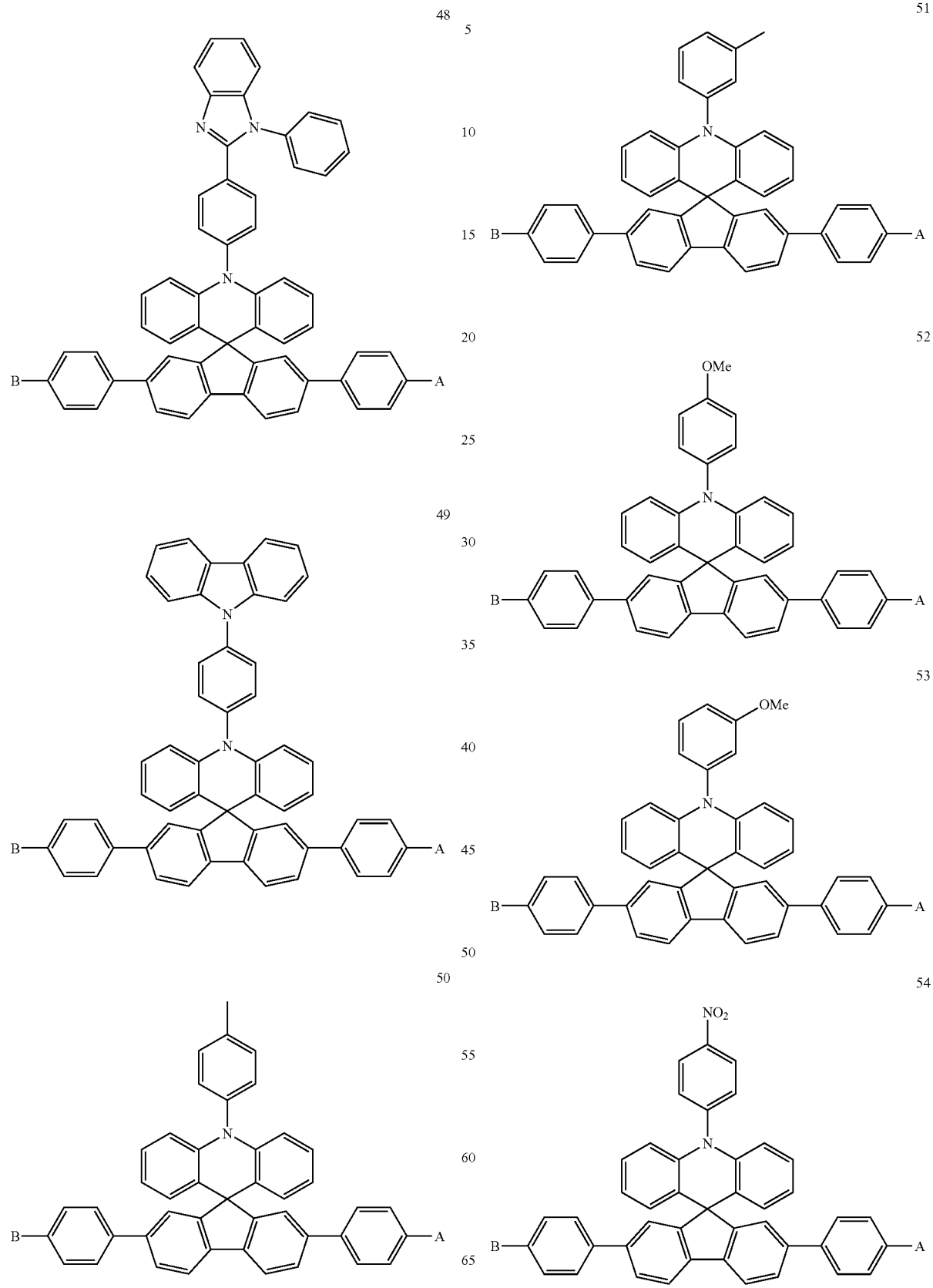

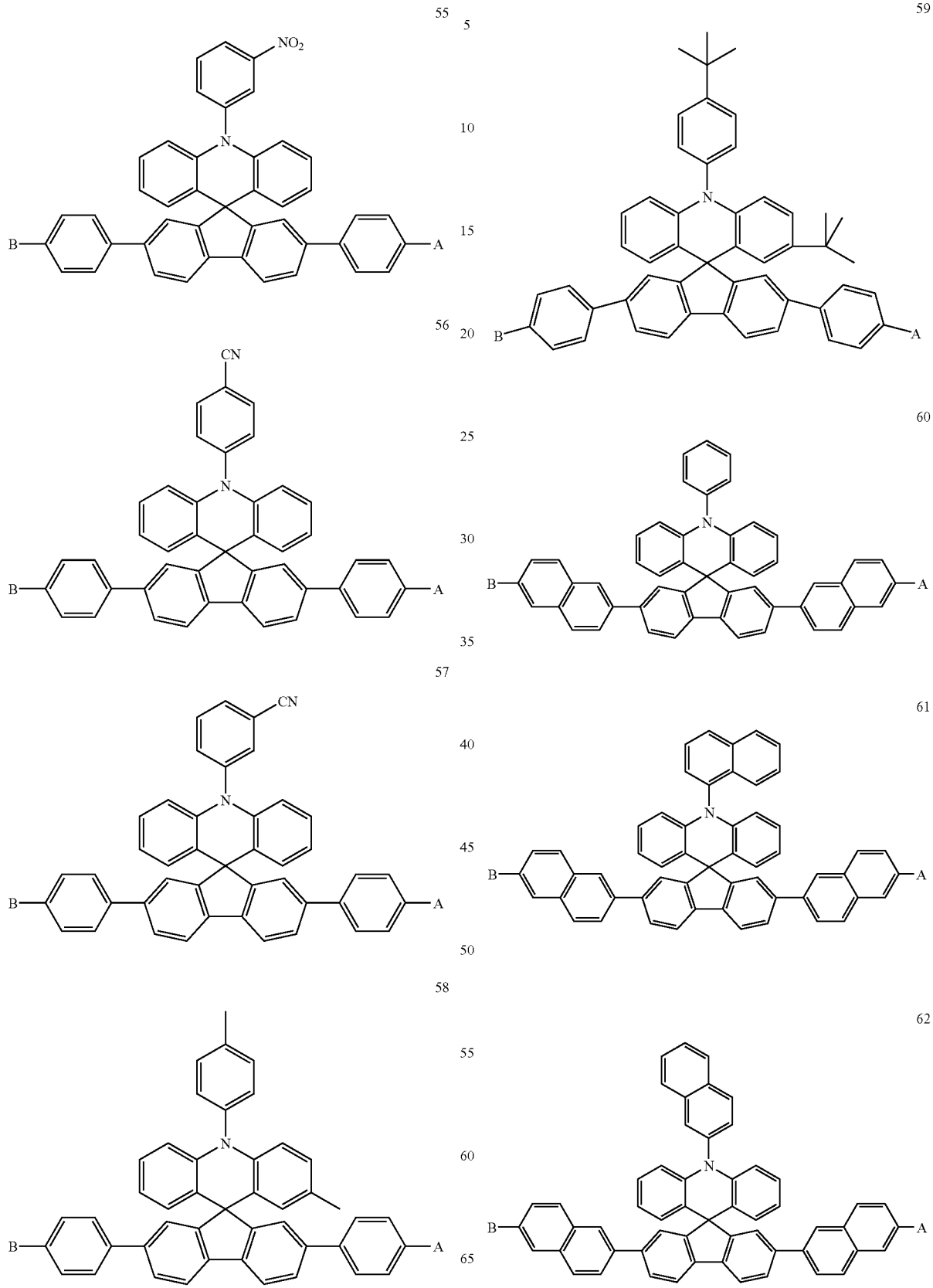

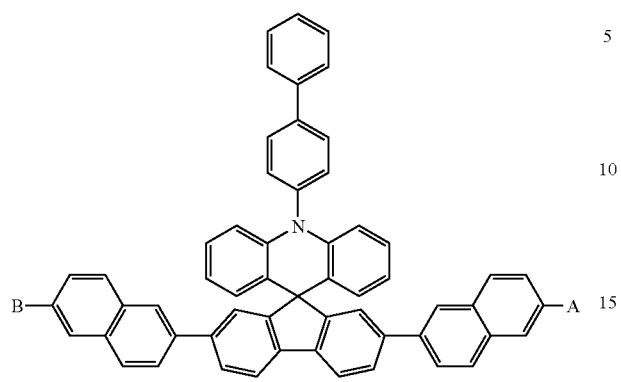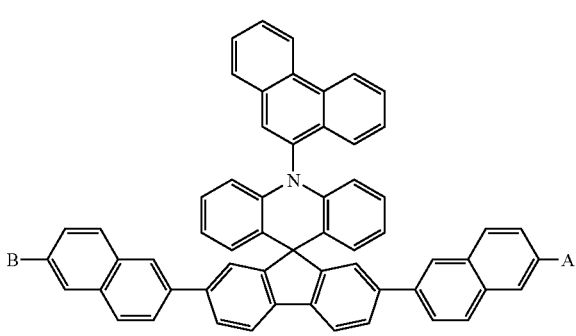

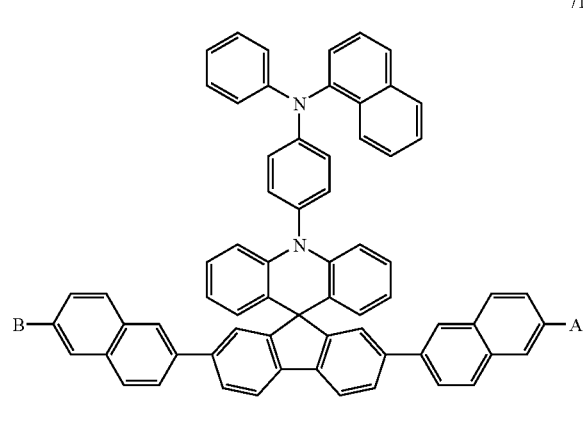
71
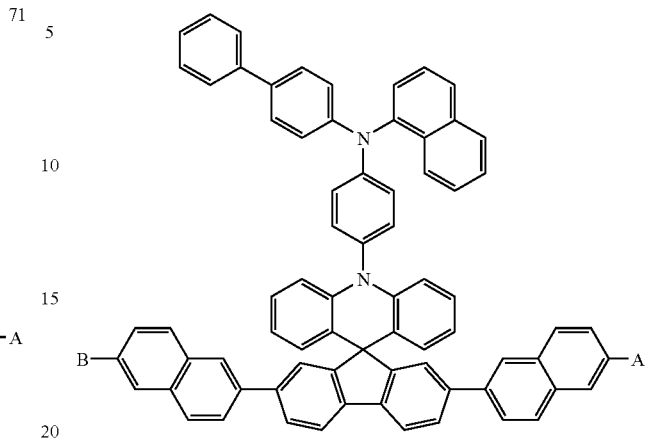
74
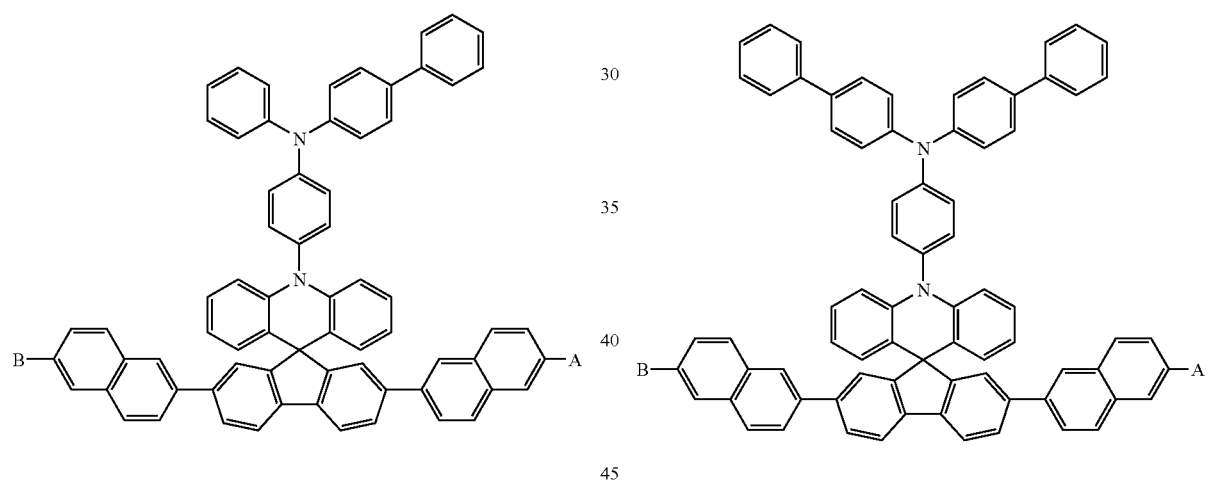
72
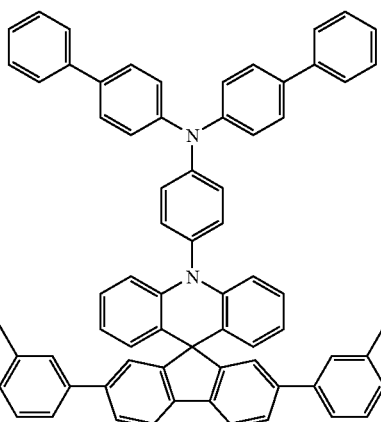
75
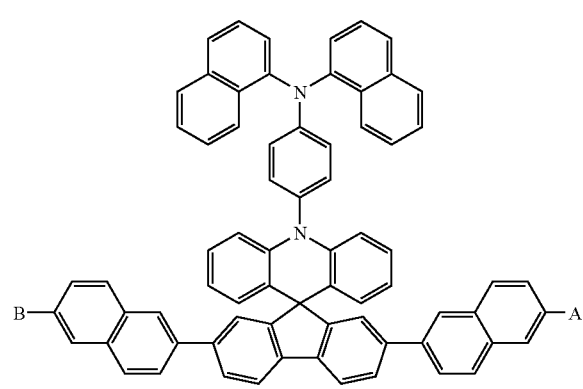
73
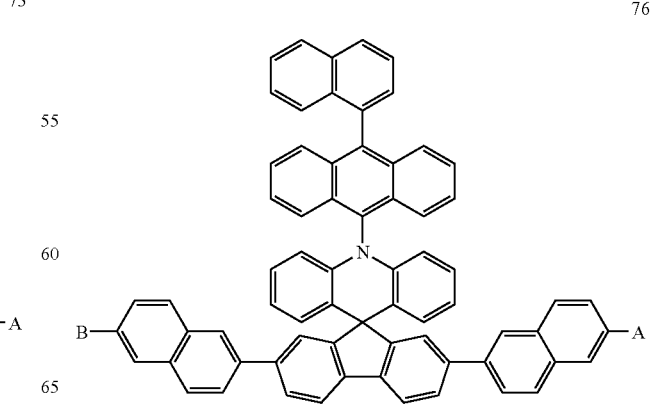
76

77
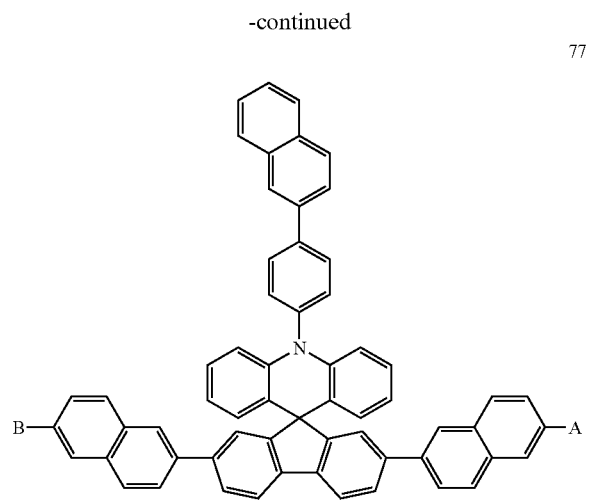
78
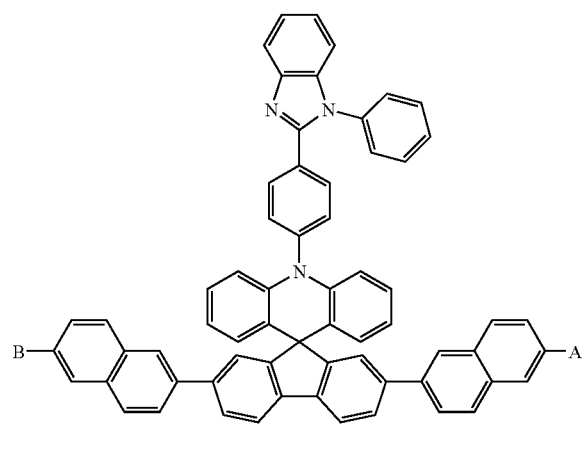
79
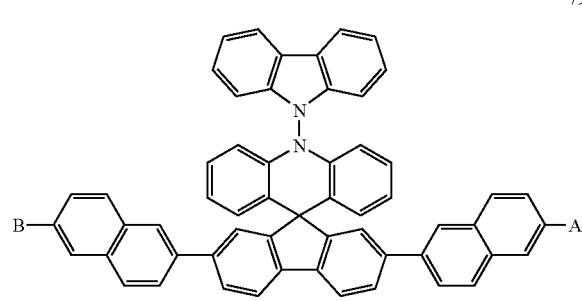
80
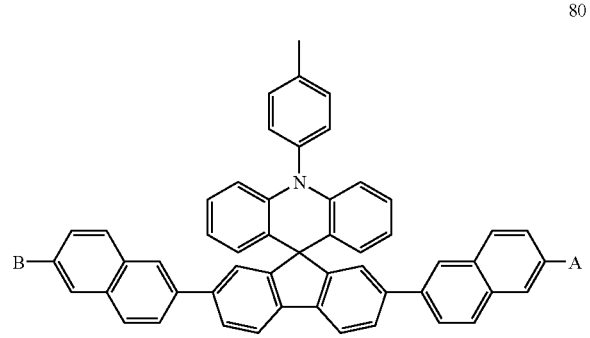
81
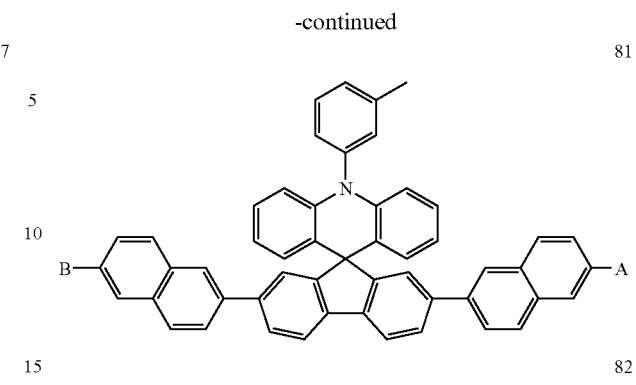
82
83
84
85

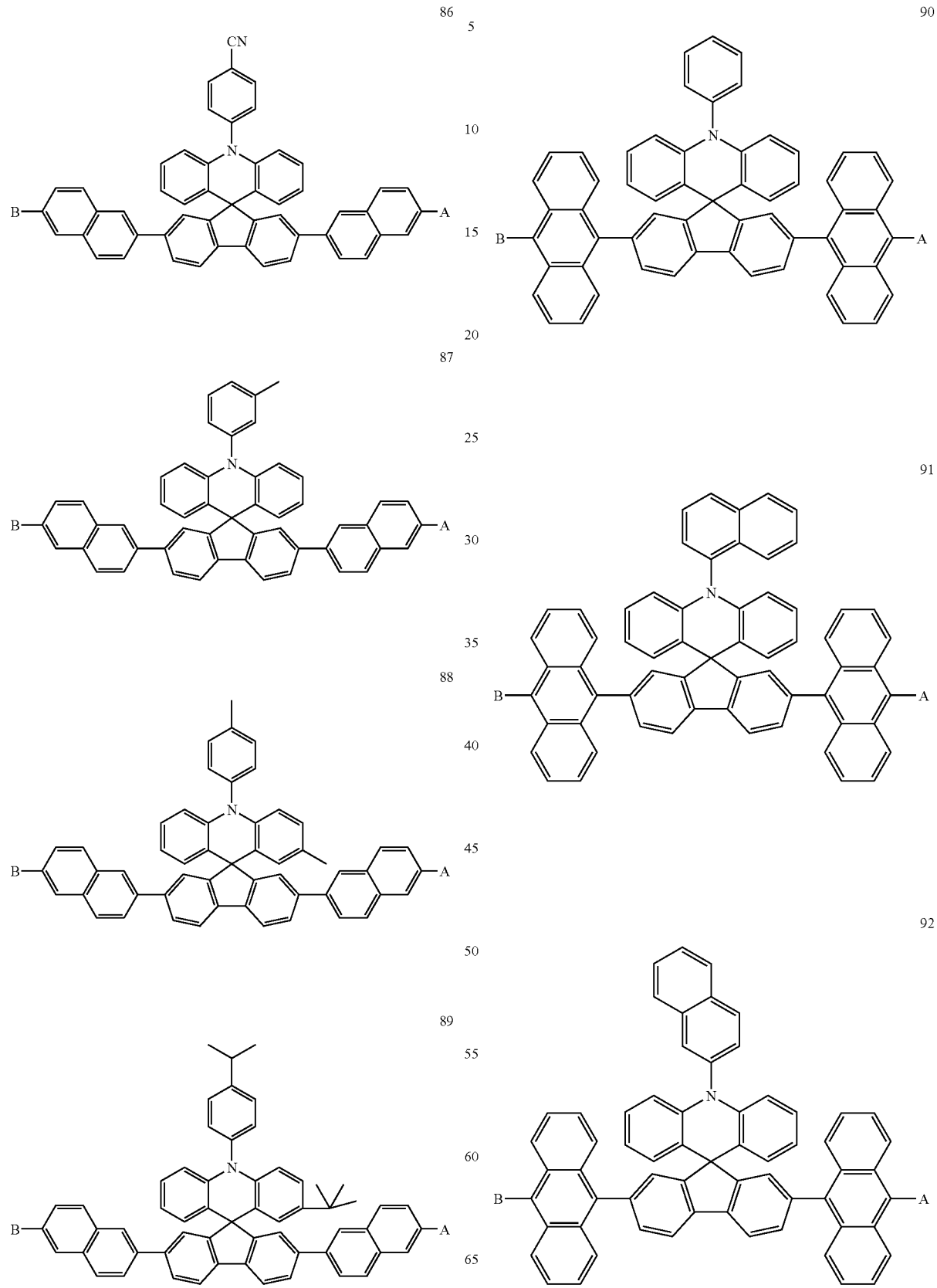

33 34
-continued -continued
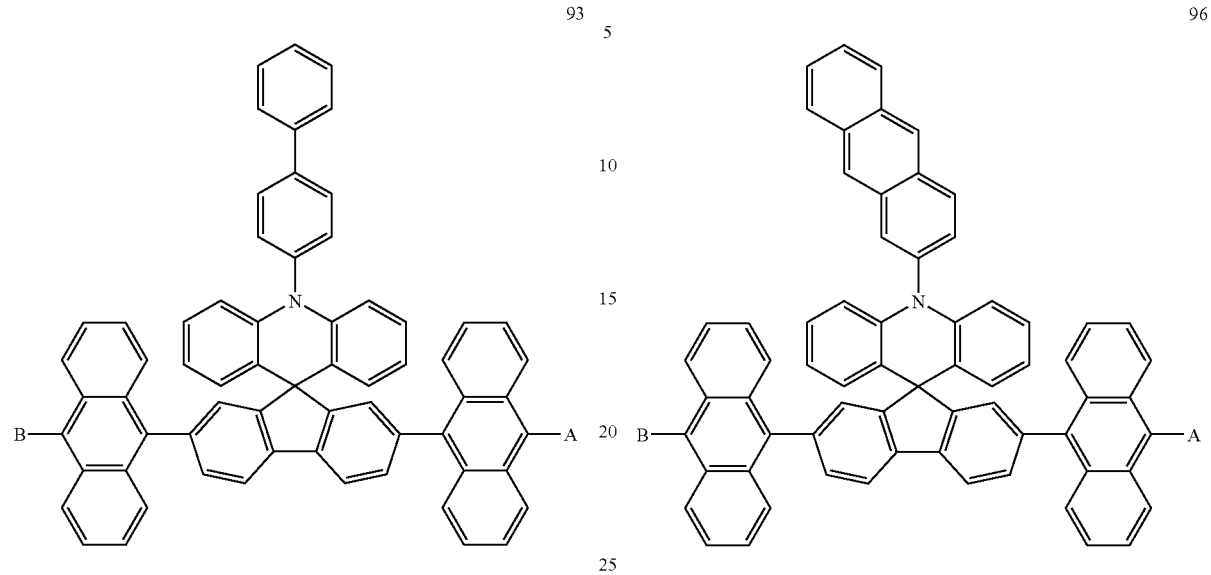
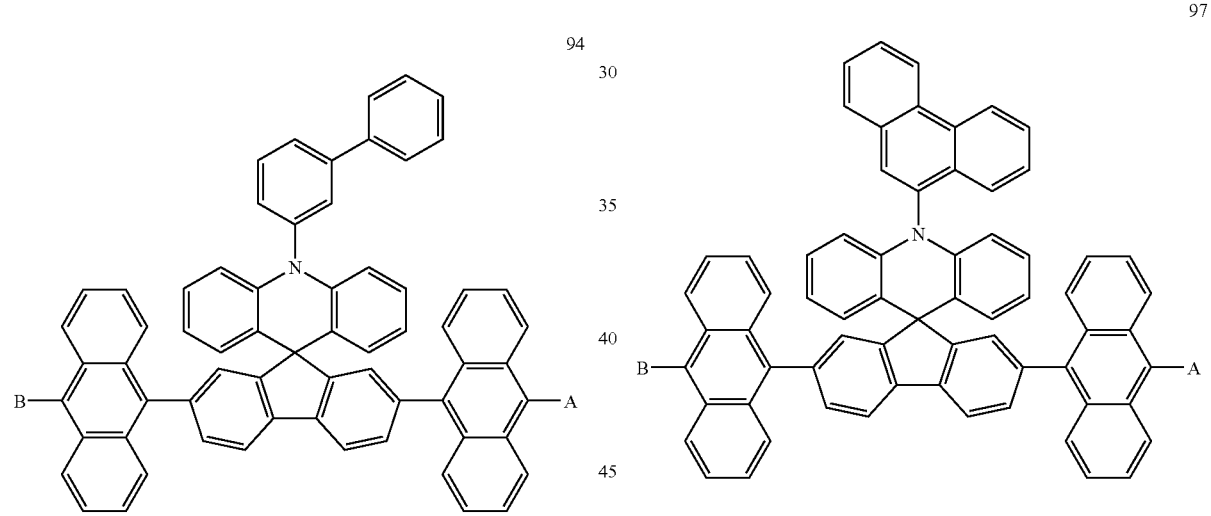
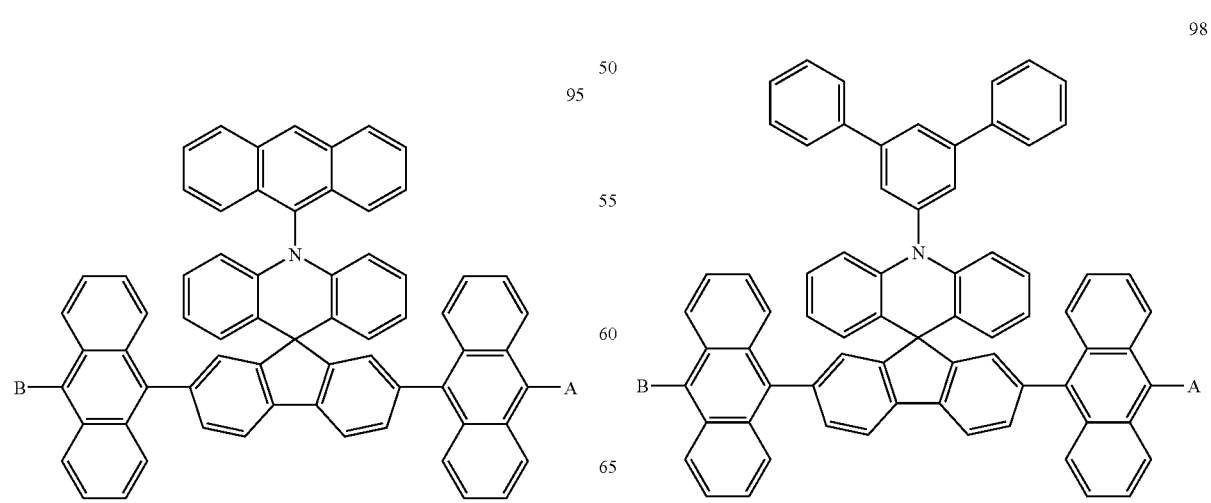

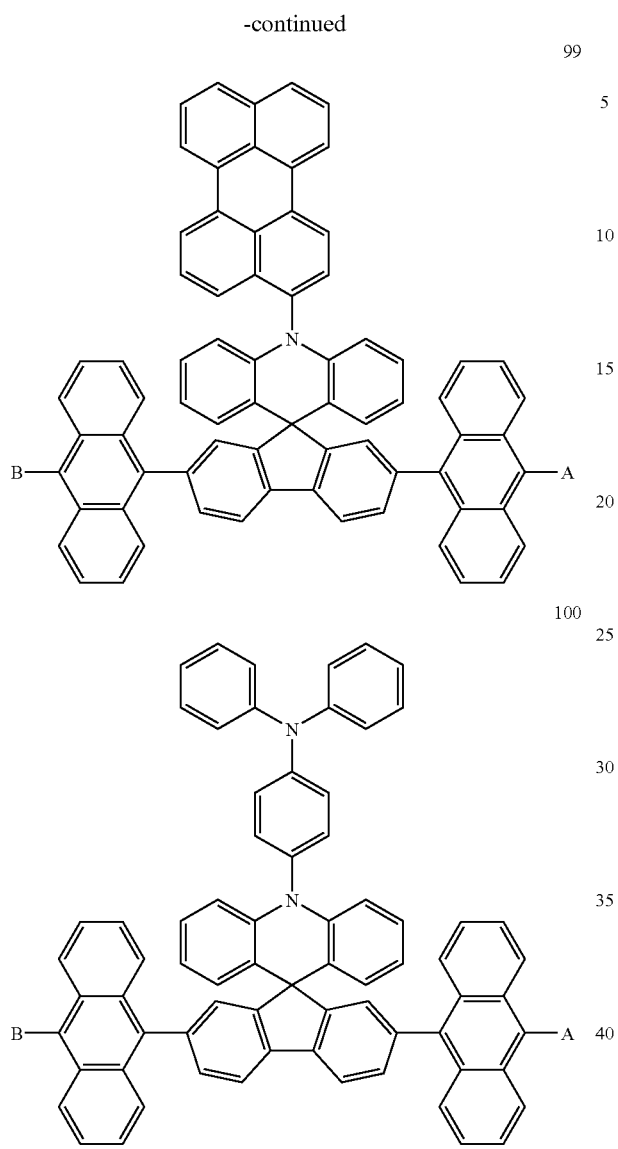
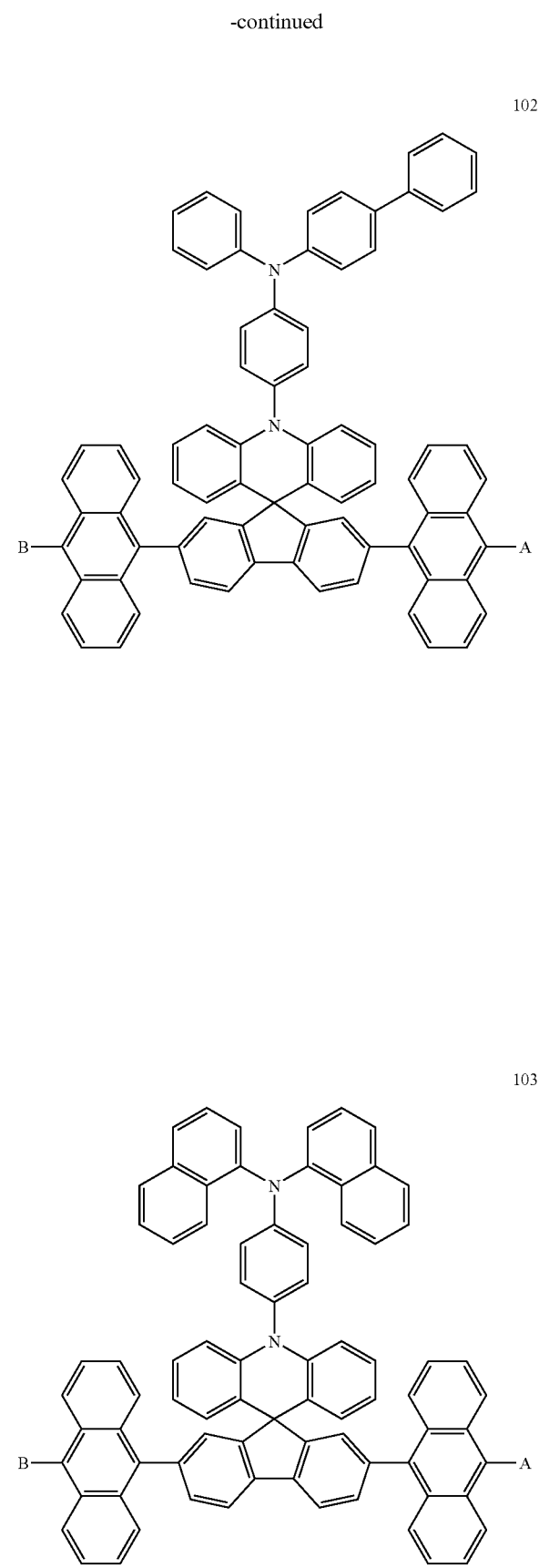

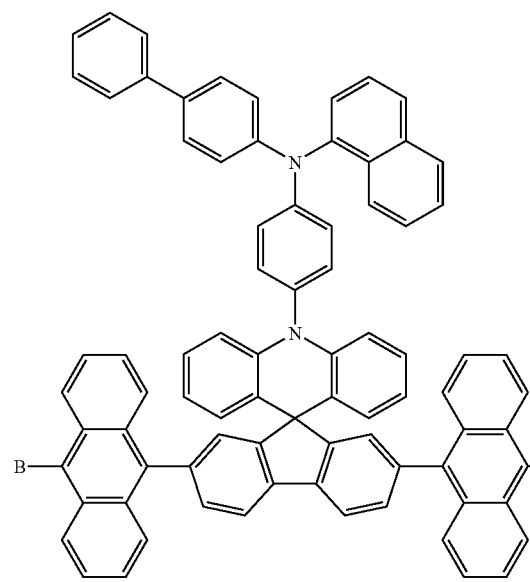
104
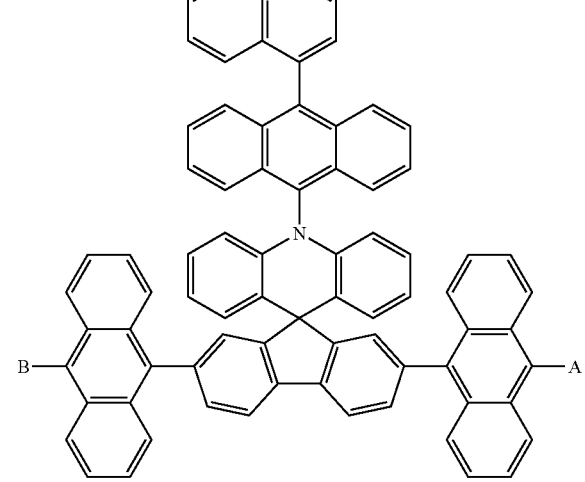
106
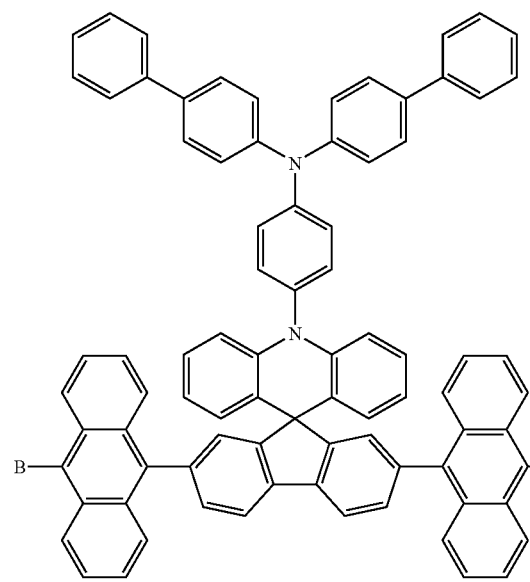
105
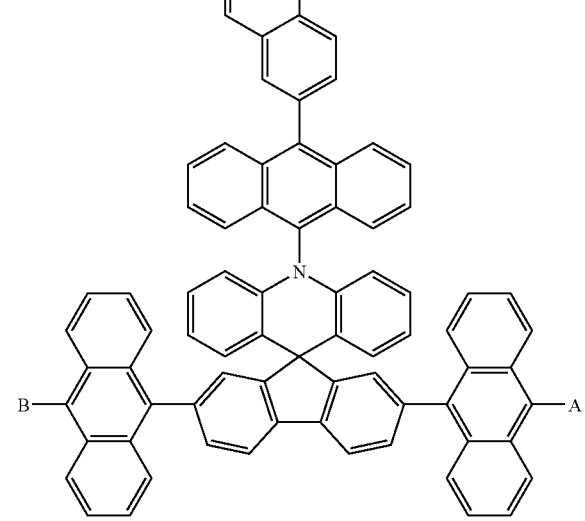
107

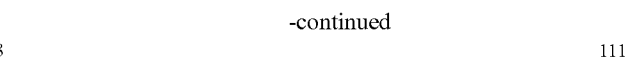
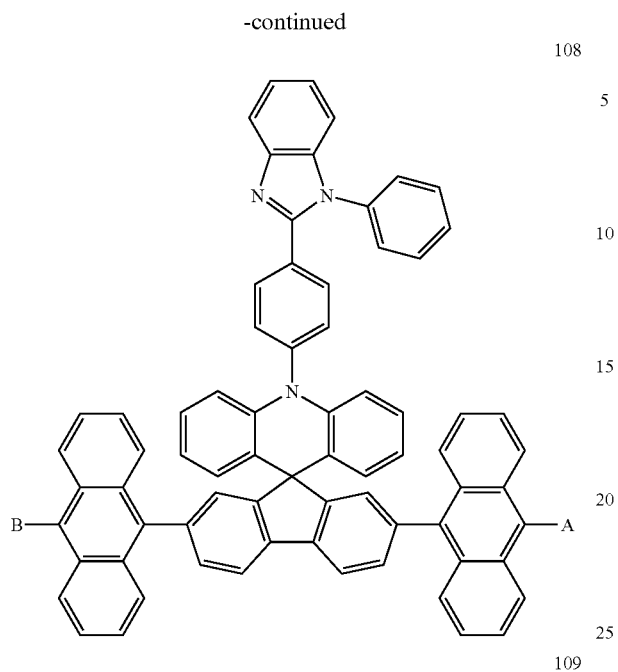
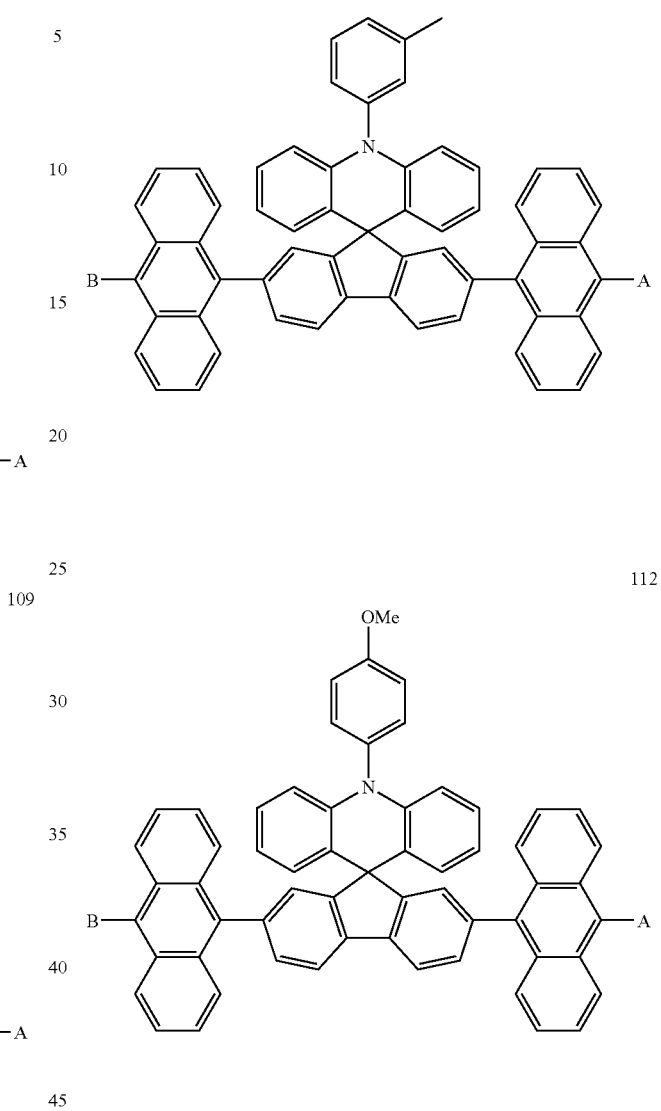

-continued

114
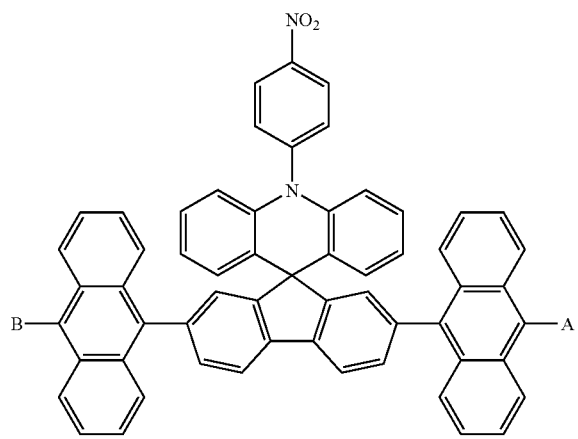

115
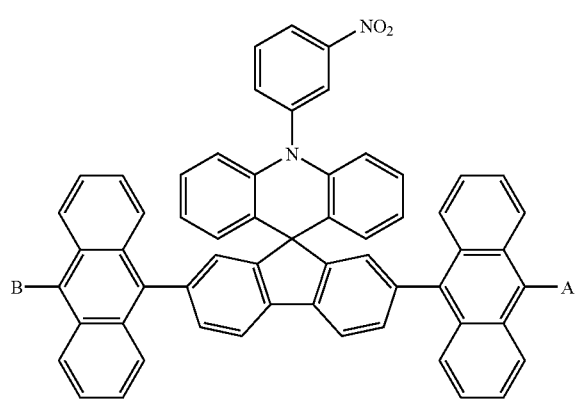

116
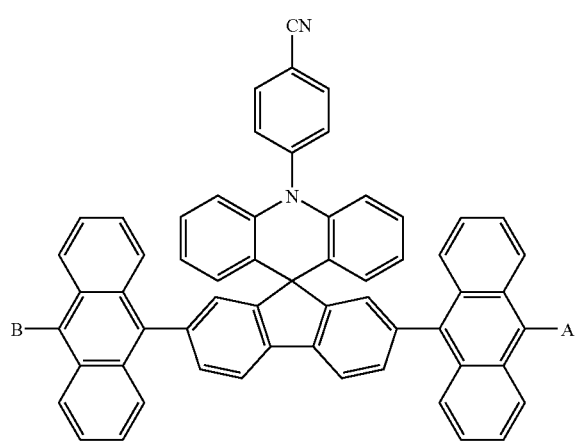

-continued

117
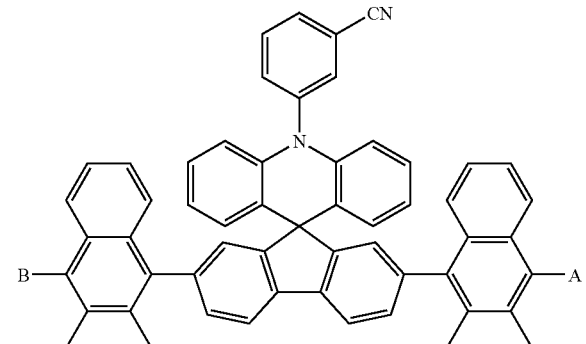

118
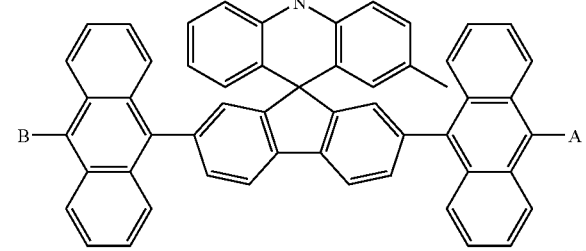

119
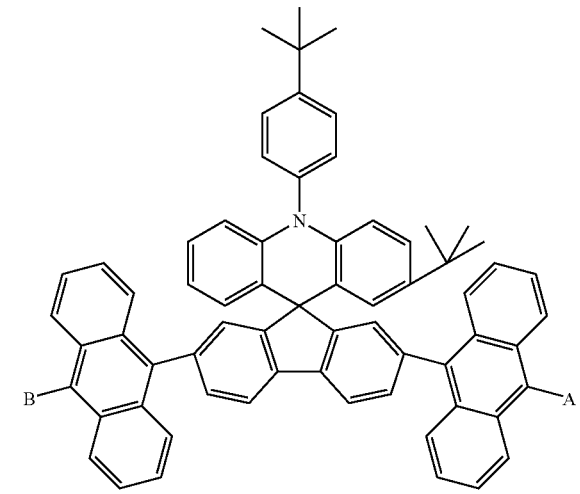

In the above Formulae, A and B are as defined in Formula 1.

Illustrative, but non-limiting, example of A and B are as follows.

Combination of the compounds of Formulae 2 to 119 and the following substituent groups A and B can form various derivative compounds. For example, if the compound of Formula 2 is combined with the substituent group 1, the resulting product will be designated by the compound of Formula 2-1.

[A and B]
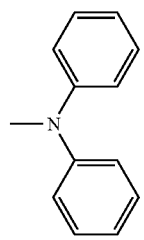
1
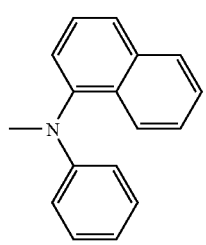
2
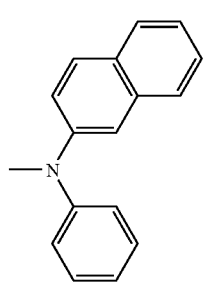
3
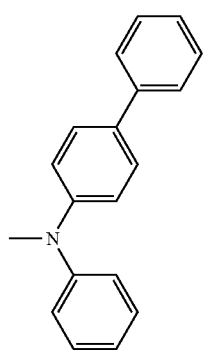
4
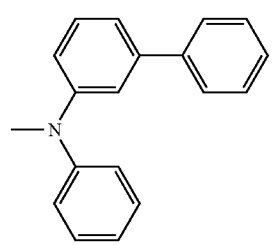
5
-continued
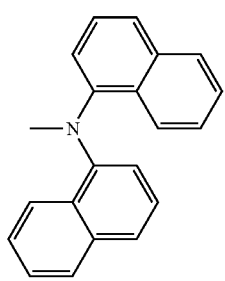
6
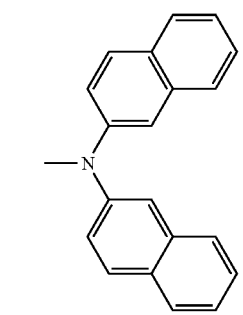
7
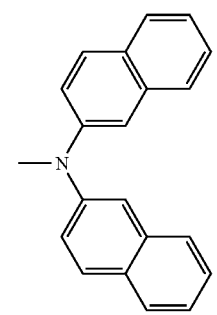
8
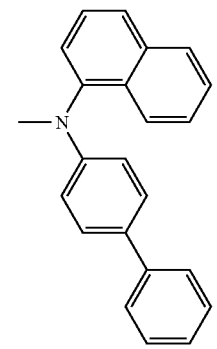
9
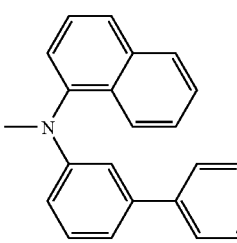
10
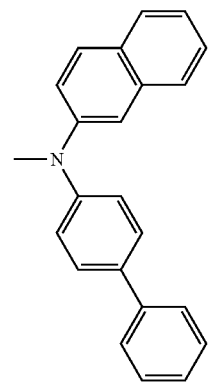

-continued
11
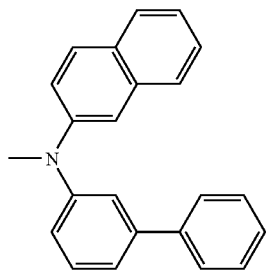
12
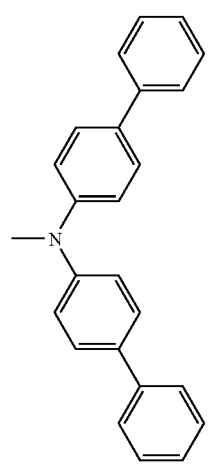
13
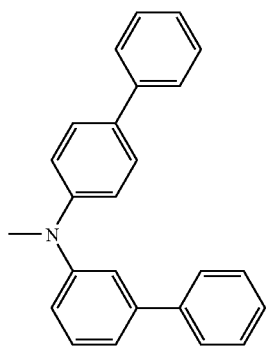
14
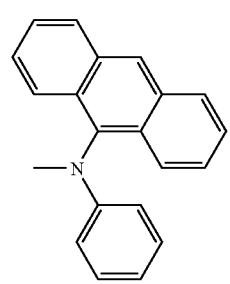
-continued
15
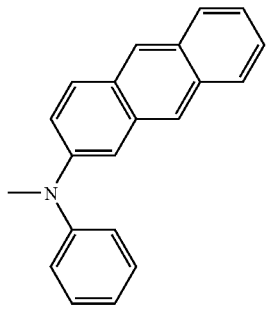
16
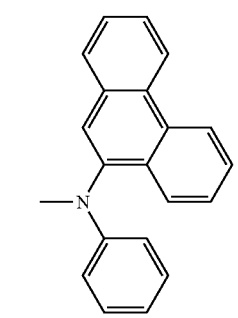
17
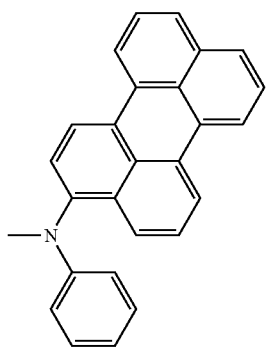
18
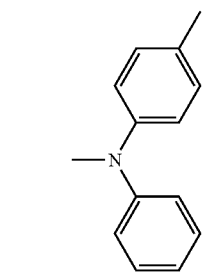
19
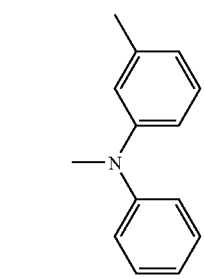

| 20 | 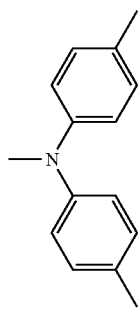 | 25 | 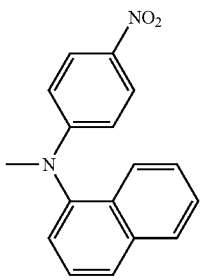 |
| 21 | 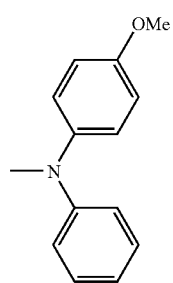 | 26 | 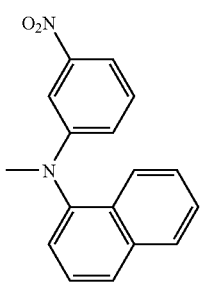 |
| 22 | 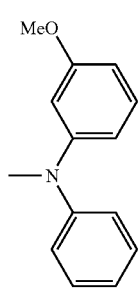 | 27 | 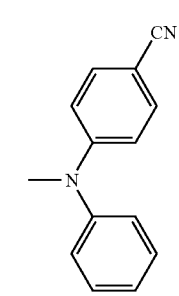 |
| 23 | 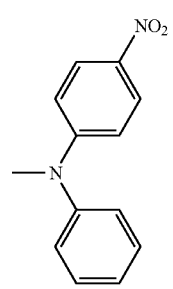 | 28 | 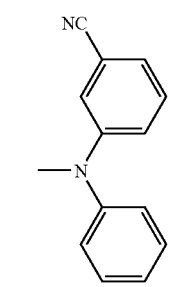 |
| 24 | 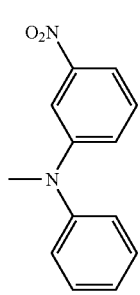 | 29 | 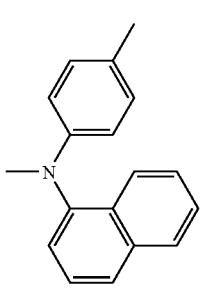 |

| | |
|---|---|
| 30 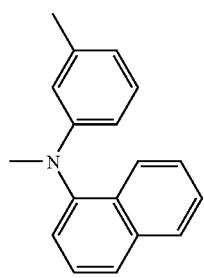 | 35 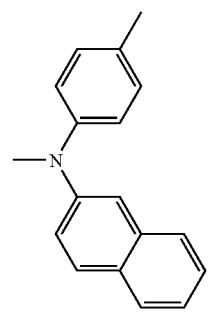 |
| 31 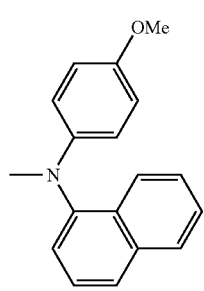 | 36 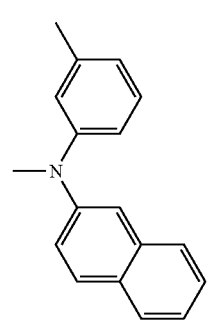 |
| 32 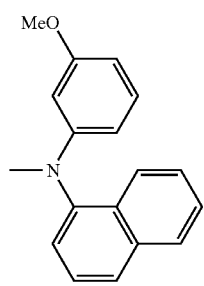 | 37 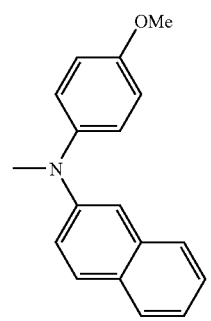 |
| 33 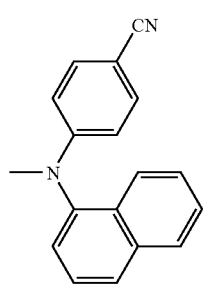 | 38 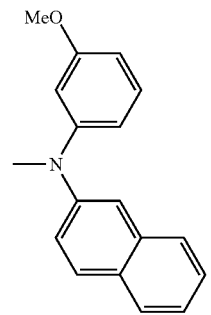 |
| 34 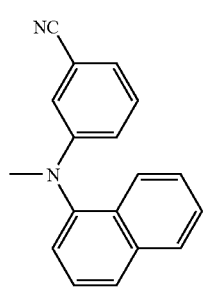 | 39 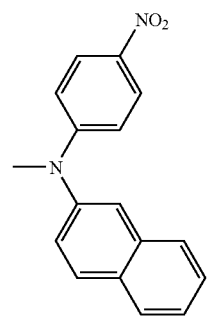 |

-continued
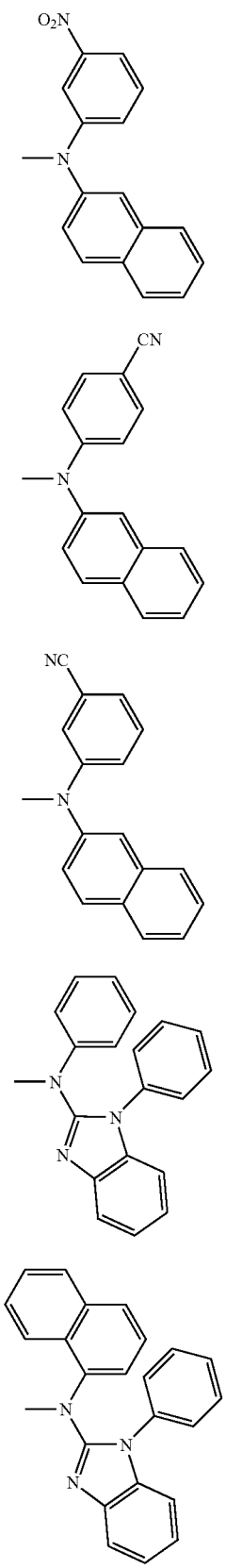
-continued
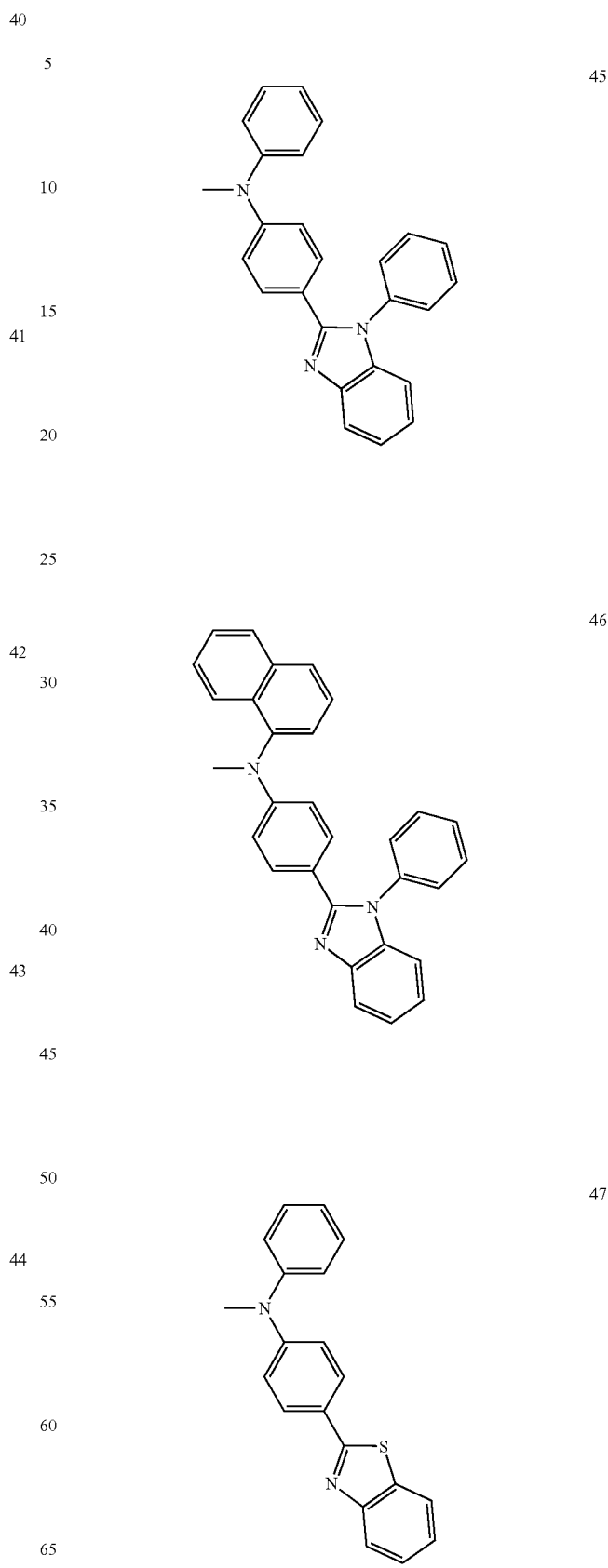

48
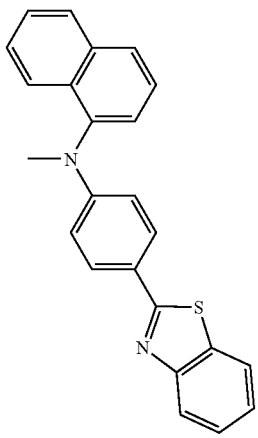
49
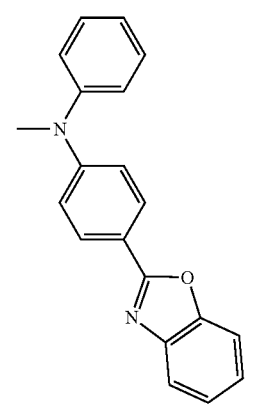
50
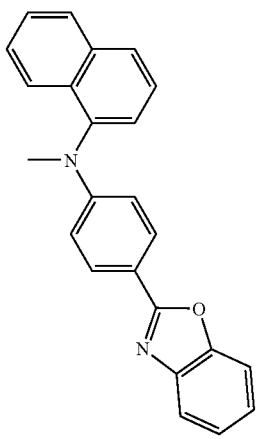
51
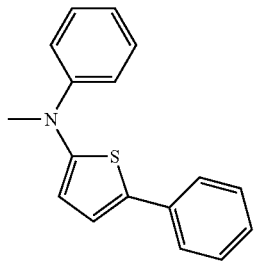
52
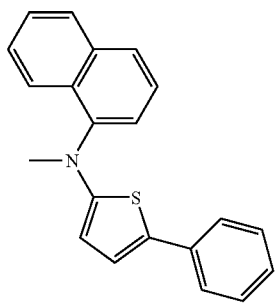
53
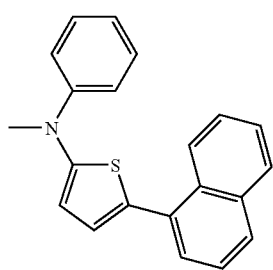
54
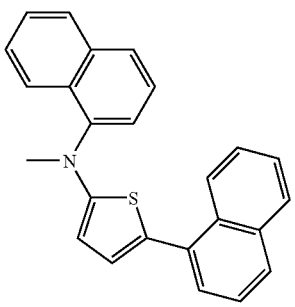
55
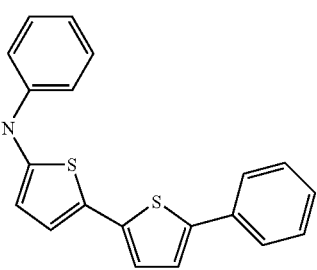
56
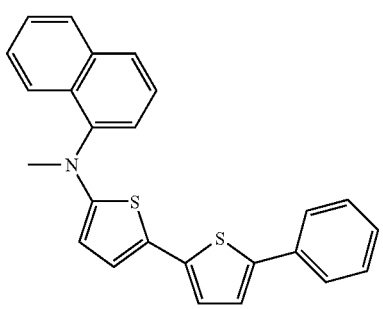

-continued

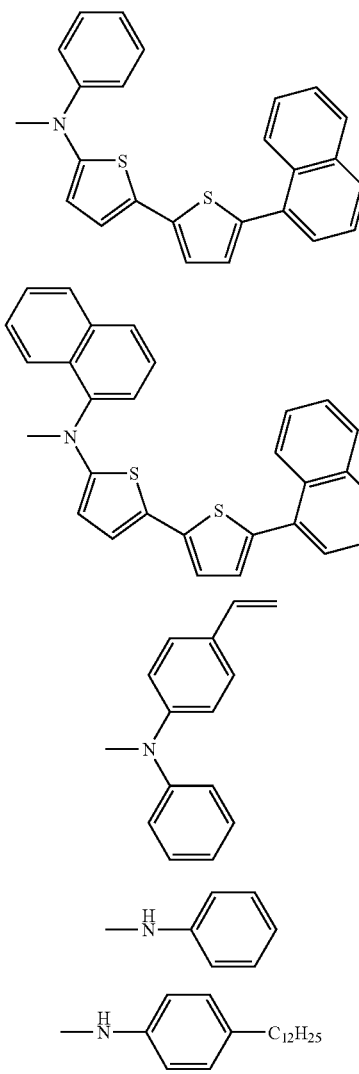

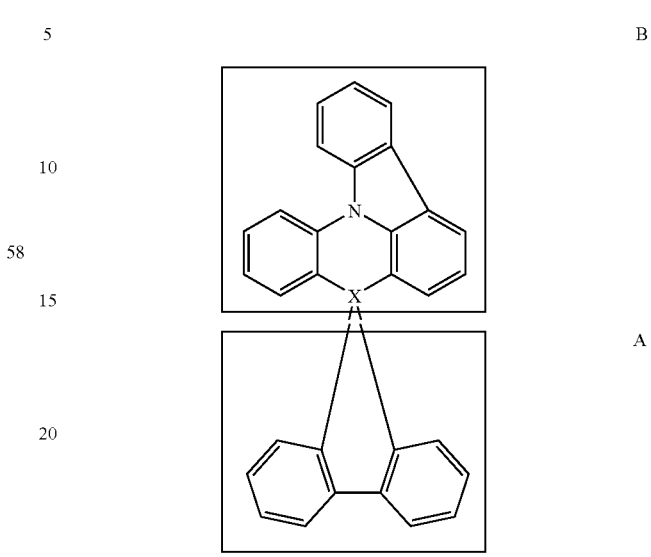

The steric core structure of the compound of Formula 1 can be divided into two portions, A and B, for explanation, as shown in the following figure.

The compound of Formula 1 has the steric core structure in which a plane A meets with a plane B at right angles around X, and conjugation does not occur between the A and B portions around X. Furthermore, since one nitrogen atom is positioned among three aryl groups in the plane B. conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1~R9 positions and Z1~Z4 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R9 and Z1 to Z4 of the core structure.

Additionally, by introducing various substituent groups into the core structure, compounds having intrinsic characteristics of the substituent groups can be obtained. For example, substituent groups, which are frequently applied to hole injection layer material, hole transport layer material, light emitting layer material, and electron transport layer materials during the production of the organic light emitting device, are introduced into the core structure so as to produce substances capable of satisfying the requirements of each organic material layer. Particularly, since the core structure of the compound of Formula 1 includes the arylamine structure, it has an energy level suitable for the hole injection and/or hole-transport materials in the organic light emitting device. In the present invention, the compound having the proper energy level is selected depending on the substituent group among the compounds expressed by Formula 1 to be used in the organic light emitting device, thereby it is possible to realize a device having a low actuating voltage and a high light efficiency.

BRIEF DESCRIPTION OF THE DRAWINGS

FIG. 1 illustrates an organic light emitting device comprising a substrate 1, an anode 2, a light emitting layer 3, and a cathode 4; and FIG. 2 illustrates an organic light emitting device comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of the present invention.

Various substituent groups are introduced into a core structure shown in Formula 1, in detail, the core structure in which a fluorene group is bonded to a combination of an acridine group and a carbazolyl group to form a spiro structure, thereby the compound of Formula 1 has characteristics suitable for application to an organic material layer used in an organic light emitting device. This will be described in detail, below.

Furthermore, various substituent groups are symmetrically introduced into the core structure (the A and B portions are located at both sides of the core structure) so as to precisely control the energy band gap, improve interfacial characteristics with organic materials, and apply the compound to various fields.

In addition, if the numbers of nitrogen contained in the substituent groups A and B are each set to 1 (if Z1 to Z4 are hetero aromatic amine compounds, the number of nitrogen contained in them is not counted), it is possible to precisely control the HOMO or LUMO energy levels and the energy band gap, on the other hand, to improve interfacial characteristics with the organic materials, and apply the compound to various fields.

Additionally, various substituent groups are introduced into the steric structure of the compound of Formula 1 using spiro bonding to control the three-dimensional structure of the organic material so as to minimize π-π interaction in the organic material, thereby formation of excimers is prevented.

Meanwhile, since the compound of Formula 1 has a high glass transition temperature (Tg), it has excellent thermal stability. For example, the glass transition temperature of the compound of Formula 2-4 is 148° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 1 has excellent solubility to a polar solvent, such as xylene, dichloroethane, or NMP, which is used during the production of the device, and forms a thin film very well through the process using a solution, thus the solution coating process may be applied to produce the device.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

In the organic light emitting device of the present invention, a compound, in which a thermosetting or photo-crosslinkable functional group is introduced into the compound of Formula 1, may be used instead of the compound of Formula 1. The former compound has the basic physical properties of the compound of Formula 1, and may be used to form a thin film using a solution coating process and then be cured so as to form an organic material layer during the production of the device.

The method of forming the organic material layer, which comprises introducing the curable functional group into the organic material during the Preparation of the organic light emitting device, forming the organic thin film using the solution coating process, and curing the resulting film, is disclosed in U.S. Pat. No. 2003-0044518 and EP Pat. No. 1146574A2.

The above documents state that, if the organic material layer(s) is formed through the above-mentioned method using a material having a thermosetting or photo-crosslinkable vinyl or acryl group so as to produce an organic light emitting device, it is possible to produce an organic light emitting device having a low voltage and high brightness as well as an organic light emitting device having a multilayered structure using the solution coating process. This operation mechanism may be applied to the compound of the present invention.

In the present invention, the thermosetting or photo-crosslinkable functional group may be a vinyl or an acryl group.

The organic light emitting device of the present invention can be produced using known materials through a known process, modified only in that at least one layer of organic material layer(s) include the compound of the present invention, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, and an electron injection layer as the organic material layer (s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the Preparation of the organic light emitting device using the same will be described in detail in the following preparation examples and examples. However, the following preparation examples and examples are set forth to illustrate, but are not to be construed to limit the present invention.

MODE FOR THE INVENTION

A better understanding of a method of producing an organic compound represented by Formula 1 and the Preparation of an organic light emitting device using the same may be obtained in light of the following preparation examples and examples which are set forth to illustrate, but are not to be construed to limit the present invention.

In order to produce the compound expressed by Formula 1, any one of the compounds of the following Formulae, a to g, may be used as a starting material.

[Formula a]

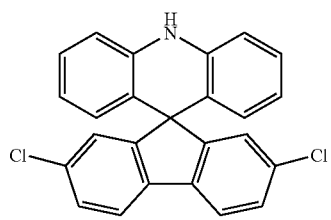

-continued

[Formula b]

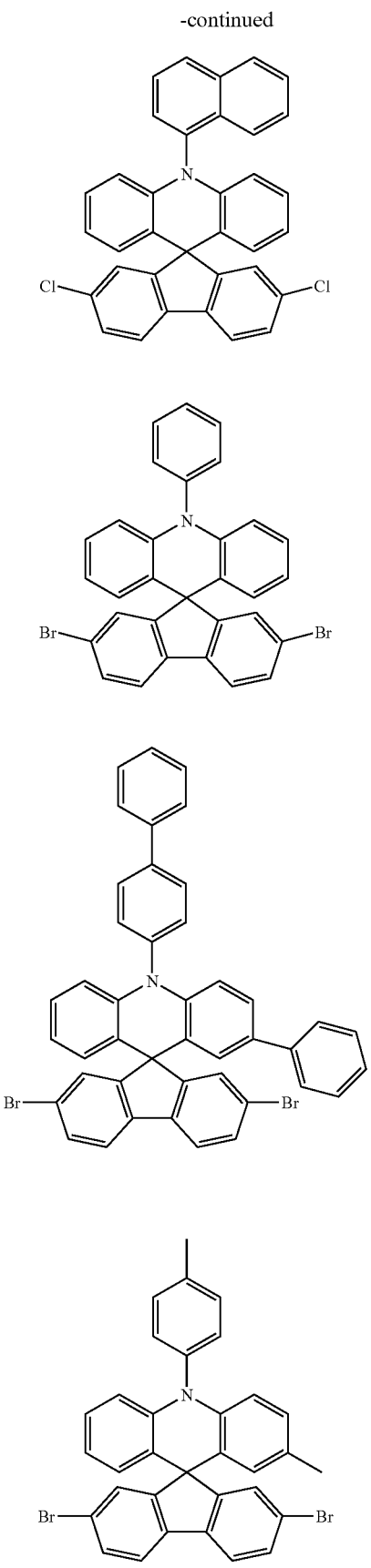

[Formula c]

[Formula d]

[Formula e]

-continued

[Formula f]

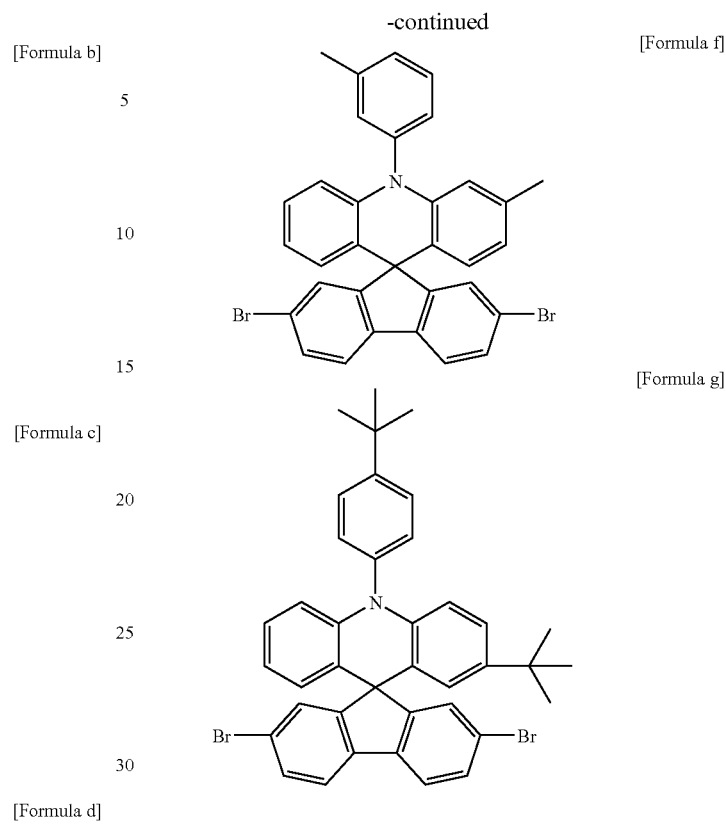

[Formula g]

PREPARATION EXAMPLE 1

Preparation of a Starting Material Represented by Formula a

After 10 g of diphenylamine (59 mmol) and 8.04 ml of bromomethyl methyl ether (88.6 mmol) were dissolved in 100 ml of tetrahydrofuran, 12.4 ml of tri-ethylamine (88.6 mmol) were added thereto. Stirring was conducted in a nitrogen current for 5 hours, and an organic layer was then extracted using distilled water. The extracted organic layer was subjected to a column separation process at a ratio of n-hexane/tetrahydrofuran of 15:1, and vacuum dried to produce 12 g of tertiary amine (yield 90%).

2) The amine compound produced in 1) (12.0 g, 56.3 mmol) was dissolved in 100 ml of purified THF and cooled to −78° C., and n-BuLi (2.5 M hexane solution, 22.5 ml, 56.3 mmol) was slowly added thereon. Stirring was conducted at the same temperature for 30 min, and a 2,7-dichloro-9-fluorenone compound (14.0 g, 56.3 mmol) was added thereto. After stirring was conducted at the same temperature for 40 min, the temperature was raised to normal temperature and stirring was carried out for an additional 3 hours. The reaction was completed in an ammonium chloride aqueous solution, and extraction was conducted with ethyl ether. Water was removed from an organic material layer using anhydrous magnesium sulfate, and an organic solvent was then removed therefrom. The produced solid was dispersed in ethanol, stirred for one day, filtered, and vacuum dried. After an intermediate material was dispersed in 100 ml of acetic acid, ten drops of concentrated sulfuric acid were dropped thereto and reflux was conducted for 4 hours. The resulting solid was filtered, washed with ethanol, and vacuum dried to produce 21.8 g of amine (96.8% yield). MS: [M+H]+=401.

PREPARATION EXAMPLE 2

Preparation of a Starting Material Represented by Formula b

A compound of Formula a (9.00 g, 22.5 mmol), 1-iodonaphthalene (11.4 g, 45.0 mmol), potassium carbonate (6.22 g, 45.0 mmol), copper iodide (214 mg, 1.13 mmol), and xylene (250 ml) were heated in a nitrogen atmosphere overnight. After cooling to normal temperature, a product was extracted with ethyl acetate, water was removed with anhydrous magnesium sulfate, and the solvent was removed at a reduced pressure. The resulting product was passed through a silica gel column using a hexane solvent to produce a compound, the solvent was removed at a reduced pressure, and vacuum drying was conducted to produce the compound of Formula b (5.0 g, 42% yield). MS: $[M+H]^+=527$.

PREPARATION EXAMPLE 3

Preparation of a Starting Material Represented by Formula c 1) 5.08 ml of diphenylamine (30 mmol), 5.6 ml of 1-bromo-2-iodobenzene (45 mmol), 2.29 g of copper (36 mmol), and 4.98 g of potassium carbonate (36 mmol) were refluxed for 5 days. After cooling, extraction was conducted with water and ethyl acetate, water was removed with anhydrous magnesium sulfate, and a column separation process was conducted using n-hexane. Ethanol was added to achieve solidification, thereby creating 4.4 g of product (45% yield). MS: $[M+H]^+=323$.

2) 1.36 g of compound produced in 1) (4.19 mmol) were dissolved in 15 ml of THF in a dried flask, and a dry ice/acetone bath was provided therein. 6.18 ml (2.5 eq) of t-butyllithium (1.7 M pentane solution) were dropped thereon for 30 min and stirring was conducted for an additional 1 hour. 1.18 g of 2,7-dibromo-9-fluorenone (3.49 mmol) were dissolved in 20 ml of THF and then injected using a syringe into a reaction solution, and stirring was conducted for an additional 1 hour. After a further stirring at normal temperature for the additional 1 hour, a saturated $NH_4Cl$ aqueous solution was added thereto and then stirred for 30 min. Extraction was conducted with water and ethyl acetate, water was removed with anhydrous magnesium sulfate, and vacuum drying was carried out to create a product.

3) The unpurified compound produced in 2) was dissolved in 5 ml of acetic acid, 5 drops of concentrated sulfuric acid were added therein, and stirring was conducted at 60° C. for one day. After cooling, with filtration washing was conducted using water and a 5% $NaHCO_3$ aqueous solution, and then a column separation process was conducted using a solution of n-hexane and ethyl acetate at a ratio of 9:1. Ethanol was added to the resulting substance to achieve solidification, filtration was conducted, and vacuum drying was conducted to create 1.76 g of product (89.2%). MS: $[M+H]^+=566$.

PREPARATION EXAMPLE 4

Preparation of a Starting Material Represented by Formula d 1) 2.0 g of 4-aminobiphenyl (12 mmol) and 2.74 g of 4-bromobiphenyl (12.0 mmol) were dissolved in 50 ml of xylene, 1.72 g of sodium tert-butoxide (18 mmol), 0.11 g of tris(dibenzylideneacetone)dipalladium(0) (0.12 mmol), and 0.036 g of tri-tert-butylphosphine (0.18 mmol) were added thereto, and reflux was conducted in a nitrogen current for 3 hours. Distilled water was added in a reaction solution to complete a reaction, an organic layer was extracted, and water was removed with anhydrous magnesium sulfate. The solvent was removed at a reduced pressure, recrystallization was conducted using hexane, and vacuum drying was conducted to create 2.2 g of product (57% yield). MS: $[M+H]^+=322$.

2) 2.2 g of compound produced in 1) (6.8 mmol), 1.25 ml of 1-bromo-2-iodobenzene (10 mmol), 1.2 g of potassium carbonate (8.8 mmol) and 0.56 g of copper (8.8 mmol) were refluxed in 5 ml of nitrobenzene in a nitrogen atmosphere for 30 hours, and then cooled to normal temperature. THF was added thereto, stirring was conducted for 30 min, an insoluble solid was filtered and thus removed, and the solvent was removed at a reduced pressure. A column separation process was conducted at a ratio of n-hexane/toluene of 3:1, recrystallization was conducted using ethanol, and vacuum drying was conducted to produce 2.4 g of compound (yield 74%). MS: $[M+H]^+=477$.

3) 2.30 g of compound produced in 2) (4.83 mmol) were dissolved in 30 ml of THF, and 5.68 ml (9.66 mmol) of t-BuLi (1.7 M pentane solution) were dropped thereon at −78° C. for 30 min. After stirring was conducted for 2 hours, 1.36 g of 2,7-dibromo-9-fluorenone compound (4.03 mmol), dissolved in 8 ml of THF, were added thereto. After stirring at the same temperature for 2 hours, a cooling bath (dry ice/acetone) was removed and stirring was conducted at normal temperature for 1 hour. 16 ml of saturated ammonium chloride aqueous solution were added thereto and stirring was conducted for 30 min to complete a reaction. A product was extracted with ethyl acetate and solidification was achieved using ethanol to produce a compound. The compound was vacuum dried and then dissolved in 5 ml of acetic acid, 5 drops of concentrated sulfuric acid solution were added thereto, and stirring was conducted at 60° C. overnight. After cooling to normal temperature, a solvent was removed at a reduced pressure and an organic layer was extracted with ethyl acetate. Byproducts contained in the product were removed through a column separation process using n-hexane and tetrahydrofuran at a ratio of 4:1. The product was recrystallized with ethanol and vacuum dried to create 0.77 g of product (27%). MS: $[M+H]^+=718$.

PREPARATION EXAMPLE 5

Preparation of a Starting Material Represented by Formula e 1) 1.97 g of 4,4-ditolylamine (10 mmol), 1.87 ml of 1-bromo-2-iodobenzene (15 mmol), 95 mg of copper iodide (0.5 mmol), and 4.15 g of potassium carbonate (30 mmol) were added to 100 ml of xylene and refluxed for 1 week. After cooling, water was added thereto, extraction was conducted with ethyl acetate, water was removed with anhydrous magnesium sulfate, and a column separation process was conducted using only n-hexane to create 2.219 g of product (yield 63%). MS: $[M]^+=353$.

2) The resulting compound (428 mg, 1.21 mmol) was dissolved in 6 ml of purified THF in a dried flask and a dry ice/acetone bath was provided therein. 1.43 ml of t-BuLi (1.7 M pentane solution, 2.43 mmol) were dropped thereon for 30 min and stirring was conducted at the same temperature for an additional 1 hour. A 2,7-dibromo-9-fluorenone compound (338 mg, 1.00 mmol) was dissolved in 6 ml of THF and then injected using a syringe into a reaction solution, and stirring was conducted for an additional 1 hour. After the stirring at normal temperature for the additional 1 hour, a saturated ammonium chloride aqueous solution was added thereto to complete the reaction, and then stirring was conducted for 30 min. Extraction was conducted with ethyl acetate, water was removed with anhydrous magnesium sulfate, and vacuum drying was carried out.

3) The compound produced in 2) was dissolved in 5 ml of acetic acid, 5 drops of concentrated sulfuric acid were loaded thereon, and stirring was conducted at 60° C. for one day. After cooling to normal temperature, washing with filtration was conducted using water and a 5% sodium bicarbonate aqueous solution, and a column separation process was conducted using a solution of n-hexane and tetrahydrofuran at a ratio of 9:1. Ethanol was used to achieve solidification, and filtration and drying were conducted (528 mg, yield 89%). MS: $[M+H]^+$=594.

PREPARATION EXAMPLE 6

Preparation of a Starting Material Represented by Formula f 1) 2.28 ml of m,m'-ditolylamine (12 mmol), 2.26 ml of 1-bromo-2-iodobenzene (18.0 mmol), 991 mg of copper (1.3 eq), 2.16 g of potassium carbonate (15.6 mmol), and 1 ml of nitrobenzene were refluxed for 3 days. After cooling, nitrobenzene was distilled at a reduced pressure and thus removed, extraction was conducted with water and ethyl acetate, and water was removed from an organic layer using anhydrous magnesium sulfate. After the organic solvent was removed, a column separation process was conducted using a solvent of n-hexane and ethyl acetate at a ratio of 50:1, and ethanol was used to achieve solidification. MS: $[M+H]^+$=353 (—Br), 400 (—I).

Yield: 68% (2.9 g).

2) 779 mg of compound produced in 1) (2.21 mmol) were dissolved in 8 ml of purified THF in a dried flask, and a dry ice/acetone bath was provided therein. 2.6 ml (4.4 mmol) of t-butyllithium (1.7 M pentane solution) were dropped thereon for 30 min and further stirring was conducted for an additional 1 hour. 0.622 g of 2,7-dibromo-9-fluorenone (1.83 mmol) were dissolved in 9 ml of THF and then injected using a syringe into a reaction solution, and stirring was conducted at the same temperature for an additional 1 hour. After the stirring at normal temperature for the additional 1 hour, a saturated ammonium chloride aqueous solution was added thereto and then stirred for 30 min. Extraction was conducted with water and ethyl acetate, water was removed from an organic layer using anhydrous magnesium sulfate, and vacuum drying was carried out.

3) The unpurified compound produced in 2) was dissolved in 5 ml of acetic acid, 5 drops of concentrated sulfuric acid were added thereto, and stirring was conducted at 60° C. for one day. After cooling, washing was conducted during filtration using water and a 5% $NaHCO_3$ aqueous solution, and a column separation process was conducted using a solution of n-hexane and ethyl acetate at a ratio of 9:1. Ethanol was used for solidification, and filtration and vacuum drying were conducted. MS: $[M+H]^+$=594.

Yield: 73.9% (0.807 g).

PREPARATION EXAMPLE 7

Preparation of a Starting Material Represented by Formula g 1) 2-bromoaniline (800 mg, 4.70 mmol), 1-tert-butyl-4-iodobenzene (1 ml, 5.64 mmol), potassium hydroxide (1.06 g, 18.8 mmol), copper chloride (19 mg, 0.16 mmol), 1,10-phenanthroline (34 mg, 0.16 mmol), and xylene (16 ml) were heated in a nitrogen atmosphere overnight. After the resulting reactants were cooled to normal temperature, a product was extracted with ethyl acetate, water was removed with anhydrous magnesium sulfate, and the solvent was removed at a reduced pressure. The resulting product was passed through a silica gel column using a hexane solvent to produce secondary amine and tertiary amine. A mixture of secondary amine and tertiary amine was vacuum dried, added to toluene (15 ml) along with 1-tert-butyl-4-iodobenzene (0.8 mL, 4.42 mmol), copper iodide (35 mg, 0.18 mmol), and potassium carbonate (763 mg, 5.52 mmol), and heated in a nitrogen atmosphere overnight. They were cooled to normal temperature and extracted with ethyl acetate, water was removed with anhydrous magnesium sulfate, and the solvent was removed at a reduced pressure. The product was passed through a silica gel column using a hexane solvent, the solvent was removed at a reduced pressure, and vacuum drying was conducted to produce a desired white solid (0.67 g, 33%). MS: $[M+H]^+$=437.

2) 0.5 g of compound produced in 1) (1.2 mmol) were dissolved in 6 ml of purified THF in a dried flask, and a dry ice/acetone bath was provided therein. t-BuLi (1.7 M pentane solution, 1.35 ml, 2.3 mmol) was dropped thereon at −78° C. for 30 min. After the reactants were stirred for 1 hour, 338 mg of 2,7-dibromo-9-fluorenone (1 mmol) were dissolved in 5 ml of THF and then injected using a syringe into a reaction solution, and stirring was conducted at the same temperature for 1 hour. A dry ice/acetone bath was removed and stirring was conducted at normal temperature for 1 hour. Saturated ammonium chloride aqueous solution (10 ml) was added thereto and stirring was conducted for 30 min to complete a reaction. The resulting product was extracted with ethyl acetate and a column separation process was conducted using a solvent of n-hexane and ethyl acetate at a ratio of 9:1 to produce a compound.

3) The compound produced in 2) was vacuum dried and dissolved in acetic acid (5 ml), a concentrated sulfuric acid solution (3 drops) was added thereto, and stirring was conducted at 60° C. for one day. After the reactants were cooled to normal temperature, a product was filtered using a filter paper and washed with water. Byproducts contained in the product were removed through a column separation process using a solvent of n-hexane and ethyl acetate at a ratio of 9:1, and vacuum drying was conducted to create 0.31 g of product (yield 36%). MS: $[M+H]^+$=678.

EXAMPLE 1

Preparation of the Compound Represented by Formula 2-1

After 5.02 g of the compound of Formula c (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 2-1 (5.2 g, yield 78.9%). MS: $[M+H]^+$=742.

EXAMPLE 2

Preparation of the Compound Represented by Formula 3-1

After 4.68 g of compound of Formula b (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 3-1 (5.1 g, yield 72.5%). MS: $[M+H]^+=793$.

EXAMPLE 3

Preparation of the Compound Represented by Formula 3-2

After 4.68 g of the compound of Formula b (8.88 mmol) and 2.34 g of N-phenyl-1-naphthylamine (10.7 mmol) were dissolved in 120 ml of toluene, 2.90 g of sodium-tert-butoxide (30.2 mmol), 0.12 g of bis(dibenzylidene acetone)palladium (0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 3-2 (5.6 g, yield 71%). MS: $[M+H]^+=893$.

EXAMPLE 4

Preparation of the Compound Represented by Formula 26-1

After 5.28 g of the compound of Formula e (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 26-1 (4.9 g, yield 71.7%). MS: $[M+H]^+=771$.

EXAMPLE 5

Preparation of the Compound Represented by Formula 27-1

After 5.27 g of the compound of Formula f (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 27-1 (5.0 g, yield 73%). MS: $[M+H]^+=771$.

EXAMPLE 6

Preparation of the Compound Represented by Formula 28-1

After 6.02 g of the compound of Formula g (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 28-1 (5.6 g, yield 73.8%). MS: $[M+H]^+=855$.

EXAMPLE 7

Preparation of the Compound Represented by Formula 29-1

After 6.37 g of the compound of Formula d (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, using petroleum ether, and vacuum drying was conducted to produce the compound of Formula 29-1 (6.2 g, yield 77%). MS: $[M+H]^+=895$.

EXAMPLE 8

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using nitrogen plasma under a pressure of 14 mtorr at 85 W for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

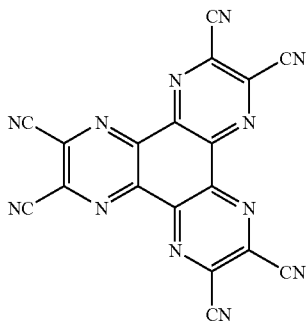

The compound of Formula 28-1 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

[Electron Transport Layer Material]

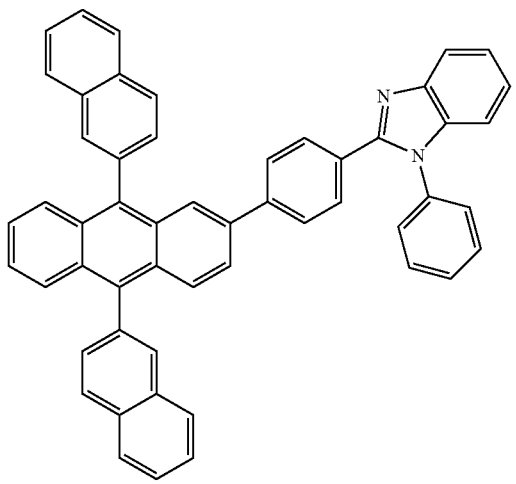

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3 \times 10^{-7}$.

The resulting device had an electric field of 5.47 V at a forward current density of 100 mA/cm², and emitted green light at a light efficiency of 2.91 lm/W. The operation and light emission of the device at the above-mentioned actuating voltage mean that the compound of Formula 28-1, which formed the layer between the hole injection layer and the light emitting layer, functions to transport holes.

EXAMPLE 9

Production of an Organic Light Emitting Device

The procedure of example 1 was repeated to produce an organic light emitting device except that a HAT thin film (80 Å: used to improve interfacial characteristics) was formed on an ITO transparent electrode which was prepared through the same procedure as example 7 and a compound of Formula 28-1 was deposited thereon to a thickness of 1100 Å to form a layer for both injecting and transporting holes.

The resulting device had an electric field of 6.75 V at a forward current density of 100 mA/cm², and emitted green light at a light efficiency of 2.19 µm/W. The operation and light emission of the device at the above-mentioned actuating voltage mean that the compound of Formula 1-4 functions to inject and transport the holes, and it can be seen that, even when the layer for bothe injecting and transporting the holes is formed using the compound of the present invention, it is possible to assure actuation at low voltage and excellent light efficiency.

EXAMPLE 10

Production of an Organic Light Emitting Device

The procedure of example 9 was repeated to produce a device except that the compound of Formula 28-1 was substituted with the compound of Formula 2-1.

The resulting device had an electric field of 5.63 V at a forward current density of 100 mA, and emitted green light at a light efficiency of 1.83 lmW.

EXAMPLE 11

Production of an Organic Light Emitting Device

The procedure of example 9 was repeated to produce a device except that the compound of Formula 28-1 was substituted with the compound of Formula 3-1.

The resulting device had an electric field of 5.77 V at a forward current density of 100 mA, and emitted green light at a light efficiency of 1.66 lm/W.

EXAMPLE 12

Production of an Organic Light Emitting Device

The procedure of example 9 was repeated to produce a device except that the compound of Formula 28-1 was substituted with the compound of Formula 3-2.

The resulting device had an electric field-of-5.72 V at a forward current density of 100 mA, and emitted green light at a light efficiency of 1.78 lm/W.

EXAMPLE 13

Production of an Organic Light Emitting Device

The procedure of example 9 was repeated to produce a device except that the compound of Formula 28-1 was substituted with the compound of Formula 26-1.

The resulting device had an electric field of 5.70 V at a forward current density of 100 mA, and emitted green light at a light efficiency of 2.1 lm/W.

EXAMPLE 14

Production of an Organic Light Emitting Device

The procedure of example 9 was repeated to produce a device except that the compound of Formula 28-1 was substituted with the compound of Formula 27-1.

The resulting device had an electric field of 5.63 V at a forward current density of 100 ma, and emitted green light at a light efficiency of 2.0 lm/W.

EXAMPLE 15

Production of an Organic Light Emitting Device

The procedure of example 9 was repeated to produce a device except that the compound of Formula 28-1 was substituted with the compound of Formula 29-1.

The resulting device had an electric field of 5.80 V at a forward current density of 100 mA, and emitted green light at a light efficiency of 11.82 lm/W.

EXAMPLE 16

Production of an Organic Light Emitting Device

The procedure of example 9 was repeated to produce a device except that the compound of Formula 28-1 was substituted with the compound of Formula 3-1.

The resulting device had an electric field of 5.77 V at a forward current density of 100 mA, and emitted green light at a light efficiency of 1.66 lm/W.

EXAMPLE 17

Production of an Organic Light Emitting Device

The procedure of example 9 was repeated to produce a device except that the compound of Formula 28-1 was substituted with the compound of Formula 3-2.

The resulting device had an electric field of 5.72 V at a forward current density of 100 mA, and emitted green light at a light efficiency of 1.78 lm/W.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:
1. An organic light emitting device, comprising:
a first electrode;
organic material layer(s) comprising a light emitting layer, wherein at least one layer of the organic material layer(s) includes the compound of Formula 1; and
a second electrode;
wherein the first electrode, the organic material layer(s), and the second electrode form a layered structure;

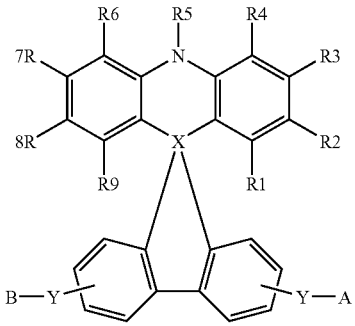

Formula 1 wherein X is C,
A is —NZ1Z2;
B is —NZ3Z4;
Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;
Z1 to Z4 are each independently hydrogen; aliphatic hydrocarbons having 1-20 carbon atoms; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having 1-20 carbon atoms or aromatic hydrocarbons having 6-20 carbon atoms; or a boron group which is substituted with aromatic hydrocarbons;
R1 to R4, and R6 to R9 are each independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, and an ester group, R1 to R4, and R6 to R9 may form aliphatic or hetero condensation rings along with adjacent groups; and
R5 is a substituted or unsubstituted aryl group or a substituted or unsubstituted heterocyclic group, and carbon at an ortho-position of the aryl or the heterocyclic group of R5 and R4 or R6 may form a condensation ring along with a group selected from the group consisting of O, S, NR, PR, C=O, CRR', and SiRR'; wherein R and R' each independently are selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group, and may form a condensation ring to form a spiro compound.

2. The organic light emitting device as set forth in claim 1, wherein carbon at the ortho-position of the aryl or the heterocyclic group of R5 and R4 or R6 form the condensation ring along with a group selected from the group consisting of O, S, NR, PR, C=O, CRR', and SiRR'.

3. The organic light emitting device as set forth in claim 1, wherein the compound of Formula 1 is any one of compounds of Formulae 2 to 119:

Formulae 2 to 119

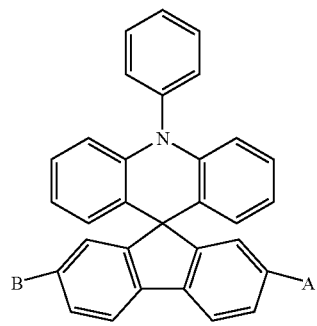

-continued

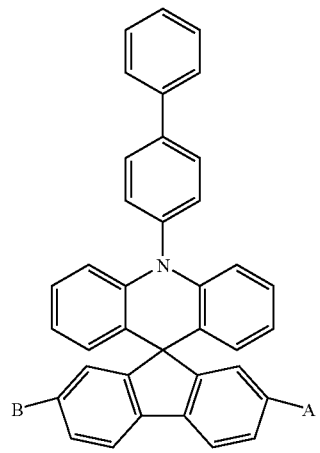

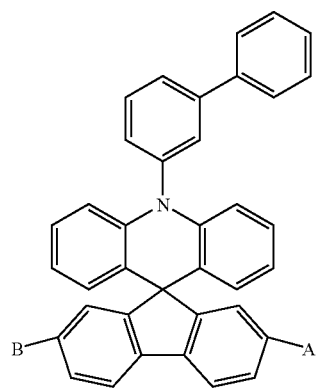

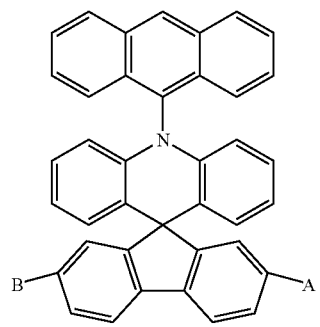

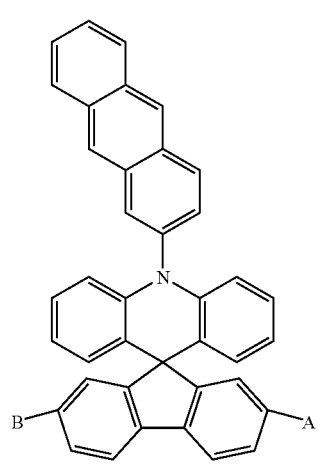

-continued
9
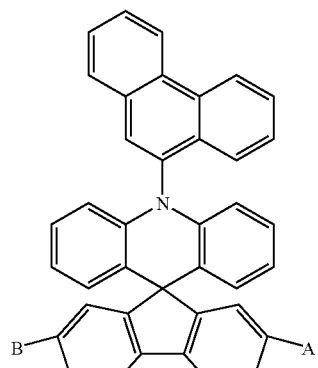
6
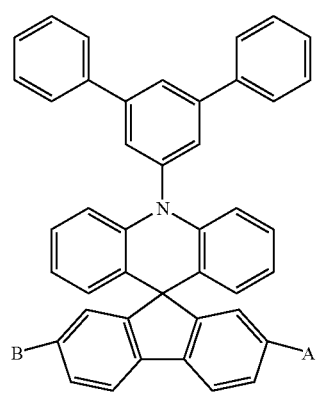
7
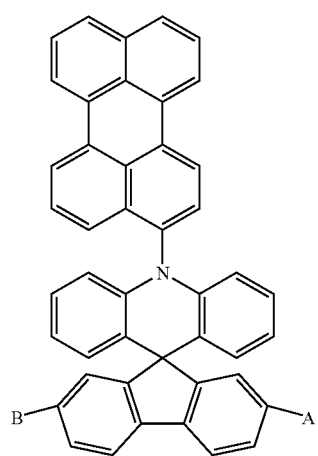
-continued
8
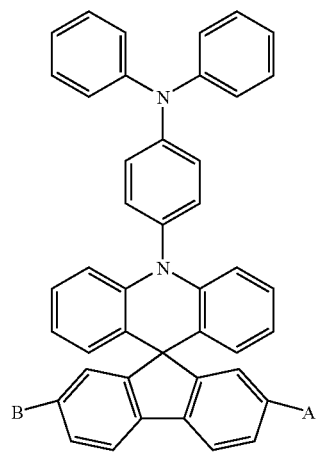
9
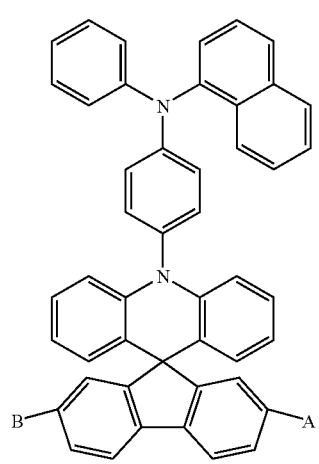
10
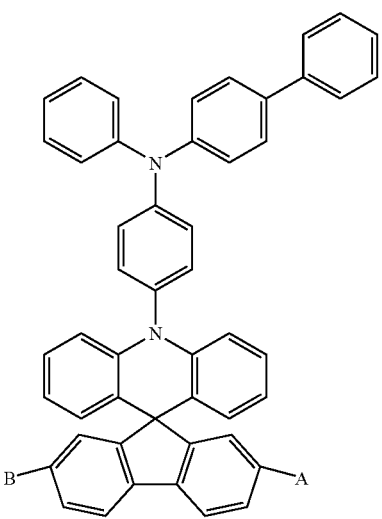

-continued
11
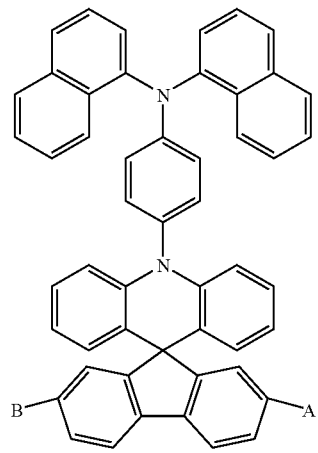
12
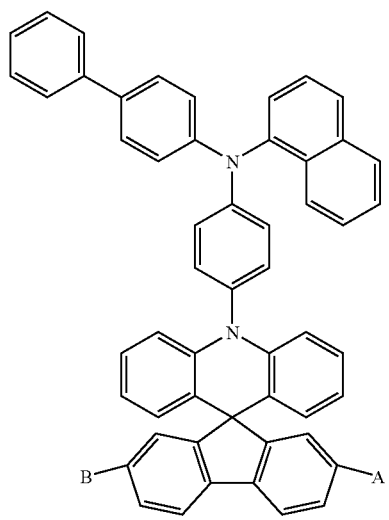
13
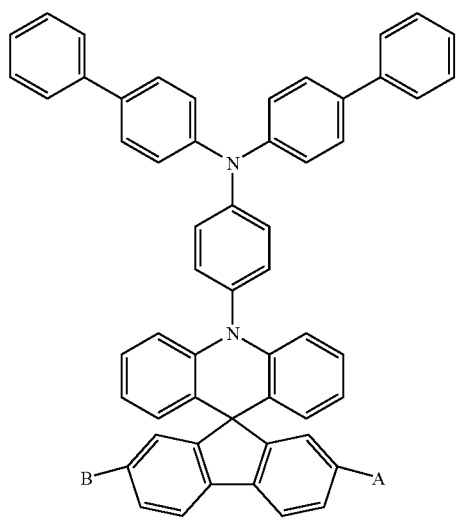
-continued
14
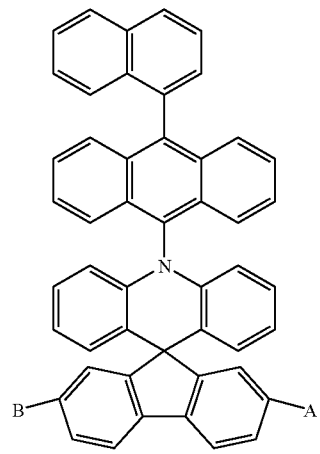
15
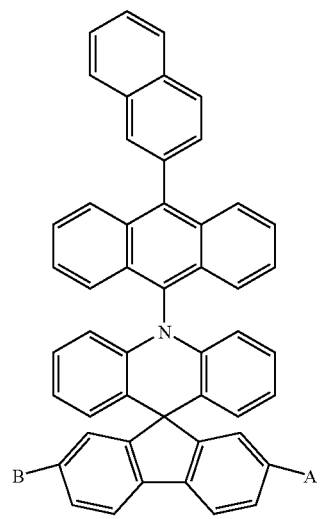
16
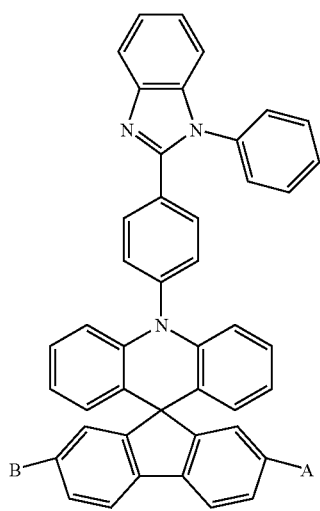

-continued
17
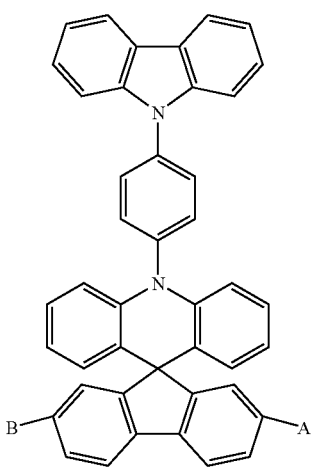
18
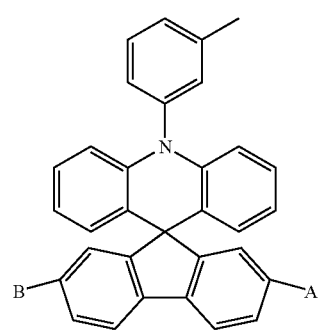
19
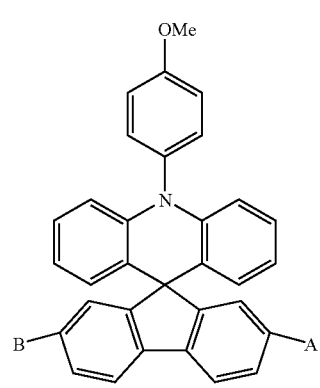
20
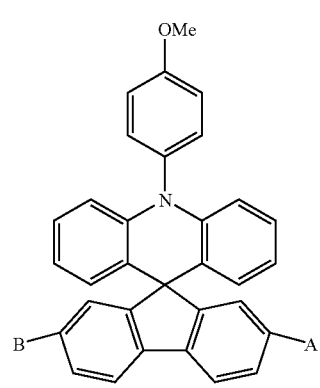
-continued
21
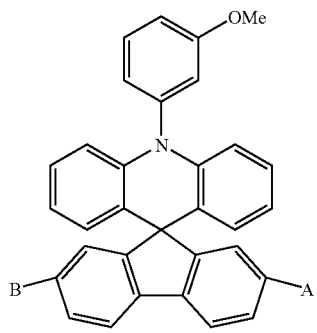
22
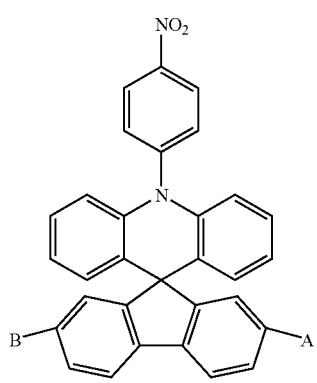
23
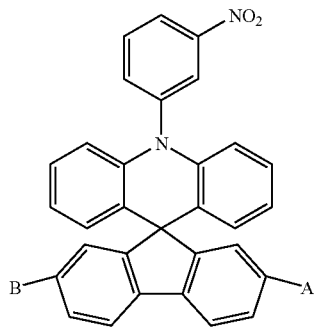
24
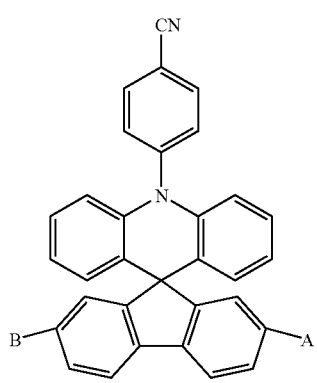

-continued
25
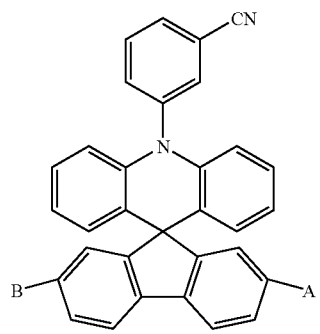
26
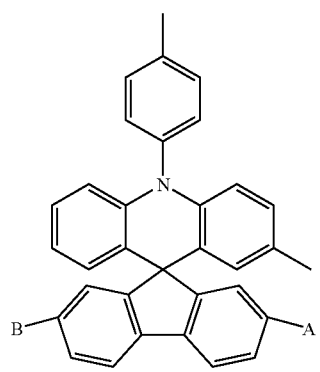
27
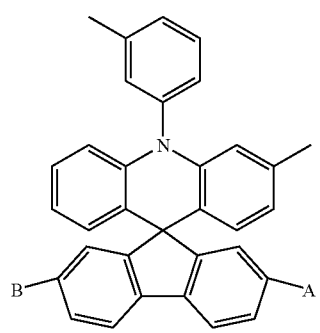
28
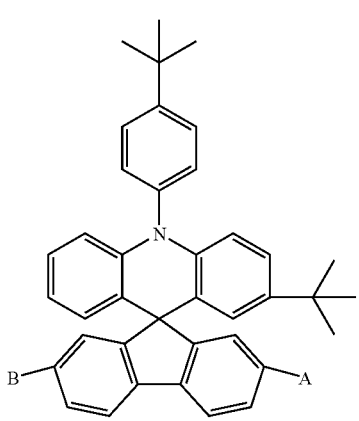
-continued
29
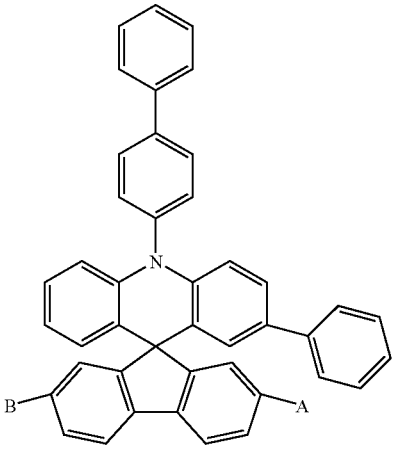
30
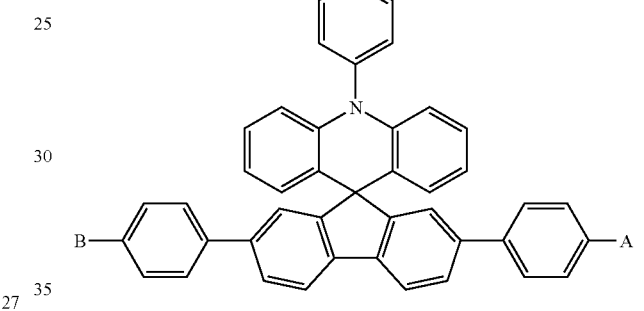
31
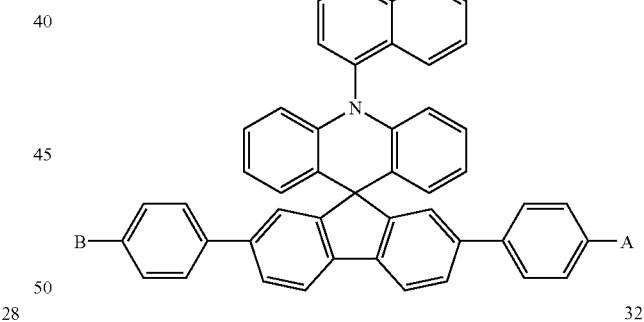
32
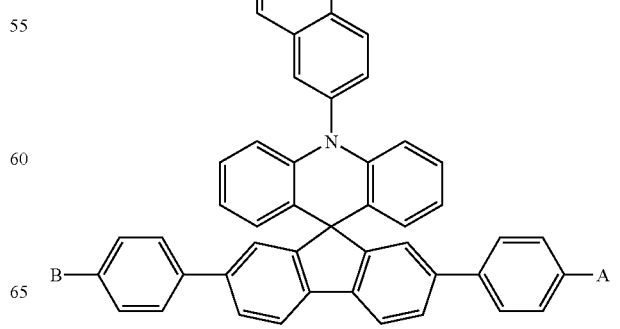

33
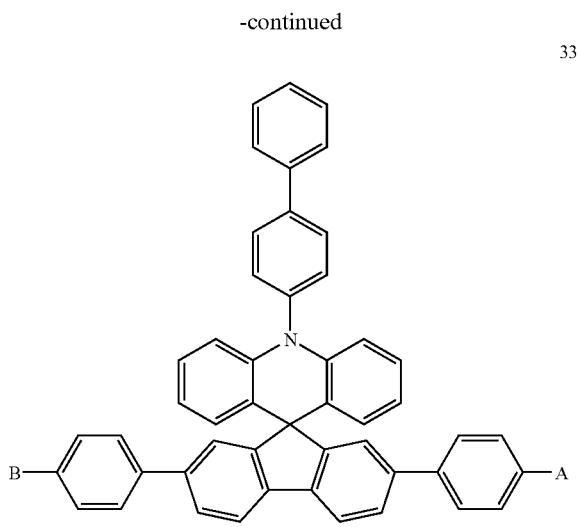
34
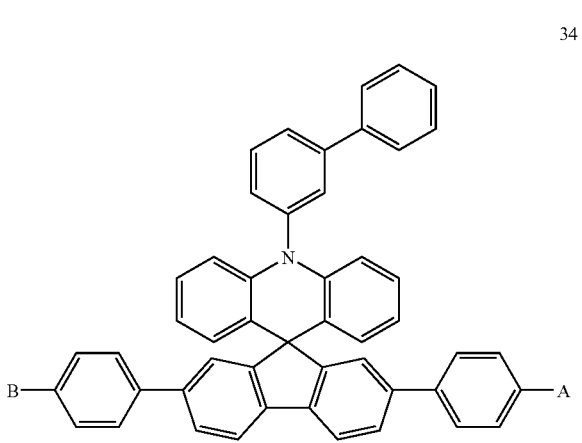
35
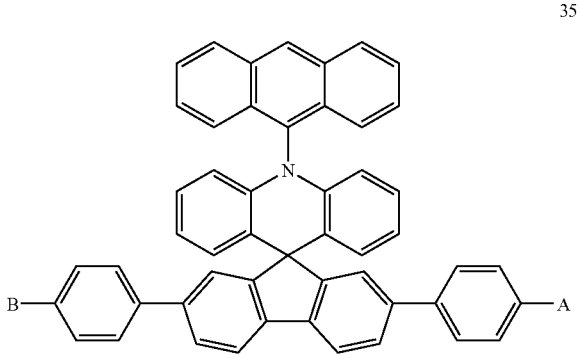
36
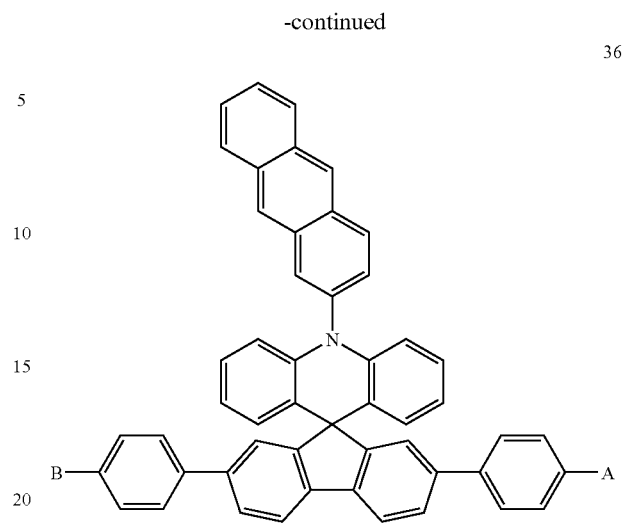
37
38
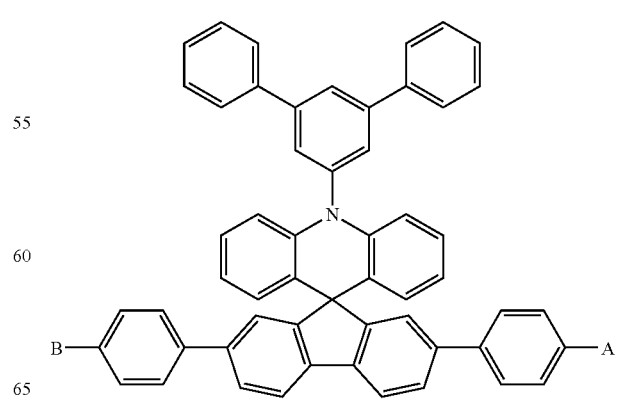

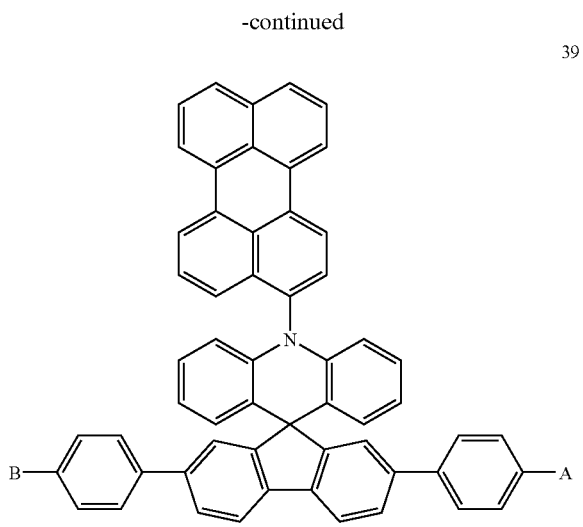
39
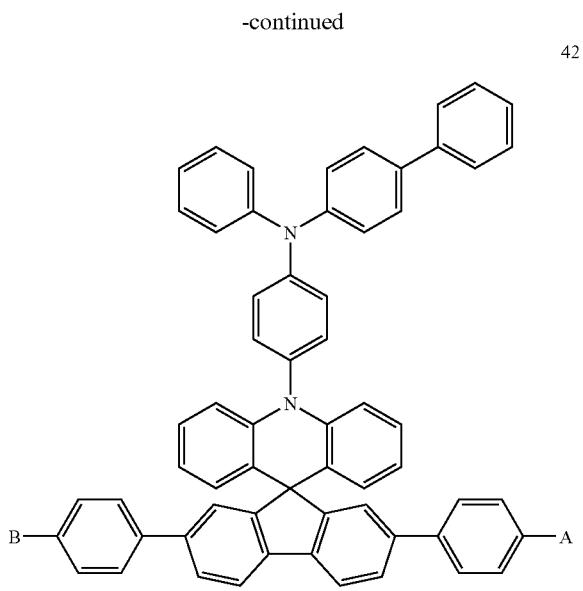
42
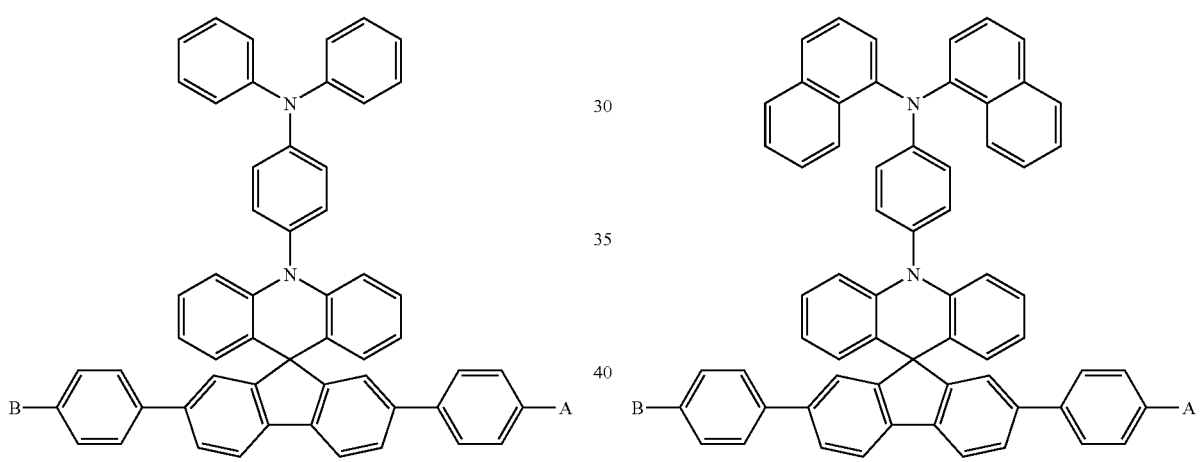
40
41
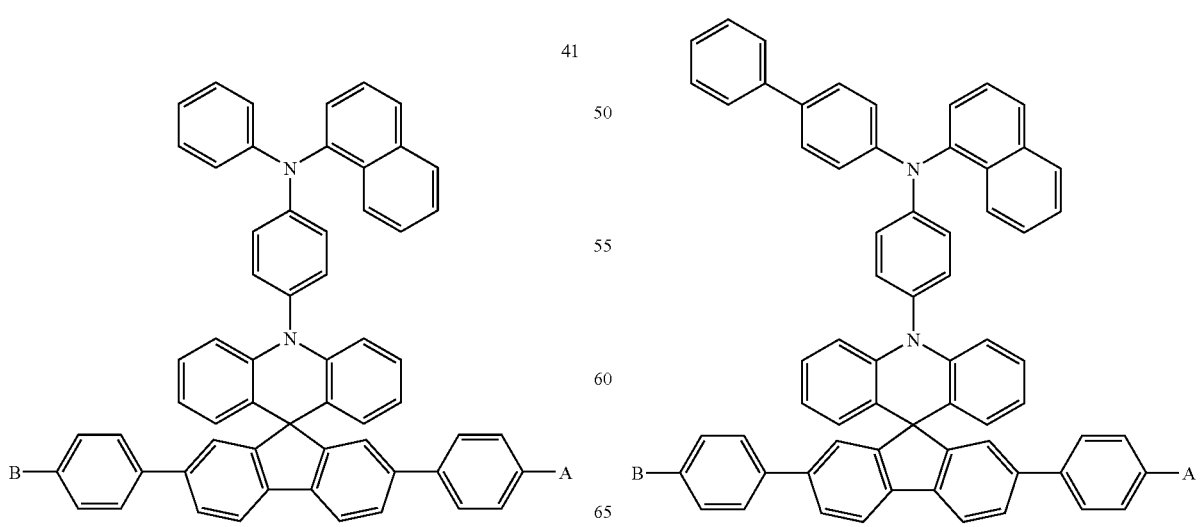
43
44

-continued
45
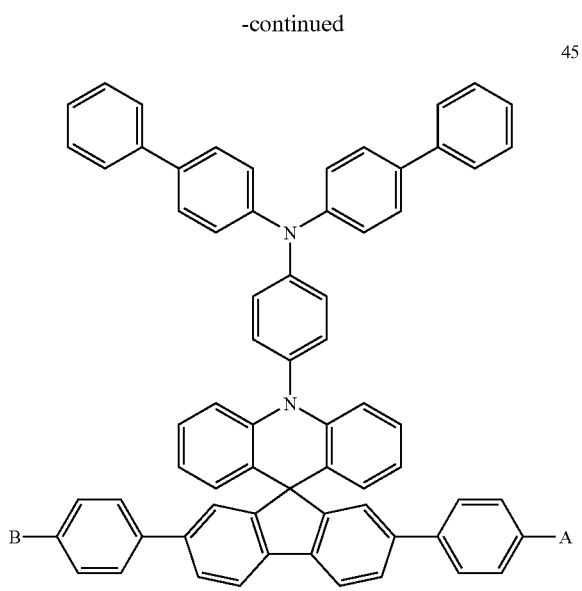
46
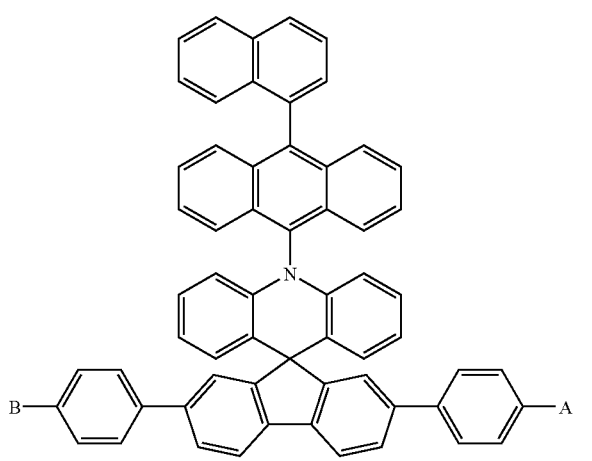
47
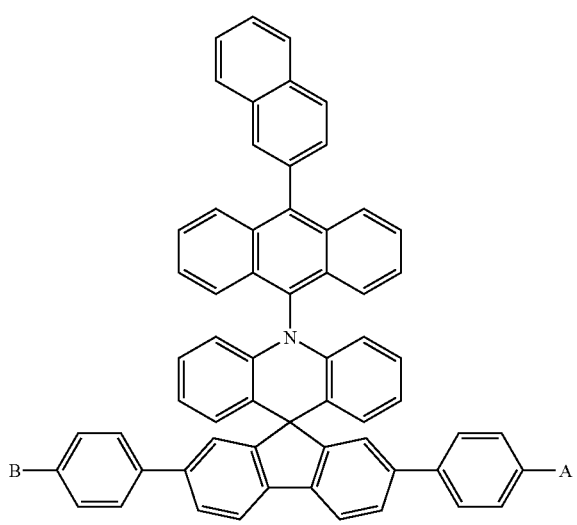
-continued
48
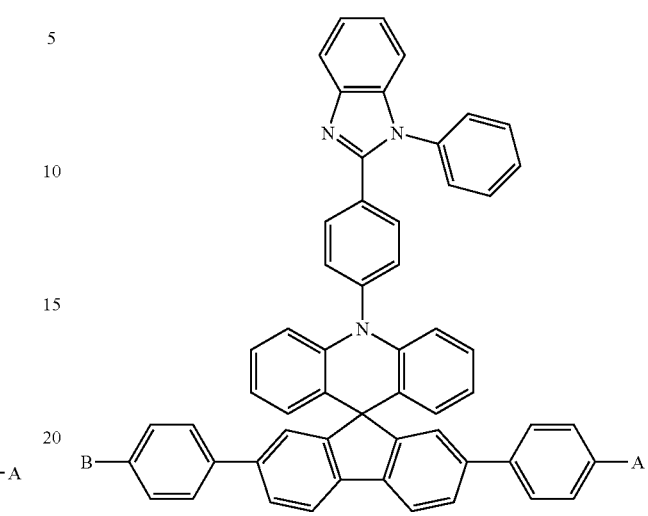
49
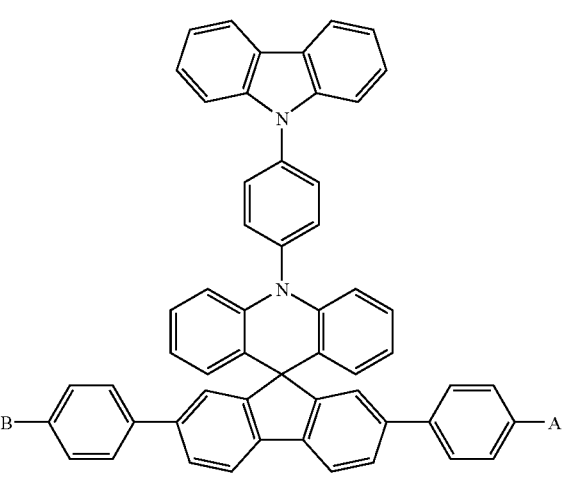
50
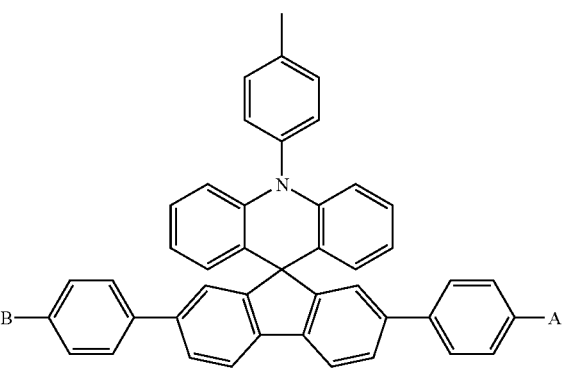

51 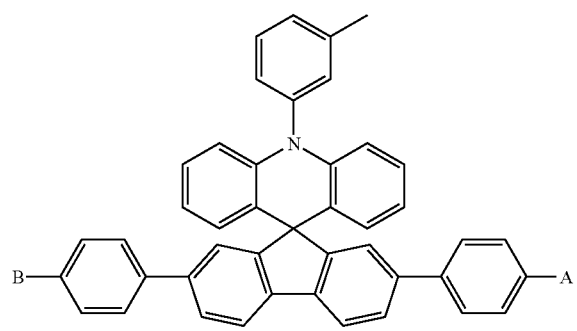
52 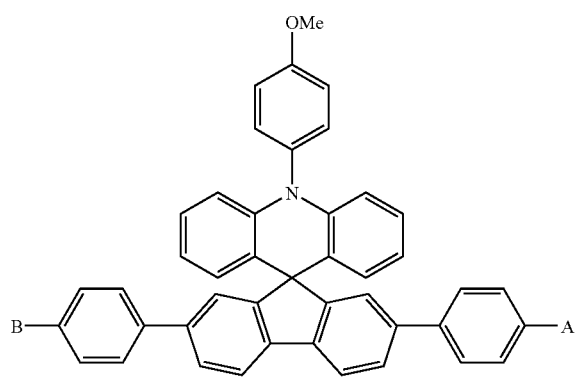
53 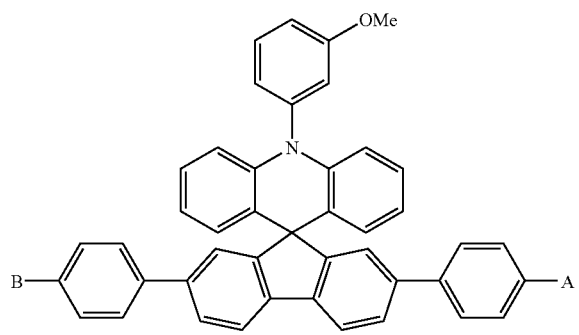
54 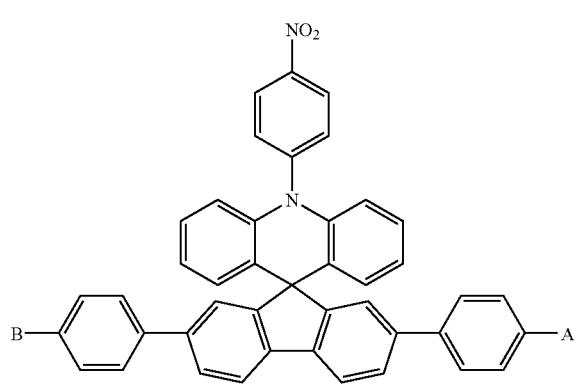
55 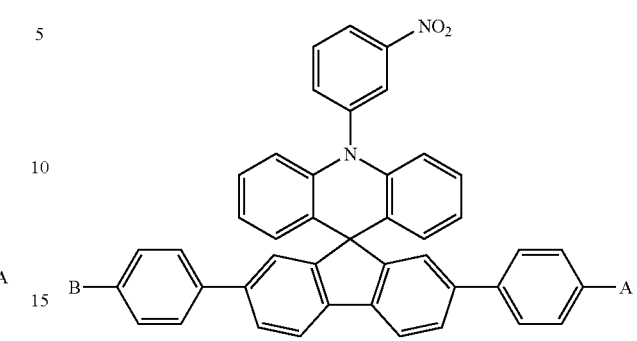
56 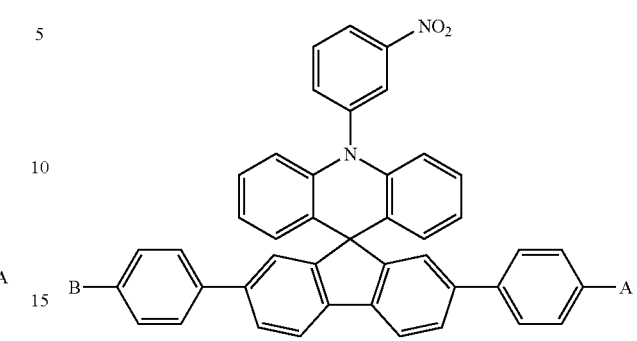
57 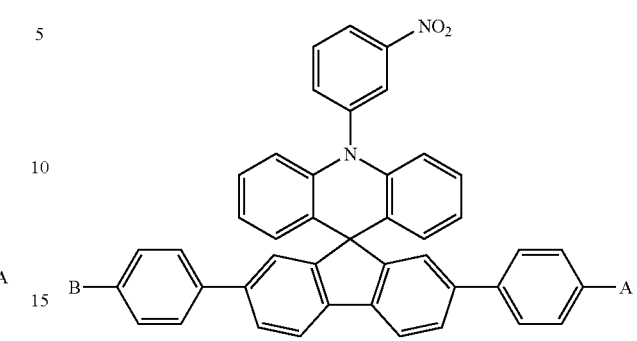
58 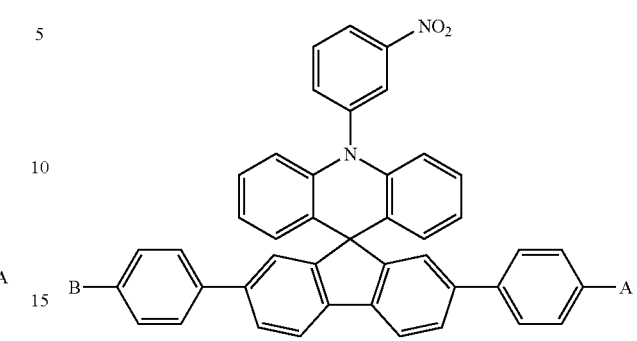

-continued
59
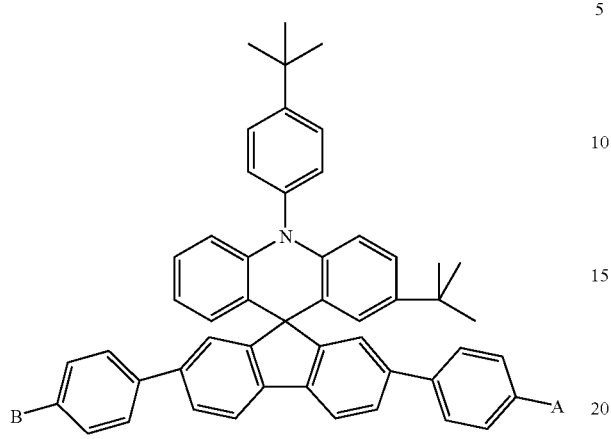
60
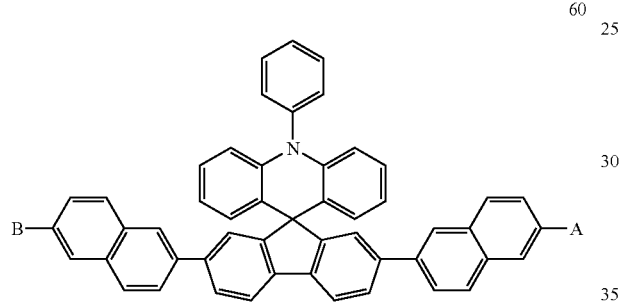
61
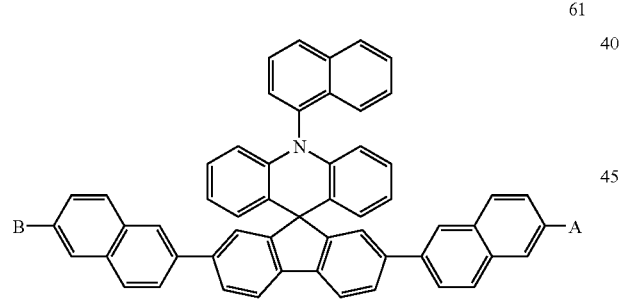
62
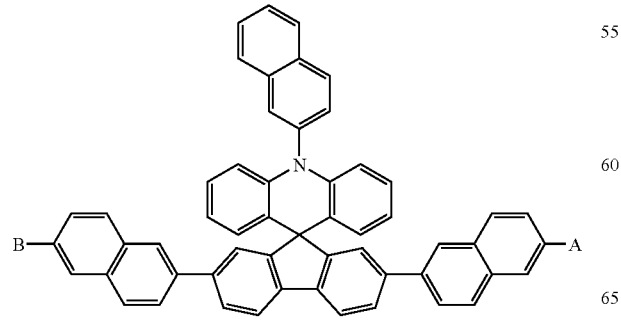
-continued
63
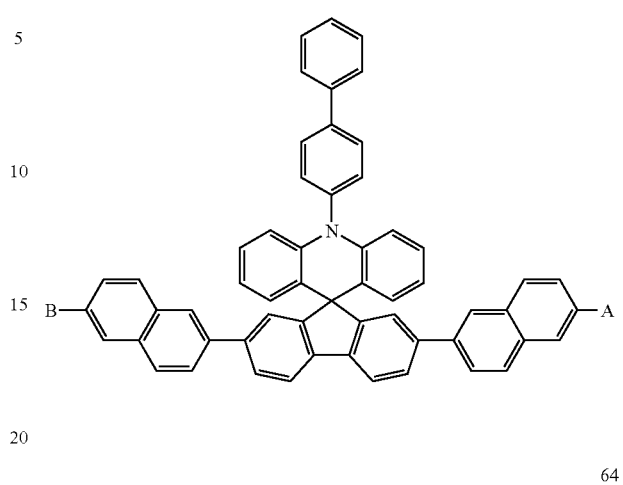
64
65
66
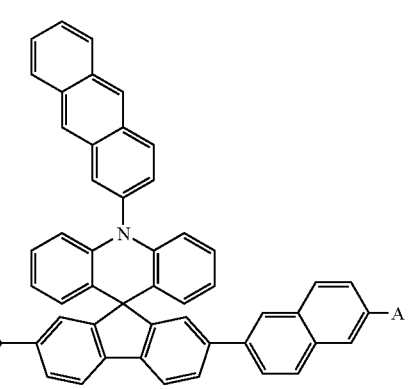

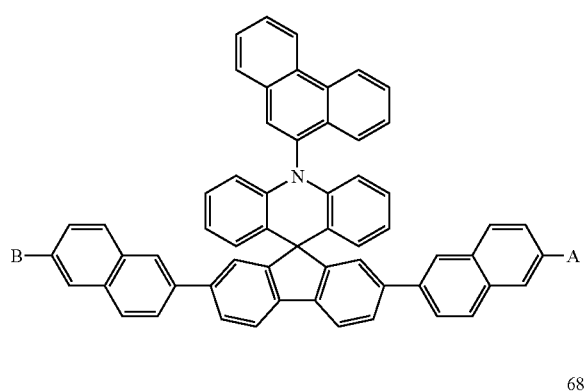
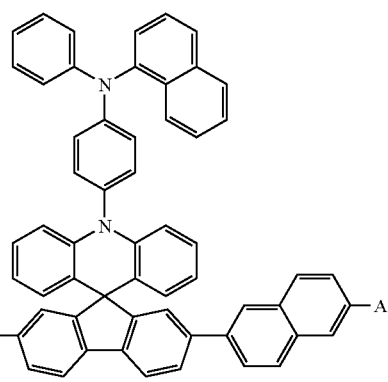
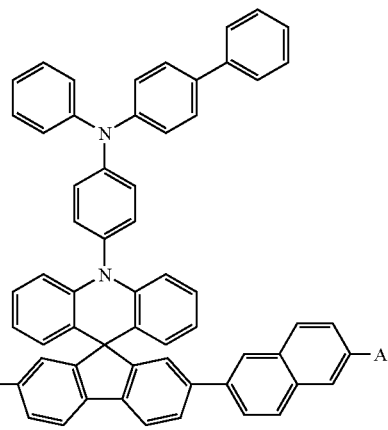
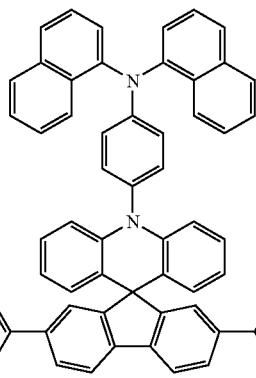

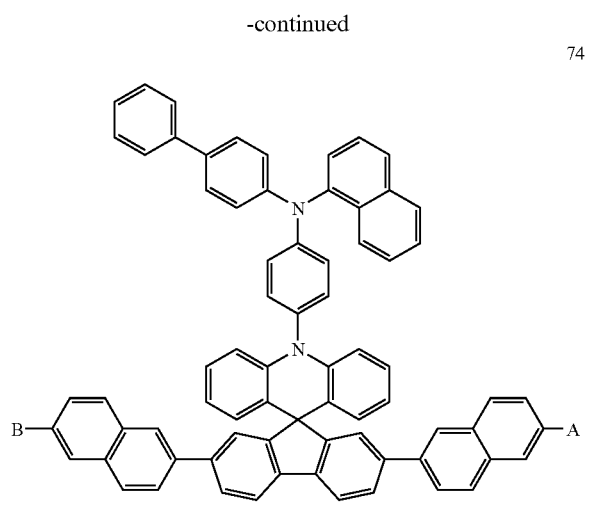
74
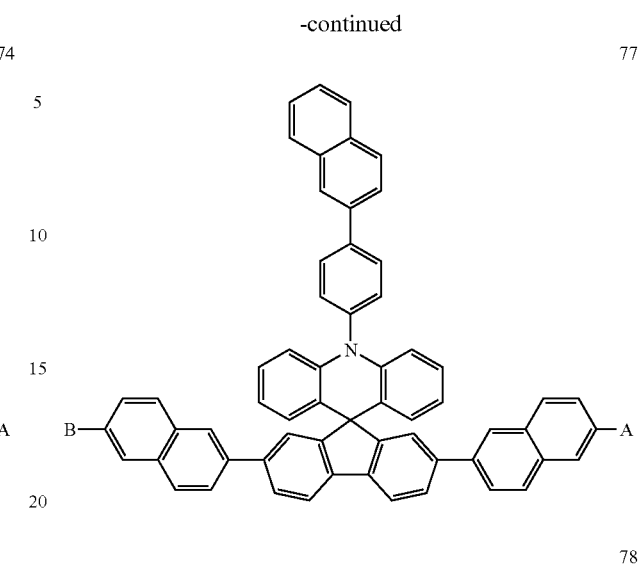
77
75
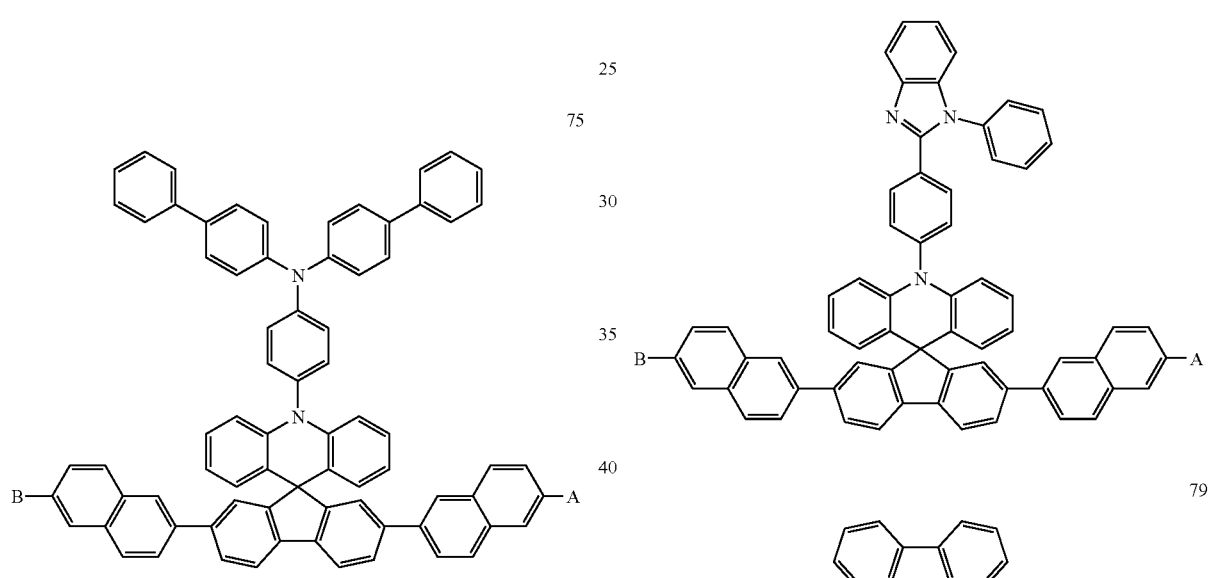
78
79
76
80
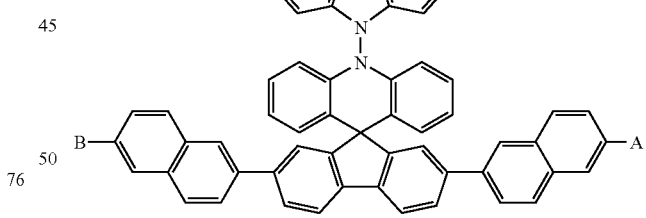
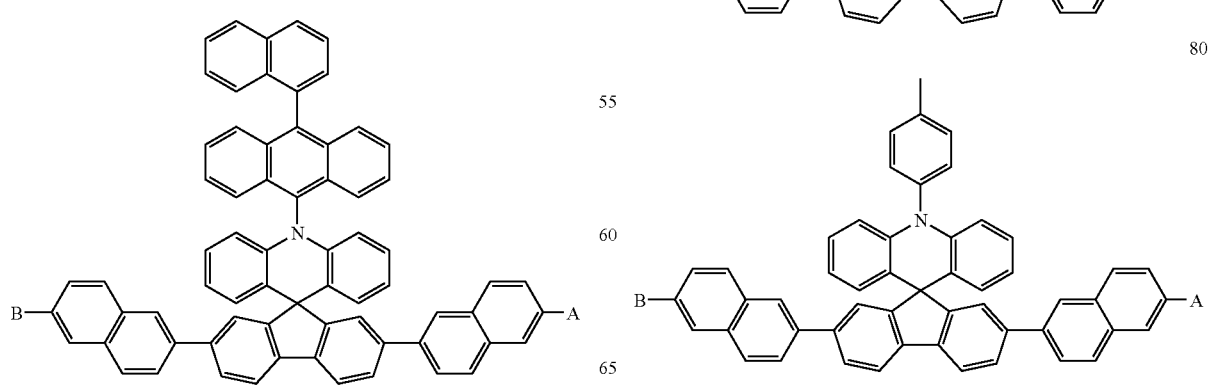

-continued
81
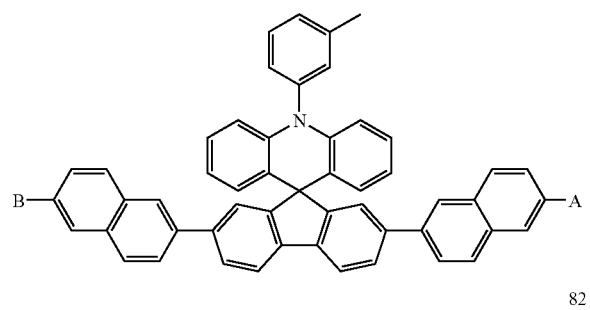
82
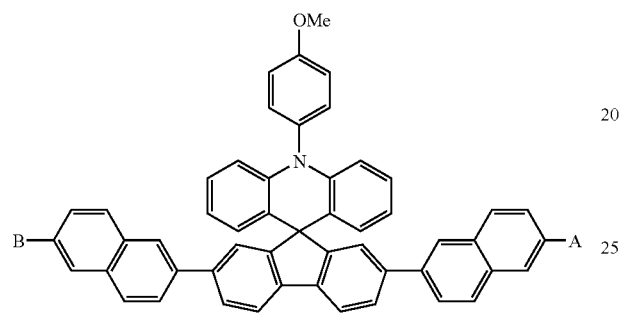
83
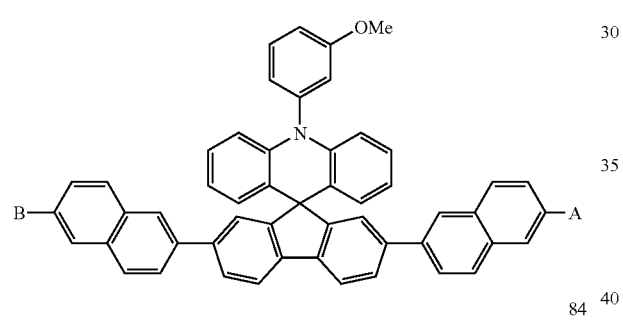
84
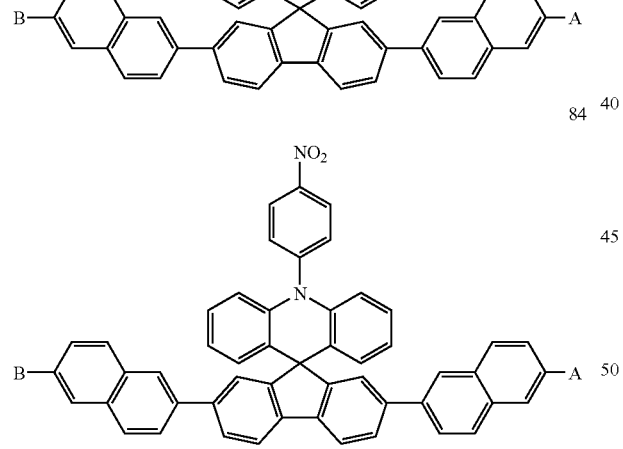
85
-continued
86
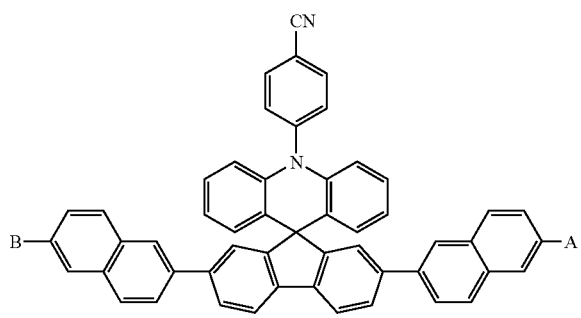
87
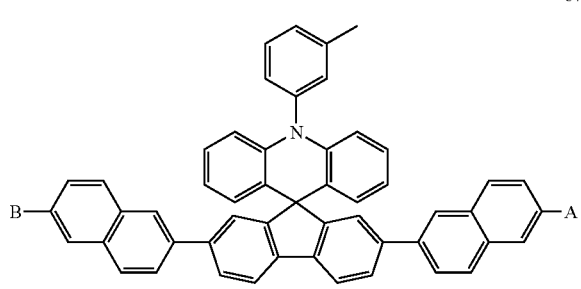
88
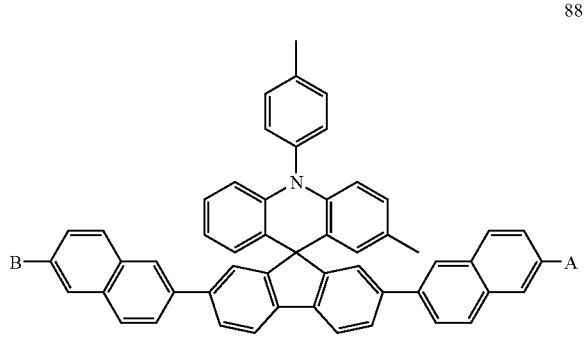
89
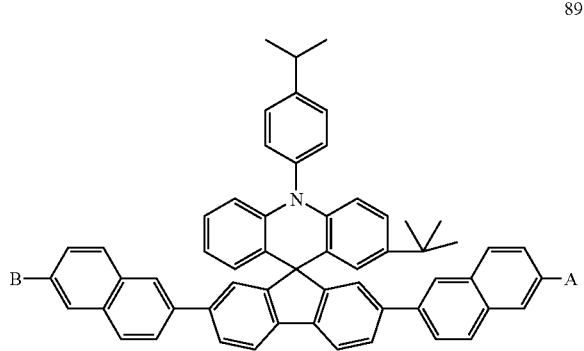

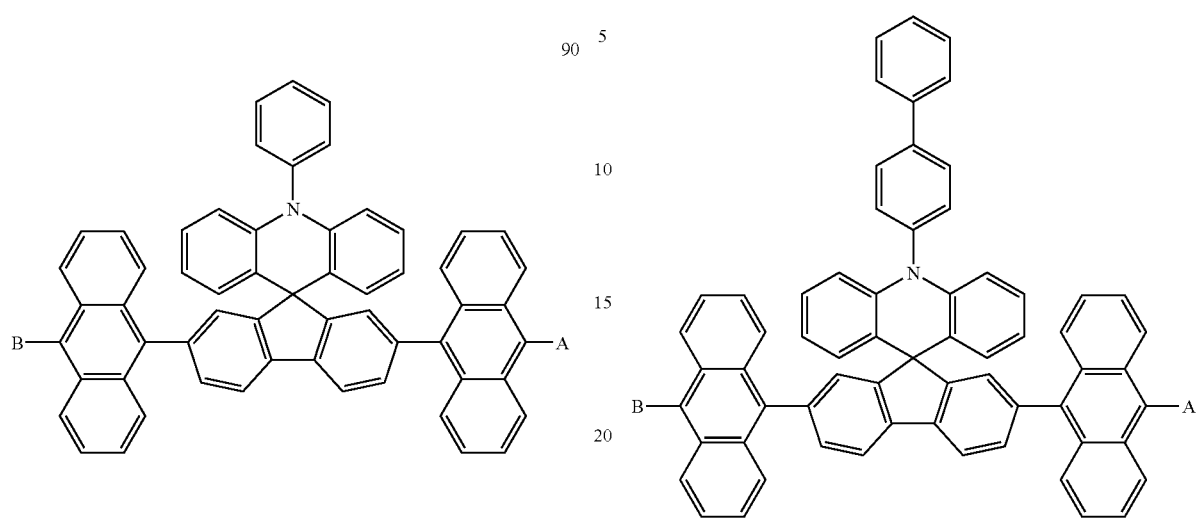
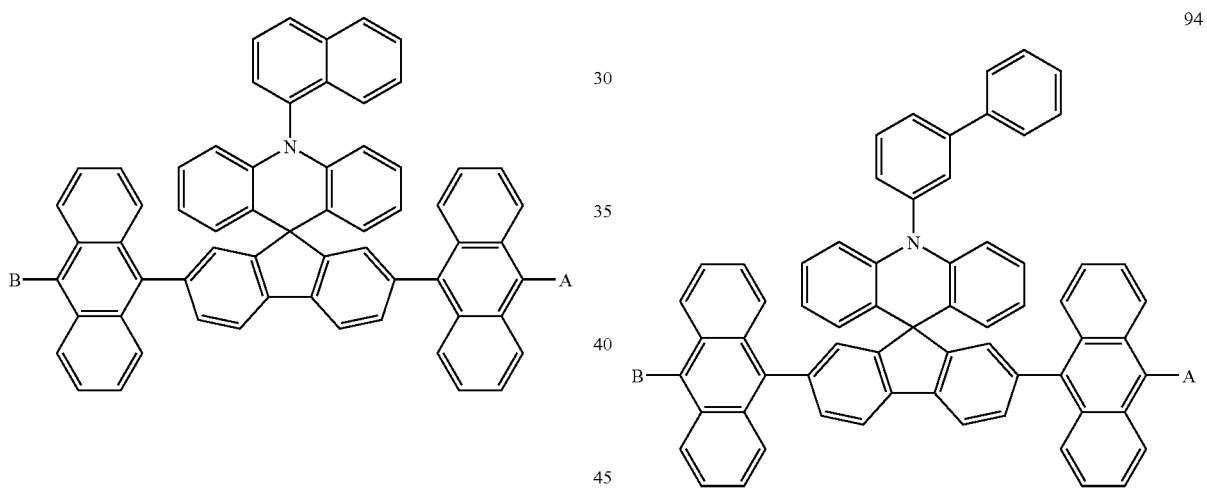
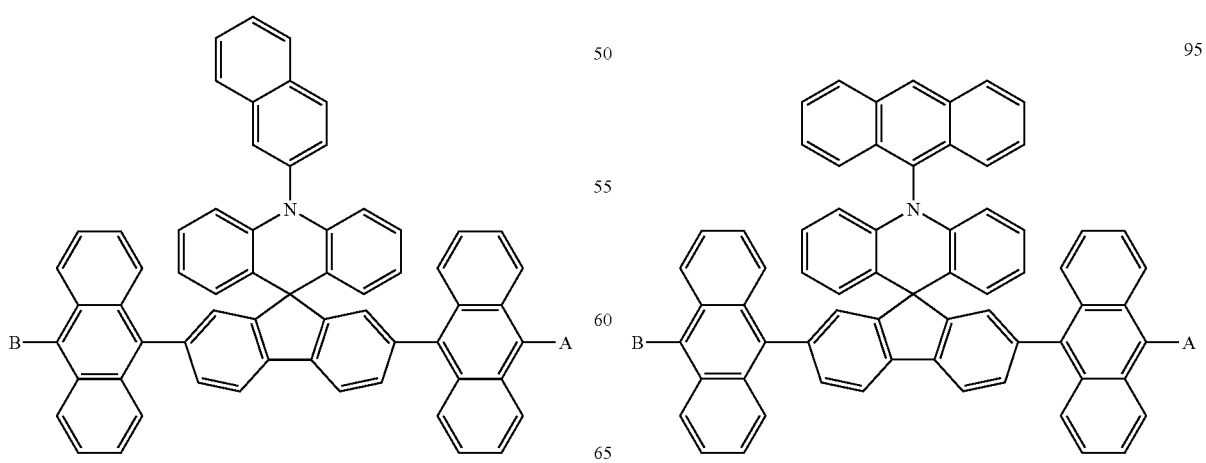

96
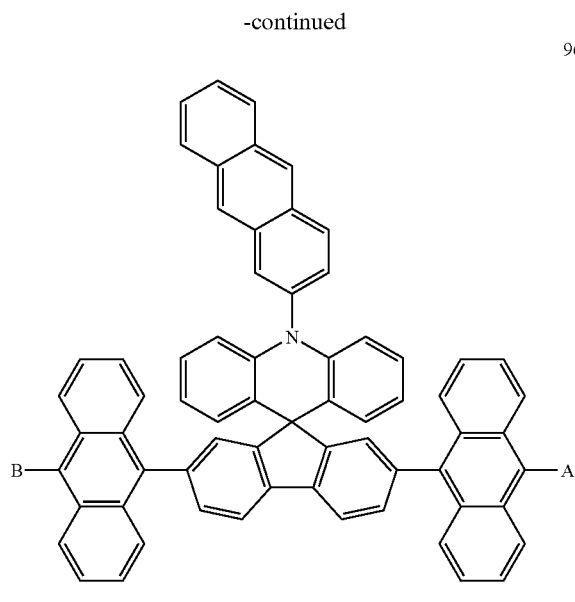
97
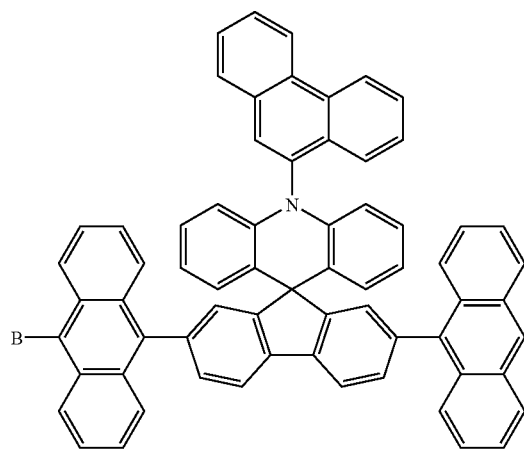
98
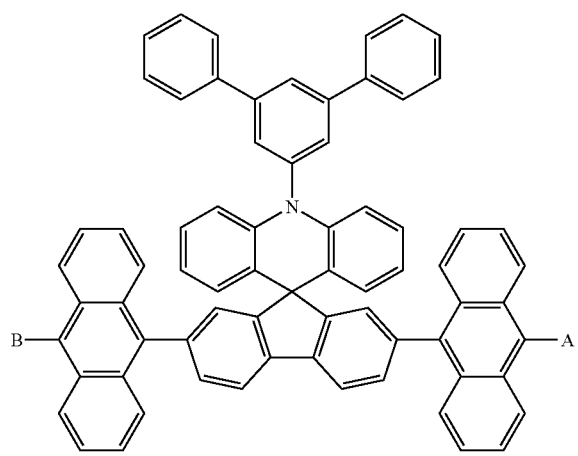
99
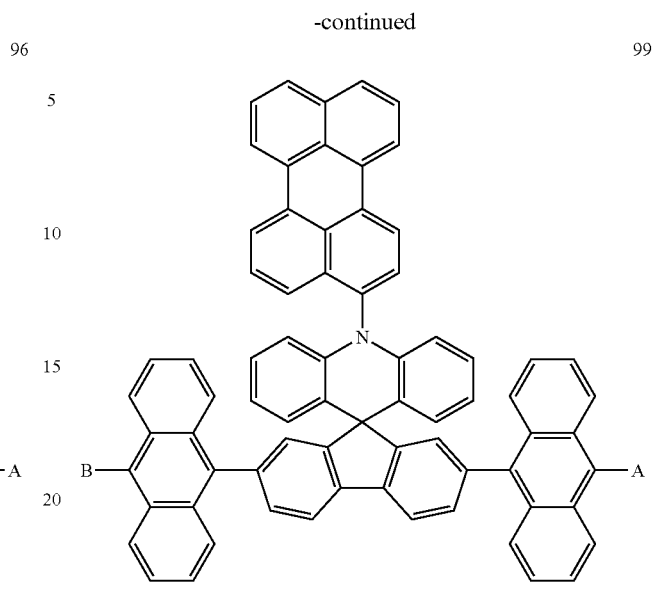
100
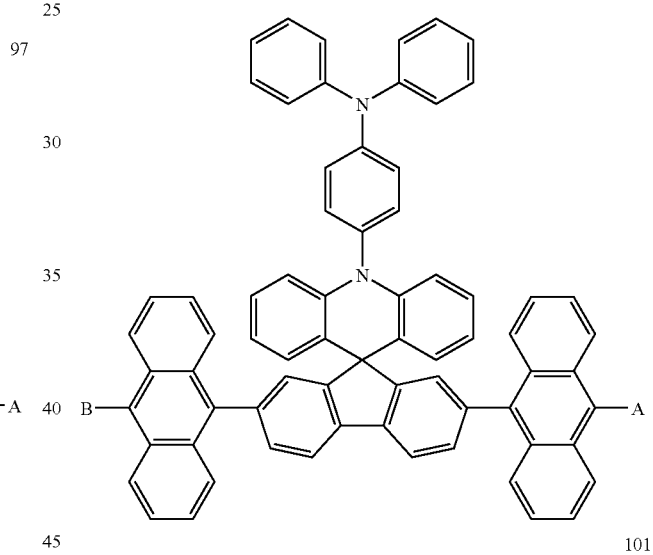

-continued
101
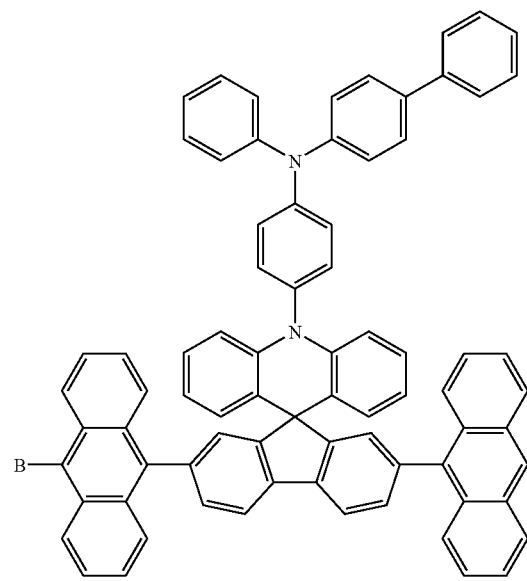
102
102
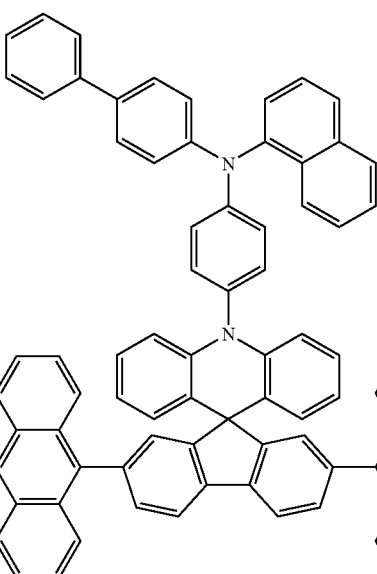
104
103
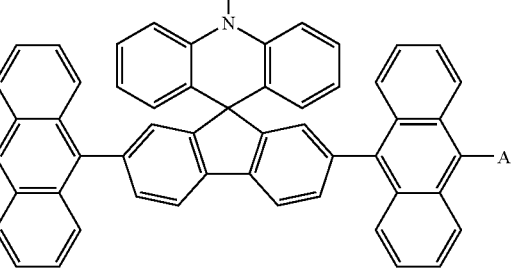
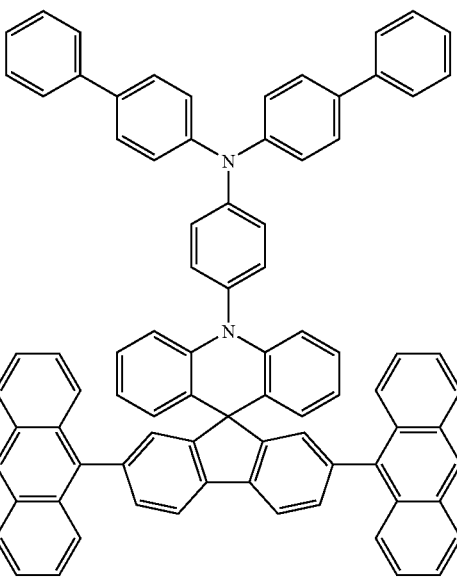
105

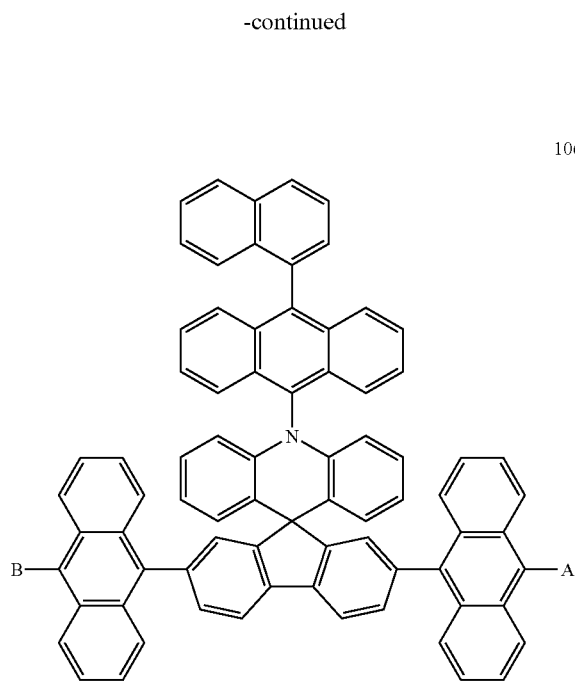
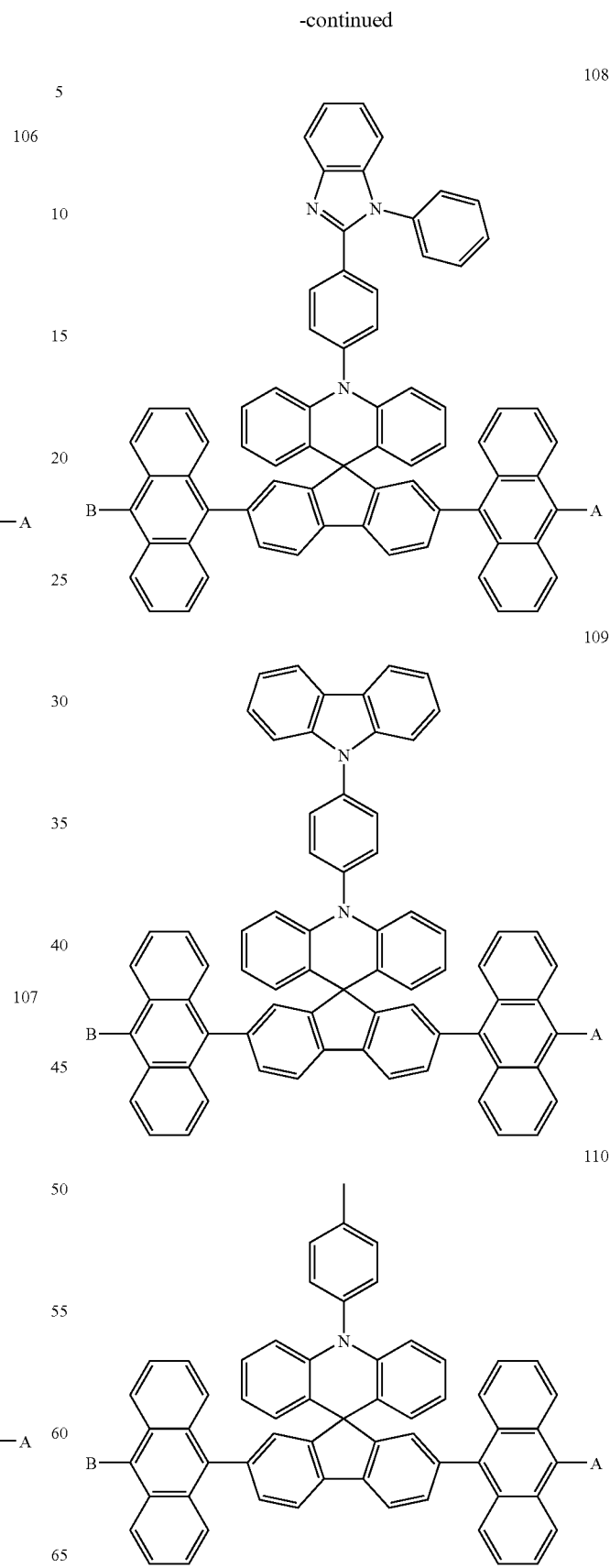

111
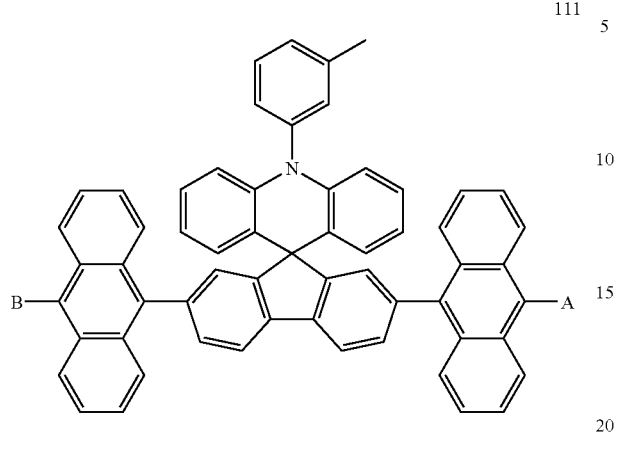
114
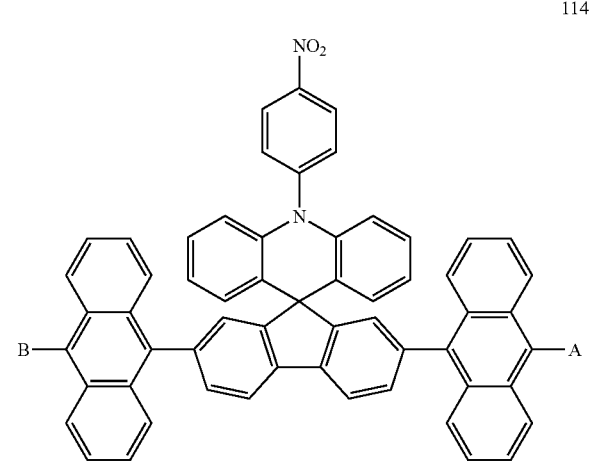
112
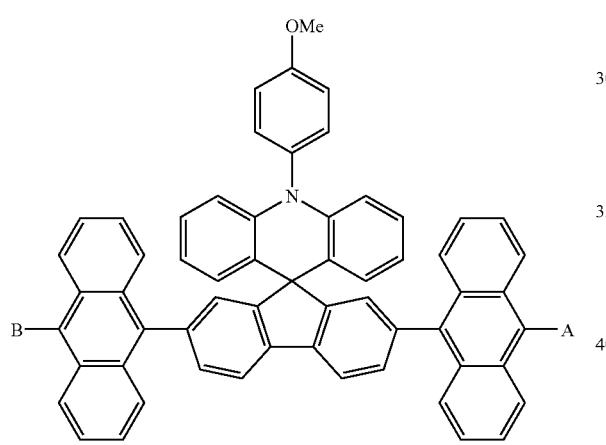
115
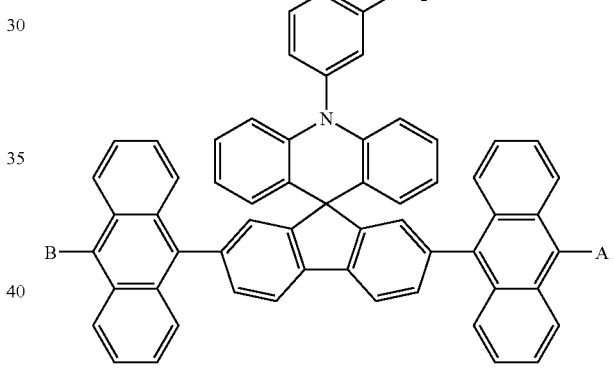
113
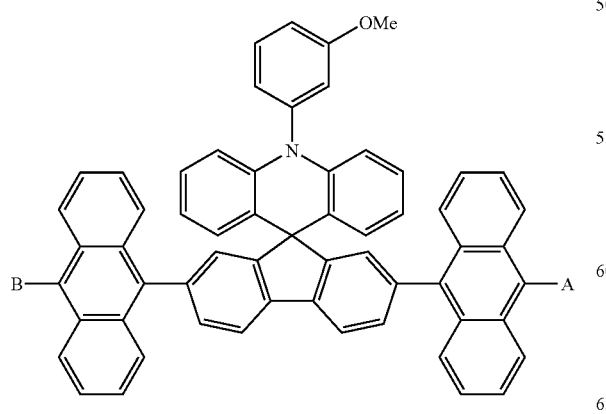
116
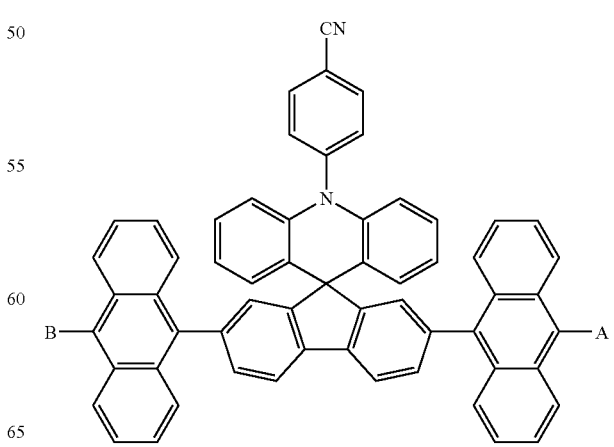

117
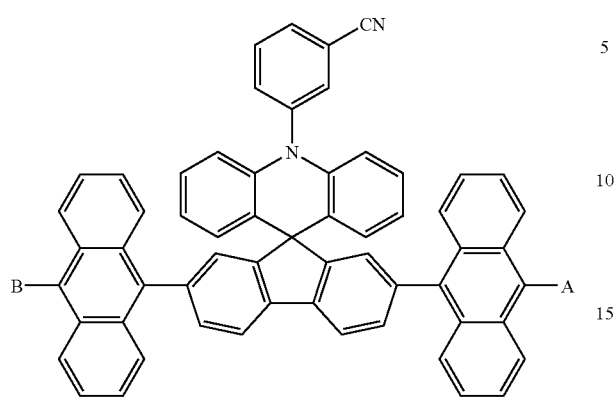
118
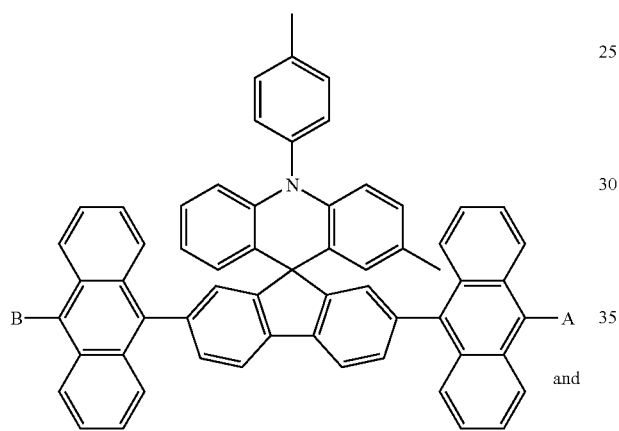
and
119
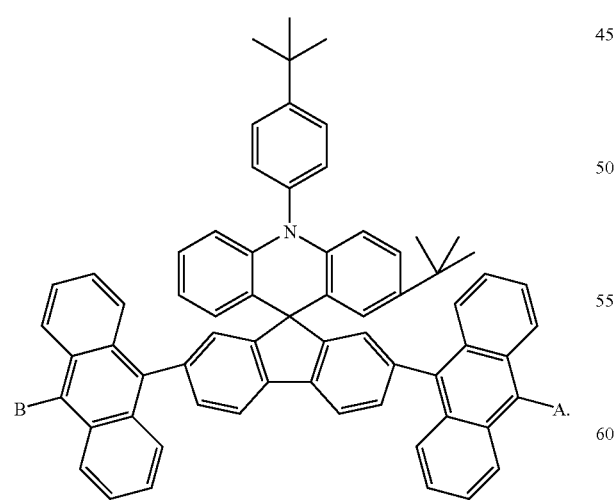
4. The organic light emitting device as set forth in claim 3, wherein A and B are each independently any one of following groups:
1
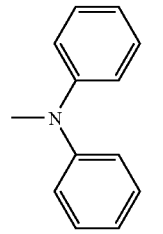
2
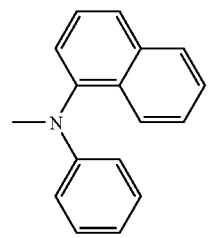
3
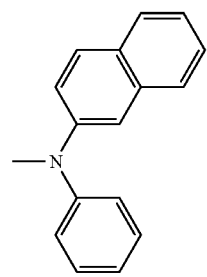
4
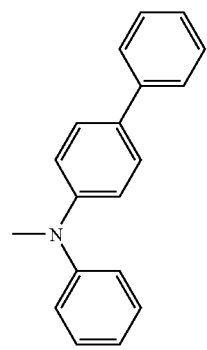
5
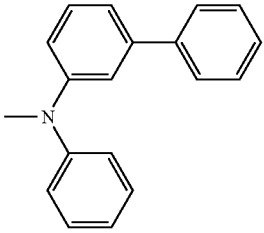
6
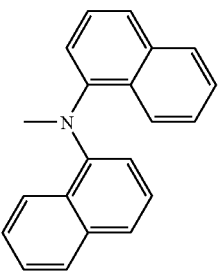

-continued
7
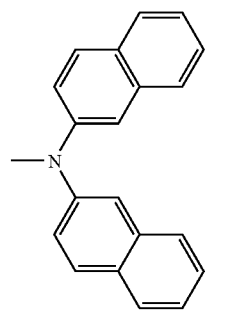
8
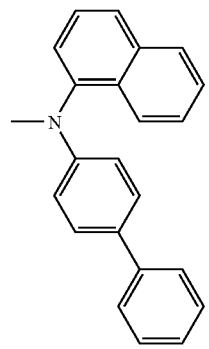
9
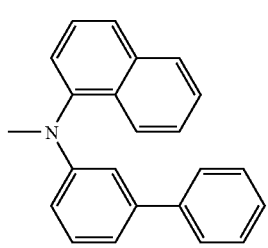
10
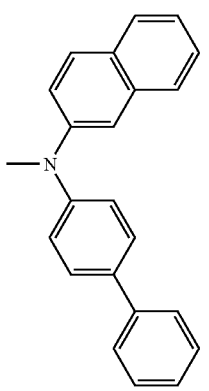
11
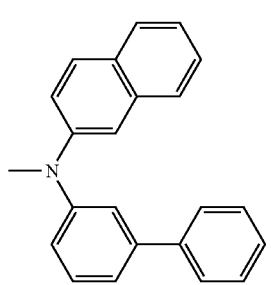
-continued
12
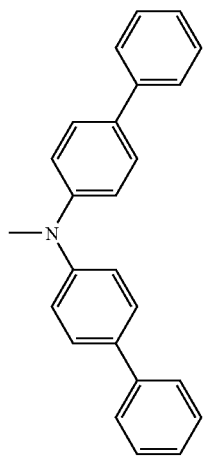
13
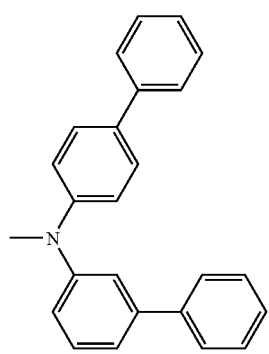
14
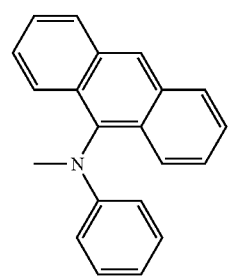
15
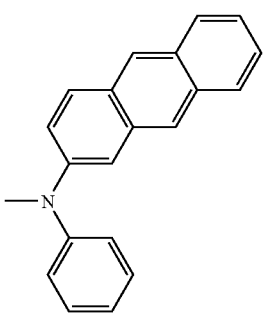

-continued
16
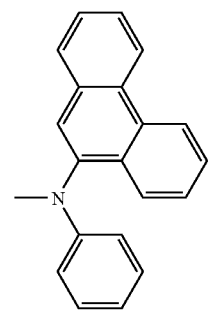
17
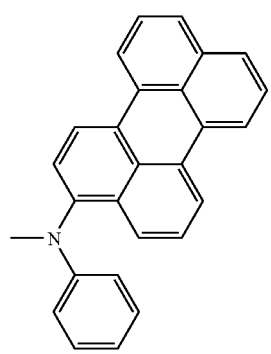
18
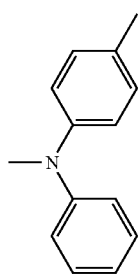
19
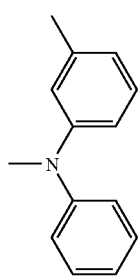
20
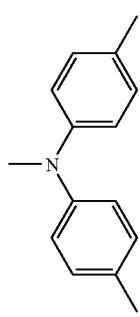
-continued
21
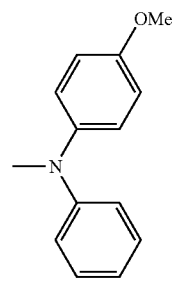
22
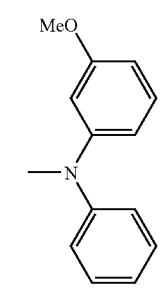
23
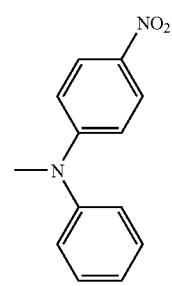
24
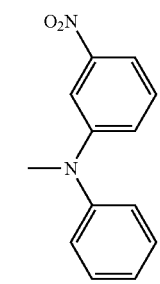
25
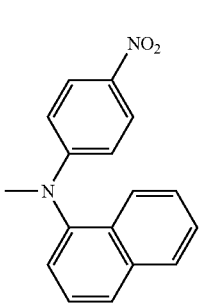

26
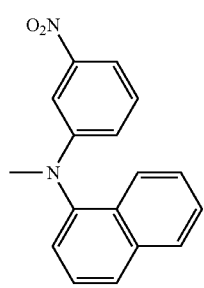
27
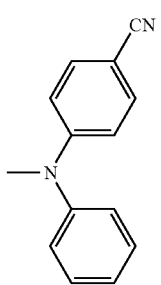
28
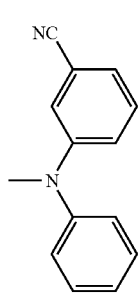
29
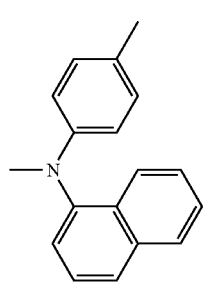
30
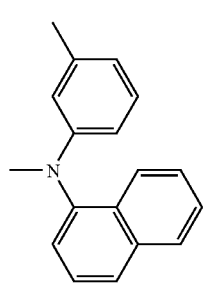
31
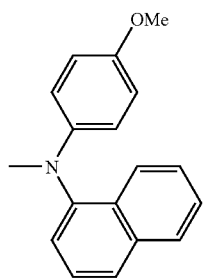
32
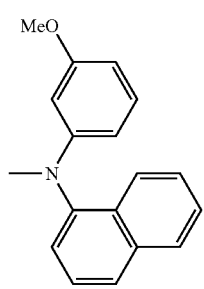
33
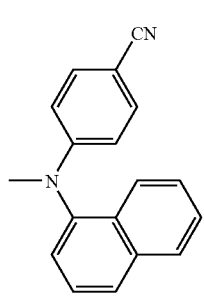
34
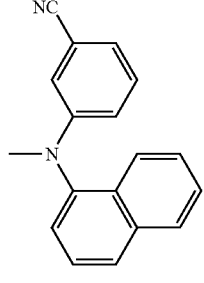
35
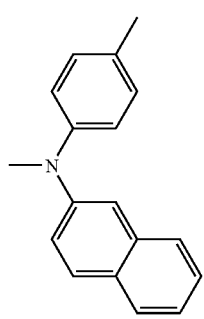

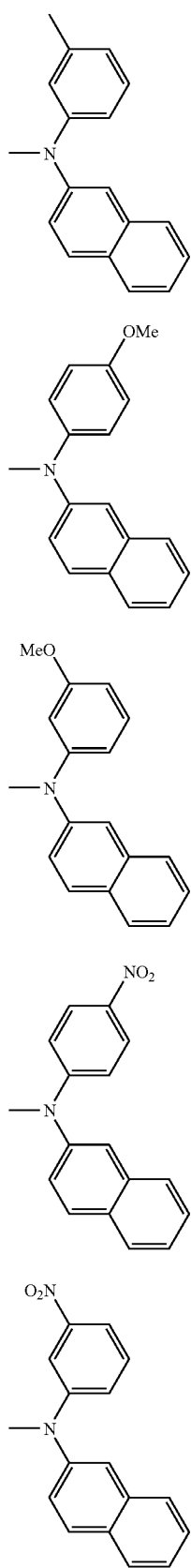
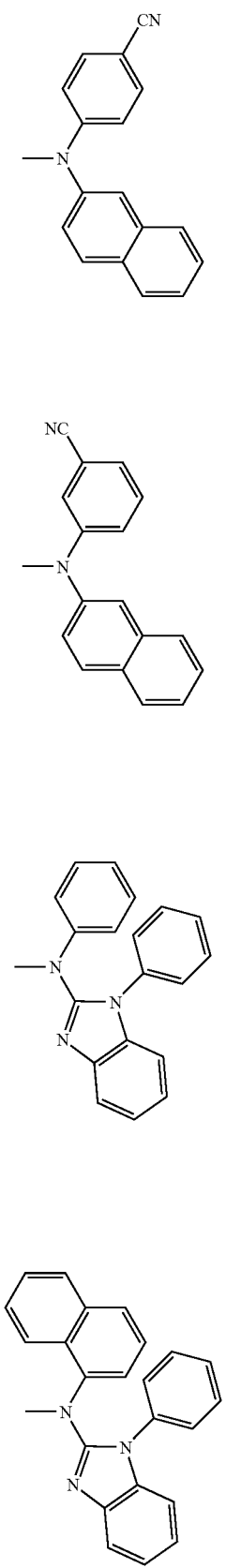

45
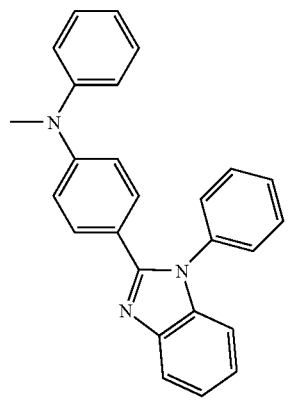
46
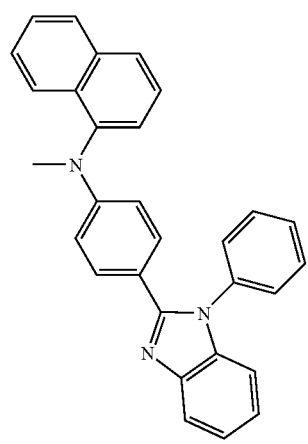
47
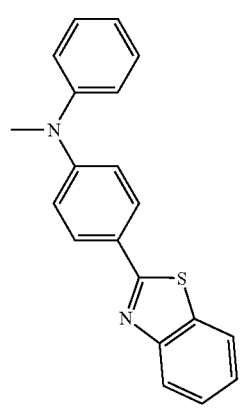
48
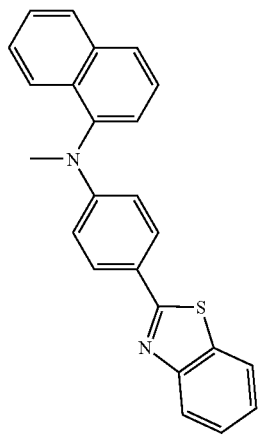
49
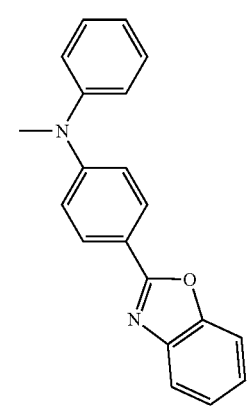
50
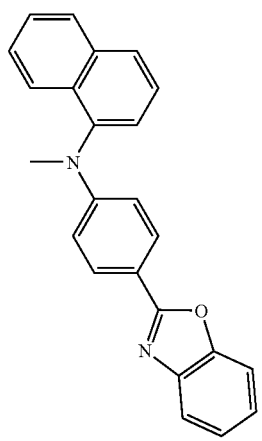
51
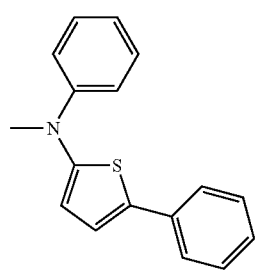

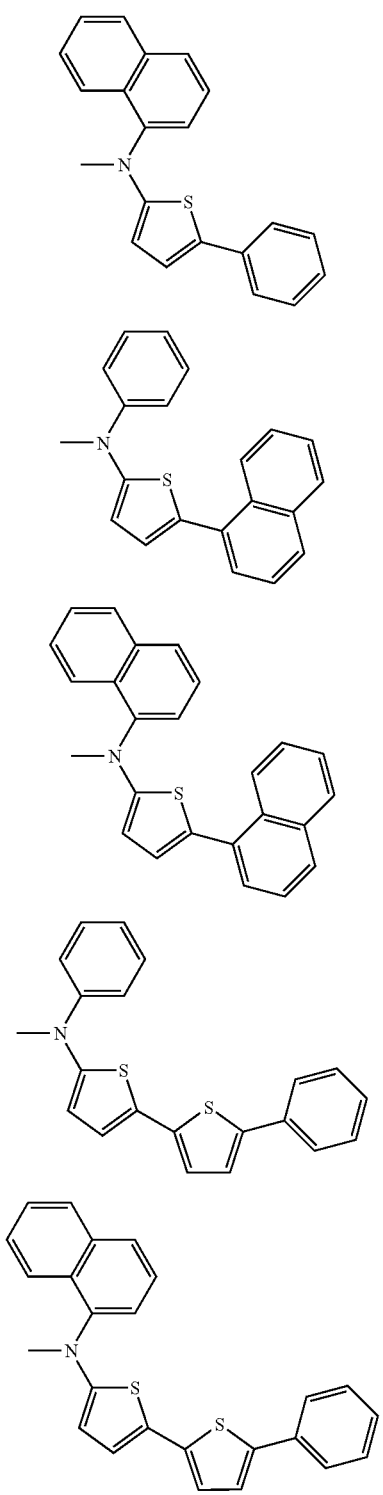

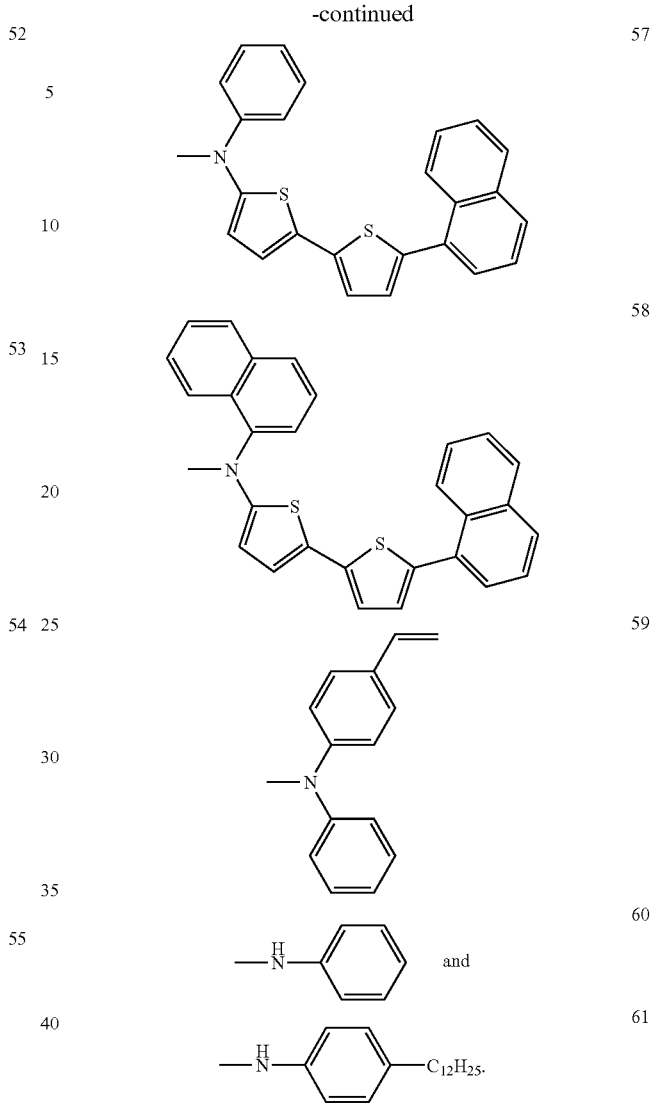

5. The organic light emitting device as set forth in claim 1, wherein the organic material layer(s) comprise a hole transport layer, and the hole transport layer includes the compound of Formula 1.

6. The organic light emitting device as set forth in claim 1, wherein the organic material layer(s) comprise a hole injection layer, and the hole injection layer includes the compound of Formula 1.

7. The organic light emitting device as set forth in claim 1, wherein the organic material layer(s) comprise a layer which both injects and transports holes and which includes the compound of Formula 1.

* * * * *